(12) United States Patent
Tibbs et al.

(10) Patent No.: US 11,684,590 B2
(45) Date of Patent: Jun. 27, 2023

(54) SUBSTITUTED ALKYLPHENOLS AS HCN1 ANTAGONISTS

(71) Applicant: Cornell University, Ithaca, NY (US)

(72) Inventors: Gareth R. Tibbs, Staten Island, NY (US); Peter A. Goldstein, Hartsdale, NY (US); Anthony A. Sauve, New Rochelle, NY (US); Rajendra Uprety, Cary, NC (US); James David Warren, Jr., New York, NY (US); Rebecca L. Joyce, Newark, NJ (US); Dipti N. Barman, Rutherford, NJ (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 17/254,787

(22) PCT Filed: Jun. 27, 2019

(86) PCT No.: PCT/US2019/039493
§ 371 (c)(1),
(2) Date: Dec. 21, 2020

(87) PCT Pub. No.: WO2020/006224
PCT Pub. Date: Jan. 2, 2020

(65) Prior Publication Data
US 2021/0267909 A1    Sep. 2, 2021

Related U.S. Application Data

(60) Provisional application No. 62/803,109, filed on Feb. 8, 2019, provisional application No. 62/690,778, filed on Jun. 27, 2018.

(51) Int. Cl.
*A61K 31/05* (2006.01)
*A61K 47/54* (2017.01)
*A61P 29/02* (2006.01)

(52) U.S. Cl.
CPC .............. *A61K 31/05* (2013.01); *A61K 47/54* (2017.08); *A61K 47/542* (2017.08); *A61K 47/545* (2017.08); *A61P 29/02* (2018.01)

(58) Field of Classification Search
CPC ...................................................... A61K 31/05
USPC ........................................................ 514/359
See application file for complete search history.

(56) References Cited

U.S. PATENT DOCUMENTS

| 4,820,755 | A |   | 4/1989  | Webster |
| 5,126,487 | A | * | 6/1992  | Gibson ................... C07C 45/79 568/319 |
| 6,087,502 | A |   | 7/2000  | Sato |
| 7,820,865 | B2 |   | 10/2010 | Benkoff et al. |
| 9,035,085 | B2 |   | 5/2015  | Gomez-Orellana et al. |
| 2013/0005718 | A1 | * | 1/2013 | Tibbs ....................... A61P 29/00 514/369 |

FOREIGN PATENT DOCUMENTS

| CN | 102382037 | | 3/2012 |
| EP | 303894 | | 9/1988 |
| JP | 10195258 | A2 | 7/1998 |
| JP | 2003-231777 | A2 | 8/2003 |
| WO | WO 1994/014786 | | 7/1994 |
| WO | WO 2001/021166 | A1 | 3/2001 |
| WO | WO 2005/117854 | A2 | 12/2005 |
| WO | WO 2011/019747 | A1 | 2/2011 |
| WO | WO 201101974 | * | 2/2011 |
| WO | WO 2013/024040 | A2 | 2/2013 |
| WO | WO 2014/101237 | A1 | 7/2014 |
| WO | WO 2015/127416 | A1 | 8/2015 |

OTHER PUBLICATIONS

Shpakovsky, Metallomics, 2018, 10, 406-413.*
Koshelev, Molecules 2020, 25, 2370.*
Venkatesh, J. Pharm. Sci. 89, 145-154 (2000).*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
PCT/US2019/039493, Oct. 8, 2019, International Search Report and Written Opinion.
PCT/US2019/039493, Jan. 7, 2021, International Preliminary Report on Patentability.
International Search Report and Written Opinion for PCT/US2019/039493, dated May 20, 2014.
International Preliminary Report on Patentability for PCT/US2019/039493, dated Jun. 9, 2015.
Federal Register (1983), 48(35), 7162, Feb. 18, 1983.
Federal Register (1982), 47(205), 47005, Oct. 22, 1982.
Manteghi et al., Polyolefin elastomer grafted unsaturated hindered phenol esters: synthesis and antioxidant behavior, Designed Monomers Polymers. 2016;19(6):569-576. DOI: 10.1080/15685551.2016. 1187442.
Moreau et al., Synthesis and biological evaluation of acyclic triaryl (Z)-olefins possessing a 3,5-di-tert-butyl-4-hydroxyphenyl pharmacophore: dual inhibitors of cyclooxygenases and lipoxygenases. Bioorg Med Chem. Aug. 1, 2006;14(15):5340-50. doi: 10.1016/j. bmc.2006.03.054. Epub May 3, 2006.

(Continued)

*Primary Examiner* — Nizal S Chandrakumar

(74) *Attorney, Agent, or Firm* — Wolf, Greenfield & Sacks, P.C.

(57) ABSTRACT

Provided herein are compounds (e.g., compounds of Formula (I) and Formula (II), that modulate HCN channels, intermembrane proteins that serve as nonselective voltage-gated cation channels in the plasma membranes of heart and brain cells. Also provided are pharmaceutical compositions and kits comprising the compounds, and methods of treating HCN-related disorders (e.g., pain) with the compounds in a subject, by administering the compounds and/or compositions described herein.

2 Claims, 28 Drawing Sheets

Specification includes a Sequence Listing.

(56) References Cited

OTHER PUBLICATIONS

Rahman et al., Infrared and Raman Spectra of a Single Resin Bead for Analysis of Solid-Phase Reactions and Use in Encoding Combinatorial Libraries. J Org Chem. Sep. 4, 1998;63(18):6196-6199. doi: 10.1021/jo980258w.

Su et al., Solution-phase parallel synthesis and screening of antitumor activities from fenbufen and ethacrynic acid libraries. Bioorg Med Chem Lett. Mar. 1, 2011;21(5):1320-4. doi: 10.1016/j.bmcl.2011.01.068. Epub Jan. 22, 2011.

Tang et al., 3-Phenylpropanoic acid-based phosphotyrosine (pTyr) mimetics: hit evolution to a novel orally active protein tyrosine phosphatase 1B (PTP1B) inhibitor. ChemMedChem. May 2014;9(5):918-21. doi: 10.1002/cmdc.201400007. Epub Mar. 18, 2014.

\* cited by examiner

BP4L-18:1:1

BP4L-10:0:1

SEQUENCE LISTING

```
<160> NUMBER OF SEQ ID NOS: 4

<210> SEQ ID NO 1
<211> LENGTH: 318
<212> TYPE: PRT
<213> ORGANISM: Artificial Sequence
<220> FEATURE:
<223> OTHER INFORMATION: Synthetic polynucleotide

<400> SEQUENCE: 1

Met Glu Gly Pro Arg Arg Gln Tyr Gly Phe Met Gln Arg Gln Phe Thr
1               5                   10                  15

Ser Met Leu Gln Pro Gly Val Asn Lys Phe Ser Leu Arg Met Phe Gly
            20                  25                  30

Ser Gln Lys Ala Val Glu Lys Glu Gln Glu Arg Val Lys Thr Ala Gly
        35                  40                  45

Phe Trp Ile Ile His Pro Tyr Ser Asp Phe Arg Phe Tyr Trp Asp Leu
    50                  55                  60

Ile Met Leu Ile Met Met Val Gly Asn Leu Val Ile Ile Pro Val Gly
65                  70                  75                  80

Ile Thr Phe Phe Thr Glu Gln Thr Thr Thr Pro Trp Ile Ile Phe Asn
                85                  90                  95

Val Ala Ser Asp Thr Val Phe Leu Leu Asp Leu Ile Met Asn Phe Arg
```

```
                100             105             110
Thr Gly Thr Val Asn Glu Asp Ser Ser Glu Ile Ile Leu Asp Pro Lys
            115             120             125
Val Ile Lys Met Asn Tyr Leu Lys Ser Trp Phe Val Asp Phe Ile
            130             135             140
Ser Ser Ile Pro Val Asp Tyr Ile Phe Leu Ile Val Glu Lys Gly Met
145             150             155             160
Asp Ser Glu Val Tyr Lys Thr Ala Arg Ala Leu Arg Ile Val Arg Phe
            165             170             175
Thr Lys Ile Leu Ser Leu Leu Arg Leu Leu Arg Leu Ser Arg Leu Ile
            180             185             190
Arg Tyr Ile His Gln Trp Glu Glu Ile Phe His Met Thr Tyr Asp Leu
            195             200             205
Ala Ser Ala Val Val Arg Ile Phe Asn Leu Ile Gly Met Met Leu Leu
            210             215             220
Leu Cys His Trp Asp Gly Cys Leu Gln Phe Leu Val Pro Leu Leu Gln
225             230             235             240
Asp Phe Pro Pro Asp Cys Trp Val Ser Leu Asn Glu Met Val Asn Asp
            245             250             255
Ser Trp Gly Lys Gln Tyr Ser Tyr Ala Leu Phe Lys Ala Met Ser His
            260             265             270
Met Leu Cys Ile Gly Tyr Gly Ala Gln Ala Pro Val Ser Met Ser Asp
            275             280             285
Leu Trp Ile Thr Met Leu Ser Met Ile Val Gly Ala Thr Cys Tyr Ala
            290             295             300
Met Phe Val Gly His Ala Thr Ala Leu Ile Gln Ser Leu Asp
305             310             315

<210> SEQ ID NO 2
<211> LENGTH: 318
<212> TYPE: PRT
<213> ORGANISM: Artificial Sequence
<220> FEATURE:
<223> OTHER INFORMATION: Synthetic polynucleotide

<400> SEQUENCE: 2

Met Glu Pro Arg Gly Ser Gln Ala Ser Phe Leu Gln Arg Gln Phe Gly
1               5               10              15
Ala Leu Leu Gln Pro Gly Val Asn Lys Phe Ser Leu Arg Met Phe Gly
            20              25              30
Ser Gln Lys Ala Val Glu Arg Glu Gln Glu Arg Val Lys Ser Ala Gly
            35              40              45
Ala Trp Ile Ile His Pro Tyr Ser Asp Phe Arg Phe Tyr Trp Asp Phe
            50              55              60
Thr Met Leu Leu Phe Met Val Gly Asn Leu Ile Ile Pro Val Gly
65              70              75              80
Ile Thr Phe Phe Lys Asp Glu Thr Thr Ala Pro Trp Ile Val Phe Asn
            85              90              95
Val Val Ser Asp Thr Phe Phe Leu Met Asp Leu Val Leu Asn Phe Arg
            100             105             110
Thr Gly Ile Val Ile Glu Asp Asn Thr Glu Ile Ile Leu Asp Pro Glu
            115             120             125
Lys Ile Lys Lys Lys Tyr Leu Arg Thr Trp Phe Val Val Asp Phe Val
            130             135             140
Ser Ser Ile Pro Val Asp Tyr Ile Phe Leu Ile Val Glu Lys Gly Ile
```

```
                145                 150                 155                 160
Asp Ser Glu Val Tyr Lys Thr Ala Arg Ala Leu Arg Ile Val Arg Phe
                    165                 170                 175

Thr Lys Ile Leu Ser Leu Leu Arg Leu Leu Arg Leu Ser Arg Leu Ile
                    180                 185                 190

Arg Tyr Ile His Gln Trp Glu Glu Ile Phe His Met Thr Tyr Asp Leu
                    195                 200                 205

Ala Ser Ala Val Met Arg Ile Cys Asn Leu Ile Ser Met Met Leu Leu
                    210                 215                 220

Leu Cys His Trp Asp Gly Cys Leu Gln Phe Leu Val Pro Met Leu Gln
225                 230                 235                 240

Asp Phe Pro Ser Asp Cys Trp Val Ser Ile Asn Asn Met Val Asn His
                    245                 250                 255

Ser Trp Ser Glu Leu Tyr Ser Phe Ala Leu Phe Lys Ala Met Ser His
                    260                 265                 270

Met Leu Cys Ile Gly Tyr Gly Arg Gln Ala Pro Glu Ser Met Thr Asp
                    275                 280                 285

Ile Trp Leu Thr Met Leu Ser Met Ile Val Gly Ala Thr Cys Tyr Ala
                    290                 295                 300

Met Phe Ile Gly His Ala Thr Ala Leu Ile Gln Ser Leu Asp
305                 310                 315

<210> SEQ ID NO 3
<211> LENGTH: 320
<212> TYPE: PRT
<213> ORGANISM: Artificial Sequence
<220> FEATURE:
<223> OTHER INFORMATION: Synthetic polynucleotide

<400> SEQUENCE: 3

Met Pro Ile Pro Lys Ser Gly Pro Glu Pro Lys Arg Arg His Leu Gly
1               5                   10                  15

Thr Leu Leu Gln Pro Thr Val Asn Lys Phe Ser Leu Arg Val Phe Gly
                    20                  25                  30

Ser His Lys Ala Val Glu Ile Glu Gln Glu Arg Val Lys Ser Ala Gly
                    35                  40                  45

Ala Trp Ile Ile His Pro Tyr Ser Asp Phe Arg Phe Tyr Trp Asp Leu
    50                  55                  60

Ile Met Leu Leu Leu Met Val Gly Asn Leu Ile Val Leu Pro Val Gly
65                  70                  75                  80

Ile Thr Phe Phe Lys Glu Glu Asn Ser Pro Pro Trp Ile Val Phe Asn
                    85                  90                  95

Val Leu Ser Asp Thr Phe Phe Leu Leu Asp Leu Val Leu Asn Phe Arg
                    100                 105                 110

Thr Gly Ile Val Val Glu Glu Gly Ala Glu Ile Leu Leu Ala Pro Arg
                    115                 120                 125

Ala Ile Arg Thr Arg Tyr Arg Leu Thr Trp Phe Leu Val Asp Leu Ile
                    130                 135                 140

Ser Ser Ile Pro Val Asp Tyr Ile Phe Leu Val Val Glu Leu Glu Pro
145                 150                 155                 160

Arg Leu Asp Ala Glu Val Tyr Lys Thr Ala Arg Ala Leu Arg Ile Val
                    165                 170                 175

Arg Phe Thr Lys Ile Leu Ser Leu Leu Arg Leu Leu Arg Leu Ser Arg
                    180                 185                 190

Leu Ile Arg Tyr Ile His Gln Trp Glu Glu Ile Phe His Met Thr Tyr
```

```
                195                 200                 205

Asp Leu Ala Ser Ala Val Val Arg Ile Phe Asn Leu Ile Gly Met Met
        210                 215                 220

Leu Leu Leu Cys His Trp Asp Gly Cys Leu Gln Phe Leu Val Pro Met
225                 230                 235                 240

Leu Gln Asp Phe Pro Pro Asp Cys Trp Val Ser Ile Asn His Met Val
                245                 250                 255

Asn His Ser Trp Gly Arg Gln Tyr Ser His Ala Leu Phe Lys Ala Met
            260                 265                 270

Ser His Met Leu Cys Ile Gly Tyr Gly Gln Gln Ala Pro Val Gly Met
        275                 280                 285

Pro Asp Val Trp Leu Thr Met Leu Ser Met Ile Val Gly Ala Thr Cys
290                 295                 300

Tyr Ala Met Phe Ile Gly His Ala Thr Ala Leu Ile Gln Ser Leu Asp
305                 310                 315                 320

<210> SEQ ID NO 4
<211> LENGTH: 318
<212> TYPE: PRT
<213> ORGANISM: Artificial Sequence
<220> FEATURE:
<223> OTHER INFORMATION: Synthetic polynucleotide

<400> SEQUENCE: 4

Met Glu Val Arg Leu Gly Gln Ser Gly Phe Met Gln Arg Gln Phe Gly
1               5                   10                  15

Ala Met Leu Gln Pro Gly Val Asn Lys Phe Ser Leu Arg Met Phe Gly
            20                  25                  30

Ser Gln Lys Ala Val Glu Arg Glu Gln Glu Arg Val Lys Ser Ala Gly
        35                  40                  45

Phe Trp Ile Ile His Pro Tyr Ser Asp Phe Arg Phe Tyr Trp Asp Leu
    50                  55                  60

Thr Met Leu Leu Leu Met Val Gly Asn Leu Ile Ile Pro Val Gly
65                  70                  75                  80

Ile Thr Phe Phe Lys Asp Glu Asn Thr Thr Pro Trp Ile Val Phe Asn
                85                  90                  95

Val Val Ser Asp Thr Phe Phe Leu Ile Asp Leu Val Leu Asn Phe Arg
            100                 105                 110

Thr Gly Ile Val Val Glu Asp Asn Thr Glu Ile Ile Leu Asp Pro Gln
        115                 120                 125

Arg Ile Lys Met Lys Tyr Leu Lys Ser Trp Phe Val Val Asp Phe Ile
    130                 135                 140

Ser Ser Ile Pro Val Glu Tyr Ile Phe Leu Ile Val Glu Thr Arg Ile
145                 150                 155                 160

Asp Ser Glu Val Tyr Lys Thr Ala Arg Ala Val Arg Ile Val Arg Phe
                165                 170                 175

Thr Lys Ile Leu Ser Leu Leu Arg Leu Leu Arg Leu Ser Arg Leu Ile
            180                 185                 190

Arg Tyr Ile His Gln Trp Glu Glu Ile Phe His Met Thr Tyr Asp Leu
        195                 200                 205

Ala Ser Ala Val Val Arg Ile Val Asn Leu Ile Gly Met Met Leu Leu
    210                 215                 220

Leu Cys His Trp Asp Gly Cys Leu Gln Phe Leu Val Pro Met Leu Gln
225                 230                 235                 240

Asp Phe Pro His Asp Cys Trp Val Ser Ile Asn Gly Met Val Asn Asn
```

```
                        245                 250                 255
Ser Trp Gly Lys Gln Tyr Ser Tyr Ala Leu Phe Lys Ala Met Ser His
                260                 265                 270
Met Leu Cys Ile Gly Tyr Gly Arg Gln Ala Pro Val Gly Met Ser Asp
            275                 280                 285
Val Trp Leu Thr Met Leu Ser Met Ile Val Gly Ala Thr Cys Tyr Ala
        290                 295                 300
Met Phe Ile Gly His Ala Thr Ala Leu Ile Gln Ser Leu Asp
305                 310                 315
```

SUBSTITUTED ALKYLPHENOLS AS HCN1 ANTAGONISTS

RELATED APPLICATIONS

The present application is a national stage filing under 35 U.S.C. § 371 of international PCT application, PCT/US2019/039493, filed Jun. 27, 2019, which claims priority under 35 U.S.C. § 119(e) to U.S. provisional applications U.S. Ser. No. 62/690,778, filed Jun. 27, 2018, and U.S. Ser. No. 62/803,109, filed Feb. 8, 2019, each of which is incorporated herein by reference in its entirety.

BACKGROUND OF THE INVENTION

Chronic pain is pain that persists for over three months. Such pain greatly impairs an individual's quality of life, is widely prevalent, and has significant economic cost.

Neuropathic pain is a form of chronic pain caused by a lesion of, or damage to, the somatosensory nervous system. Neuropathic pain is a pathologic feature of numerous conditions, including postherpetic neuralgia, trigeminal neuralgia, sensory (painful) radiculopathy, painful diabetic neuropathy, peripheral nerve injury, stroke, multiple sclerosis, and cancer treatment with antineoplastics. Globally, about 7-10% of the population lives with chronic pain with neuropathic features. Cardinal symptoms of neuropathic pain are spontaneous pain, abnormal response to nonpainful (allodynia) or painful (hyperalgesia) stimuli, dysesthesia (unpleasant/strange sensation—"tingling" "pins and needles"), and enhanced thermal sensitivity; numerous pharmacologic approaches to relieving neuropathic pain have been proposed, but their efficacy is limited, resulting in a large unmet need with respect to providing meaningful pain relief.

Recent studies suggest that neuropathic pain might better be understood at the mechanistic level as a function of sensory profiling rather than disease etiology. Hyperexcitability of primary afferent neurons is thought to be an early causal factor leading to the development and maintenance of peripheral neuropathic pain. Numerous ion channel families contribute to this hyperexcitability, including the hyperpolarization-activated, cyclic nucleotide-gated (HCN) channel family. In animal models of neuropathic pain, non-selective HCN block with either ZD7288 or the clinically-available drug ivabradine results in significant anti-hyperalgesia. Expression of the HCN isoform, HCN1, is up-regulated in multiple animal models of neuropathic pain including those where the initiating injury was mechanical damage, chemotherapy administration, or diabetes. Antihyperalgesic activity is retained in HCN1-selective molecules, suggesting that HCN1-selective blockade has therapeutic potential.

SUMMARY OF THE INVENTION

The present disclosure stems from the recognition that, by targeting and modulating (e.g., inhibiting) peripheral sensory neuron channels (e.g., HCN1), new compounds, compositions, uses, and methods are provided that are useful for the treatment of pain. In models of neuropathic pain, for example, inhibition of HCN1 is antihyperalgesic. In particular, 2,6-di-iso-propylphenol and its non-anesthetic congener, 2,6-di-tert-butylphenol, inhibit HCN1 channels by stabilizing closed states of HCN1, resulting in a therapeutic effect. Accordingly, the present disclosure provides a means of locating a plasma membrane-penetrant pharmacophore tethered to the external face of a plasma membrane by generating molecules having a polar anchor moiety that restricts the pharmacophore to the periphery of the cell, thereby promoting contact with therapeutically-important peripheral sensory neuron targets (e.g., HCN1).

The present disclosure provides novel compounds that modulate HCN channels, and in particular are selective modulators (e.g., inhibitors) of HCN1, thereby providing therapeutic agents useful in the treatment and/or management of pain (e.g., chronic pain).

In one aspect, provided is a compound of Formula (I):

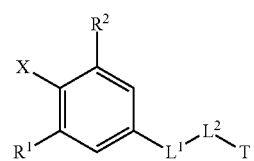

(I)

or a pharmaceutically acceptable salt thereof;
wherein:

$R^1$ is unsubstituted alkyl;

$R^2$ is unsubstituted alkyl;

X is halogen, —OP, —N($R^A$)$_2$, —N$R^A$N($R^A$)$_2$, —SP, or —NCO;

P is hydrogen, an oxygen protecting group, a sulfur protecting group, or substituted or unsubstituted heterocyclyl;

$L^1$ is —(C=O)—, —CH$_2$—, —CH=CH—, —O—, —S—, or —N$R^A$—;

$L^2$ is substituted or unsubstituted alkylene, substituted or unsubstituted alkenylene, substituted or unsubstituted alkynylene, substituted or unsubstituted heteroalkylene, substituted or unsubstituted heteroalkenylene, or substituted or unsubstituted heteroalkynylene, wherein $L^2$ comprises a chain of at least 8 continuous non-hydrogen atoms from its point of attachment to $L^1$ to its point of attachment to T;

T is substituted alkyl, substituted or unsubstituted alkenyl, substituted or unsubstituted alkynyl, substituted or unsubstituted heteroalkyl, —OR$^C$, —N(R$^A$)$_2$, —SR$^A$, —CO$_2$H, halogen, —OS(O$_2$)R$^B$, —O(C=O)R$^C$, —(C=O)OR$^C$, —O(C=O)OR$^C$, —(C=O)N(R$^A$)$_2$, —O(C=O)N(R$^A$)$_2$, —NR$^A$(C=O)N(R$^A$)$_2$, —CN, —CHO, —N$_3$, —N=C=S,

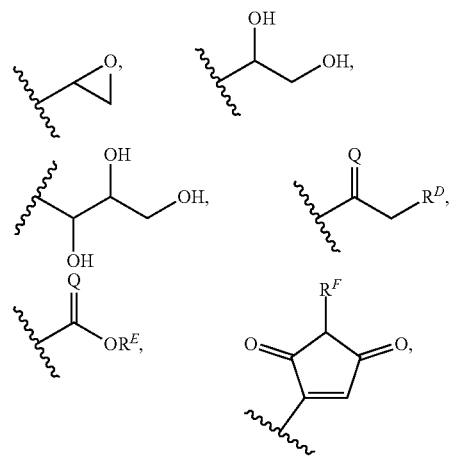

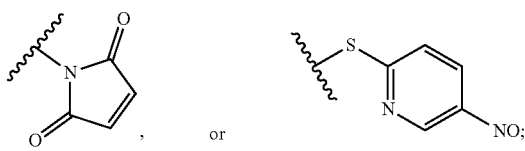

Q is S or O;

each $R^A$ is independently hydrogen, substituted or unsubstituted alkyl, substituted or unsubstituted heteroalkyl, substituted or unsubstituted acyl, substituted or unsubstituted heterocyclyl, a nitrogen protecting group, or a sulfur protecting group;

$R^B$ is substituted or unsubstituted alkyl or substituted or unsubstituted aryl;

$R^C$ is substituted or unsubstituted alkyl, substituted or unsubstituted aryl, substituted or unsubstituted heterocyclyl, substituted or unsubstituted heteroaryl, or an oxygen protecting group;

$R^D$ is halogen or $-OS(O_2)R^B$;

$R^E$ is hydrogen, substituted or unsubstituted alkyl, substituted or unsubstituted carbocyclyl, substituted or unsubstituted heterocyclyl, substituted or unsubstituted aryl, substituted or unsubstituted heteroaryl, or an oxygen protecting group; and $R^F$ is hydrogen, substituted or unsubstituted alkyl, or a nitrogen protecting group;

provided that the compound is not:

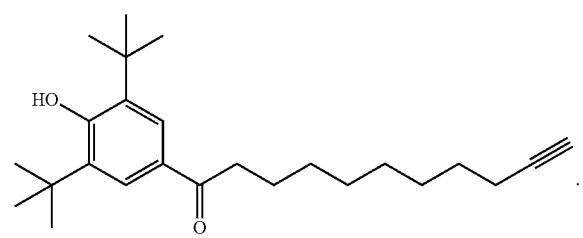 [SMILES: C#CCCCCCCCCC(=O)c1cc(C(C)(C)C)c(O)c(C(C)(C)C)c1]

In certain embodiments, the compound of Formula (I) is of Formula (I-a):

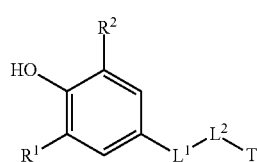

(I-a)

or a pharmaceutically acceptable salt thereof.

In certain embodiments, the compound of Formula (I) is of Formula (I-b):

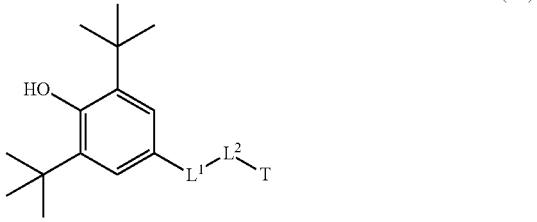

(I-b)

or a pharmaceutically acceptable salt thereof.

In certain embodiments, the compound of Formula (I) is of Formula (I-c):

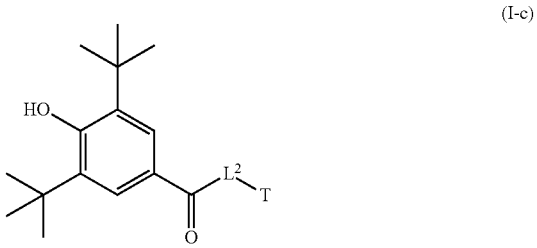

(I-c)

or a pharmaceutically acceptable salt thereof.

In certain embodiments, the compound of Formula (I) is of Formula (I-d):

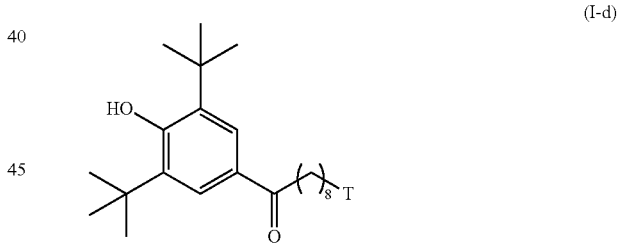

(I-d)

or a pharmaceutically acceptable salt thereof.

In certain embodiments, the compound of Formula (I) is of Formula (I-e):

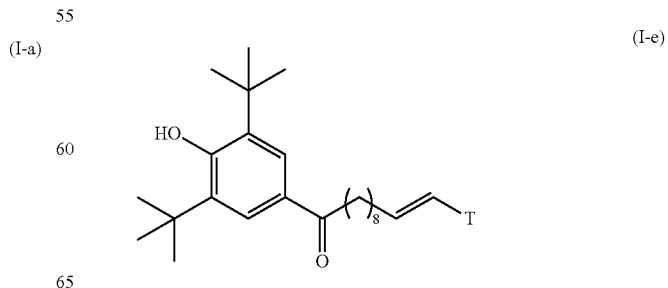

(I-e)

or a pharmaceutically acceptable salt thereof.

In another aspect, provided is a compound of Formula (II):

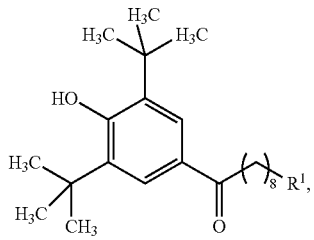

(II)

or a pharmaceutically acceptable salt and/or solvate thereof, wherein:

$R^1$ is —CH(OH)CH$_2$(OH), —CH(X$^1$)CH$_3$, CH$_2$CH$_3$, —CH=CH$_2$, —CH=CH(R$^2$), or —CH$_2$CH$_2$(R$^3$);

$R^2$ is —(CH$_2$)$_m$CH(OH)CH$_2$(OH), —(CH$_2$)$_p$CH(X$^2$)CH$_3$, —(CH$_2$)$_t$CH=CH$_2$, or —(CH$_2$)$_v$CH$_2$CH$_3$;

$R^3$ is —(CH$_2$)$_w$CH(OH)CH$_2$(OH), —(CH$_2$)$_x$CH(X$^3$)CH$_3$, —(CH$_2$)$_y$CH=CH$_2$, or —(CH$_2$)$_z$CH$_2$CH$_3$;

$X^1$, $X^2$, and $X^3$ are each independently Cl or F;

n is 1, 2, 3, 4, 5, 6, 7, 8, 9, 10, 11, 12, 13, 14, or 15;
m is 0, 1, 2, 3, 4, 5, 6, 7, 8, 9, 10, 11, 12, 13, 14, or 15;
p is 0, 1, 2, 3, 4, 5, 6, 7, 8, 9, 10, 11, 12, 13, 14, or 15;
t is 0, 1, 2, 3, 4, 5, 6, 7, 8, 9, 10, 11, 12, 13, 14, or 15;
v is 0, 1, 2, 3, 4, 5, 6, 7, 8, 9, 10, 11, 12, 13, 14, or 15;
w is 0, 1, 2, 3, 4, 5, 6, 7, 8, 9, 10, 11, 12, 13, 14, or 15;
x is 0, 1, 2, 3, 4, 5, 6, 7, 8, 9, 10, 11, 12, 13, 14, or 15;
y is 0, 1, 2, 3, 4, 5, 6, 7, 8, 9, 10, 11, 12, 13, 14, or 15; and
z is 0, 1, 2, 3, 4, 5, 6, 7, 8, 9, 10, 11, 12, 13, 14, or 15.

In another aspect, provided are pharmaceutical compositions comprising a compound of Formula (I) or Formula (II), or a pharmaceutically acceptable salt thereof, and a pharmaceutically acceptable carrier.

In another aspect, provided are methods of treating pain (e.g., chronic pain) in a subject in need thereof, the method comprising administering to the subject an effective amount of a compound of Formula (I) or Formula (II), or a pharmaceutically acceptable salt thereof, or a pharmaceutical composition thereof to the subject.

In another aspect, provided are methods of modulating (e.g., inhibiting) HCN channel gating (e.g., HCN1 channel gating), the method comprising contacting an HCN channel with an effective amount of a compound of Formula (I) or Formula (II), or a pharmaceutically acceptable salt thereof, or a pharmaceutical composition thereof.

In another aspect, provided are methods of inhibiting an HCN1 channel without enhancing a gamma-aminobutyric acid-A (GABA-A) receptor, the method comprising contacting an HCN1 channel with an effective amount of a compound of Formula (I) or Formula (II), or pharmaceutically acceptable salts thereof, or a pharmaceutical composition thereof.

In another aspect, provided are methods of inhibiting an HCN1 channel without modulating the activity of a GABA-A receptor, the method comprising contacting an HCN1 channel with an effective amount of a compound of Formula (I) or Formula (II), or pharmaceutically acceptable salts thereof, or a pharmaceutical composition thereof.

The details of one or more embodiments of the invention are set forth in the accompanying Figures and the Detailed Description below. Other features, objects, and advantages of the invention will be apparent from the Examples and the Claims.

Definitions

Chemical Definitions

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* 3rd Edition, Cambridge University Press, Cambridge, 1987.

Compounds described herein may comprise one or more stereogenic centers, and thus may exist as stereoisomers, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., *Tetrahedron* 33:2725 (1977); Eliel, E. L. Stereochemistry of Carbon Compounds (McGraw-Hill, N Y, 1962); and Wilen, S. H. Tables of Resolving Agents and Optical Resolutions p. 268 (E. L. Eliel, Ed., Univ. of Notre Dame Press, Notre Dame, Ind. 1972). Compounds may exist as individual isomers substantially free of other isomers, and alternatively, as mixtures of various isomers.

When a range of values is listed, it is intended to encompass each value and sub-range within the range. For example "C1-6 alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("C1 alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl (C$_3$), n-butyl (C$_4$), tert-butyl (C$_4$), sec-butyl (C$_4$), iso-butyl (C$_4$), n-pentyl (C$_5$), 3-pentanyl (C5), amyl (C5), neopentyl (C$_5$), 3-methyl-2-butanyl (C$_5$), tertiary amyl (C$_5$), and n-hexyl (C6). Additional examples of alkyl groups include n-heptyl (C$_7$), n-octyl (C$_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted C$_{1-10}$ alkyl (e.g., —CH$_3$). In certain embodiments, the alkyl group is a substituted C$_{1-10}$ alkyl.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and for 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C═C double bond for which the stereochemistry is not specified (e.g., —CH═CHCH$_3$ or

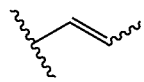

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and for 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or Spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl. As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetra¬hydro¬benzo¬thienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetra¬hydro¬pyrano[3,4-b]pyrrolyl, 5,6-dihydro-4H-furo[3,2-b]pyrrolyl, 6,7-dihydro-5H-furo¬[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-¬[2,3-b]pyridinyl, 4,5,6,7-tetra¬hydro¬furo[3,2-c]pyridinyl, 4,5,6,7-tetrahydro¬thieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C6-14 aryl"). In some embodiments, an aryl group has 6 ring carbon atoms ("C6 aryl"; e.g., phenyl). In some embodiments, an aryl group has 10 ring carbon atoms ("C10 aryl"; e.g., naphthyl such as 1-naphthyl and 2-naphthyl). In some embodiments, an aryl group has 14 ring carbon atoms ("C14 aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted C6-14 aryl. In certain embodiments, the aryl group is a substituted C6-14 aryl.

"Aralkyl" is a subset of "alkyl" and refers to an alkyl group, as described herein, substituted by an aryl group, as described herein, wherein the point of attachment is on the alkyl moiety.

As used herein, "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as described herein, substituted by a heteroaryl group, as described herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as described herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_3$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$R$^{aa}$, —SO$_2$OR$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl), —OC(=NH)NH(C$_{1-6}$ alkyl), —OC(=NH)NH$_2$, —NHC(=NH)N(C$_{1-6}$ alkyl)$_2$, —NHC(=NH)NH$_2$, —NHSO$_2$(C$_{1-6}$ alkyl), —SO$_2$N(C$_{1-6}$ alkyl), —SO$_2$NH(C$_{1-6}$ alkyl), —SO$_2$NH$_2$, —SO$_2$(C$_{1-6}$ alkyl), —SO$_2$O(C$_{1-6}$ alkyl), —OSO$_2$(C$_{1-6}$ alkyl), —SO(C$_{1-6}$ alkyl), —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

As used herein, the term "halo" or "halogen" refers to fluorine (fluoro, —F), chlorine (chloro, —Cl), bromine (bromo, —Br), or iodine (iodo, —I).

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, —C(=S)O(R$^{X1}$), —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "leaving group" is given its ordinary meaning in the art of synthetic organic chemistry and refers to an atom or a group capable of being displaced by a nucleophile. See, for example, Smith, *March's Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. Further exemplary leaving groups include, but are not limited to, halo (e.g., chloro, bromo, iodo) and activated substituted hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein).

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(=O)(R$^{aa}$)$_2$, —OP(=O)(OR$^{cc}$)$_2$, and —OP(=O)(N(R$^{bb}$)$_2$)$_2$, wherein X$^-$, R$^{aa}$, R$^{bb}$, and R$^{cc}$ are as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as described herein.

As used herein, the term, "amino" refers to the group —NH$_2$. The term "substituted amino," by extension, refers to a monosubstituted amino, a disubstituted amino, or a trisubstituted amino, as described herein. In certain embodiments, the "substituted amino" is a monosubstituted amino or a disubstituted amino group.

As used herein, "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —NHCO$_2R^{aa}$, —NHC(=O)$^N(R^{bb})_2$, —NHC(=N$R^{bb}$)N($R^{bb})_2$, —NHSO$_2R^{aa}$, —NHP(=O)(O$R^{cc})_2$, and —NHP(=O)(N($R^{bb})_2)_2$, wherein $R^{aa}$, $R^{bb}$, and $R^{cc}$ are as defined herein, and wherein $R^{bb}$ of the group —NH($R^{bb}$) is not hydrogen.

As used herein, the term "disubstituted amino" refers to an amino group wherein the nitrogen atom directly attached to the parent molecule is substituted with two groups other than hydrogen, and includes groups selected from —N($R^{bb})_2$, —N$R^{bb}$C(=O)$R^{aa}$, —N$R^{bb}$CO$_2R^{aa}$, —N$R^{bb}$C(=O)N($R^{bb})_2$, —N$R^{bb}$C(=N$R^{bb}$)N($R^{bb})_2$, —N$R^{bb}$SO$_2R^{aa}$, —N$R^{bb}$P(=O)(O$R^{cc})_2$, and —N$R^{bb}$P(=O)(N($R^{bb})_2)_2$, wherein $R^{aa}$, $R^{bb}$, and $R^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups, and includes groups selected from —N($R^{bb})_3$ and —N($R^{bb})_3^+$ $X^-$, wherein $R^{bb}$ and $X^-$ are as defined herein.

As used herein, the term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc})_2$, —CN, —C(=O)$R^{aa}$, —C(=O)N($R^{cc})_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc})_2$, —SO$_2$N($R^{cc})_2$, —SO$_2R^{cc}$, —SO$_2$O$R^{cc}$, —SO$R^{aa}$, —C(=S)N($R^{cc})_2$, —C(=O)S$R^{cc}$, —C(=S)S$R^{cc}$, —P(=O)(O$R^{cc})_2$, —P(=O)($R^{aa})_2$, —P(=O)(N($R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined herein.

In certain embodiments, the substituent present on the nitrogen atom is a nitrogen protecting group (also referred to herein as an "amino protecting group"). Nitrogen protecting groups include, but are not limited to, —OH, —O$R^{aa}$, —N($R^{cc})_2$, —C(=O)$R^{aa}$, —C(=O)N($R^{cc})_2$, —CO$_2R^{aa}$, —SO$_2R^{aa}$, —C(=N$R^{cc}$)$R^{aa}$, —C(=N$R^{cc}$)O$R^{aa}$, —C(=N$R^{cc}$)N($R^{cc})_2$, —SO$_2$N($R^{cc})_2$, —SO$_2R^{cc}$, —SO$_2$O$R^{cc}$, —SO$R^{aa}$, —C(=S)N($R^{cc})_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)O$R^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl) methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridypethyl carbamate, phenyl carbamate, p-(phenylazo)

benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethyl sulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-flurenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2-trichloroethyloxycarbonyl (Troc), triphenylmethyl (Tr), tosyl (Ts), brosyl (Bs), nosyl (Ns), mesyl (Ms), triflyl (Tf), or dansyl (Ds).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{cc}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate, 2-10 dobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group is silyl. In certain embodiments, an oxygen protecting group is t-butyldiphenylsilyl (TBDPS), t-butyldimethylsilyl (TBDMS), triisoproylsilyl (TIPS), triphenylsilyl (TPS), triethylsilyl (TES), trimethylsilyl (TMS), triisopropylsiloxymethyl (TOM), acetyl (Ac), benzoyl (Bz), allyl carbonate, 2,2,2-trichloroethyl carbonate (Troc), 2-trimethylsilylethyl carbonate, methoxymethyl (MOM), 1-ethoxyethyl (EE), 2-methyoxy-2-propyl (MOP), 2,2,2-trichloroethoxyethyl, 2-methoxyethoxymethyl (MEM), 2-trimethylsilylethoxymethyl (SEM), methylthiomethyl (MTM), tetrahydropyranyl (THP), tetrahydrofuranyl (THF), p-methoxyphenyl (PMP), triphenylmethyl (Tr), methoxytrityl (MMT), dimethoxytrityl (DMT), allyl, p-methoxybenzyl (PMB), t-butyl, benzyl (Bn), allyl, or pivaloyl (Piv).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

These and other exemplary substituents are described in more detail in the Detailed Description, Examples, Figures, and Claims. The invention is not intended to be limited in any manner by the above exemplary listing of substituents.

Other Definitions

The term "antagonist" refers to an agent that (i) decreases or suppresses one or more effects of another agent; and/or (ii) decreases or suppresses one or more biological events. In some embodiments, an antagonist may reduce level and/or activity or one or more agents that it targets. An antagonist may be direct (in which case it exerts its influence directly upon its target) or indirect (in which case it exerts its influence by other than binding to its target; e.g., by interacting with a regulator of the target, for example so that level or activity of the target is altered). In some embodiments, an antagonist may be a receptor antagonist, e.g., a receptor ligand or drug that blocks or dampens a biological response by binding to and blocking a receptor rather than activating it like an agonist. In certain embodiments, compounds of Formula (I) are antagonists of HCN (e.g., HCN1). In certain embodiments, compounds of Formula (II) are antagonists of HCN (e.g., HCN1). In certain embodiments, compounds of Formula (I) inhibit HCN (e.g., HCN1) channel gating. In certain embodiments, compounds of Formula (II) inhibit HCN (e.g., HCN1) channel gating.

The term "agonist" refers to an agent that (i) increases or induces one or more effects of another agent; and/or (ii) increases or induces one or more biological events. In some embodiments, an agonist may increase level and/or activity or one or more agents that it targets. In various embodiments, agonists may be or include agents of various chemical class including, for example, small molecules, polypeptides, nucleic acids, carbohydrates, lipids, metals, and/or other entity that shows the relevant agonistic activity. An agonist may be direct (in which case it exerts its influence directly upon its target) or indirect (in which case it exerts its influence by other than binding to its target; e.g., by interacting with a regulator of the target, for example so that level or activity of the target is altered). A partial agonist can act as a competitive antagonist in the presence of a full agonist, as it competes with the full agonist to interact with its target and/or a regulator thereof, thereby producing (i) a decrease in one or more effects of another agent, and/or (ii) a decrease in one or more biological events, as compared to that observed with the full agonist alone.

The term "inverse agonist" refers to an agent that binds to the same receptor as an agonist but induces a pharmacological response opposite to that agonist. A neutral antagonist has no activity in the absence of an agonist or inverse agonist but can block the activity of either. Inverse agonists have opposite actions to those of agonists but the effects of both of these can be blocked by antagonists. An agonist increases the activity of a receptor above its basal level, whereas an inverse agonist decreases the activity below the basal level. In certain embodiments, compounds of Formula (I) are inverse agonists of HCN (e.g., HCN1). In certain embodiments, compounds of Formula (II) are inverse agonists of HCN (e.g., HCN1).

The term "inhibit" or "inhibition" in the context of modulating level (e.g., expression and/or activity) of a target (e.g., HCN1) is not limited to only total inhibition. Thus, in some embodiments, partial inhibition or relative reduction is included within the scope of the term "inhibition." In some embodiments, the term refers to a reduction of the level (e.g., expression, and/or activity) of a target (e.g., HCN1) to a level that is reproducibly and/or statistically significantly lower than an initial or other appropriate reference level, which may, for example, be a baseline level of a target. In some embodiments, the term refers to a reduction of the level (e.g., expression and/or activity) of a target to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of a target.

As used herein, the term "inhibitor" refers to an agent whose presence or level correlates with decreased level or activity of a target to be modulated. In some embodiments, an inhibitor may act directly (in which case it exerts its influence directly upon its target, for example by binding to the target); in some embodiments, an inhibitor may act indirectly (in which case it exerts its influence by interacting with and/or otherwise altering a regulator of a target, so that level and/or activity of the target is reduced). In some embodiments, an inhibitor is one whose presence or level correlates with a target level or activity that is reduced relative to a particular reference level or activity (e.g., that observed under appropriate reference conditions, such as presence of a known inhibitor, or absence of the inhibitor as disclosed herein, etc.). In certain embodiments, compounds of Formula (I) are inhibitors of HCN (e.g., HCN1). In certain embodiments, compounds of Formula (II) are inhibitors of HCN (e.g., HCN1).

The term "salt" and "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in J. Pharmaceutical Sciences (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions, such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as rodents (e.g., mice, rats), guinea pigs, cattle, pigs, horses, sheep, goats, cats, and/or dogs. The non-human animal may be male or female and at any stage of development. A non-human animal may be a transgenic animal.

As used herein, "chronic pain" means pain that lasts longer than normal course of pain for a particular injury. Chronic pain intensity may vary from mild to high. Chronic pain includes neuropathic pain, which refers to a chronic pain of nerve origin.

"Disease," "disorder," and "condition" are used interchangeably herein.

As used herein, and unless otherwise specified, the terms "treat," "treating," and "treatment" contemplate an action that occurs while a subject is suffering from the specified disease, disorder, or condition, which reduces the severity of the disease, disorder, or condition, or retards or slows the progression of the disease, disorder, or condition ("therapeutic treatment" or "therapeutically treating"), and also contemplates an action that occurs before a subject begins to suffer from the specified disease, disorder, or condition, and which inhibits or reduces the severity of the disease, disorder, or condition ("prophylactic treatment" or "prophylactically treating").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. For example, the effective amount of a compound with anti-proliferative activity is the amount that results in a sufficient concentration to inhibit the proliferation of cells. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder, or condition, or to delay or minimize one or more symptoms associated with the disease, disorder, or condition. A therapeutically effective amount of a compound means an amount of therapeutic agent, alone or in combination with other therapies, which provides a therapeutic benefit in the treatment of the disease, disorder, or condition. The term "therapeutically effective amount" can encompass an amount that improves overall therapy, reduces or avoids symptoms or causes of the disease, disorder, or condition, or enhances the therapeutic efficacy of another therapeutic agent.

As used herein, and unless otherwise specified, a "prophylactically effective amount" of a compound is an amount sufficient to prevent a disease, disorder, or condition, or one or more symptoms associated with the disease, disorder, or condition, or prevent its recurrence. A prophylactically effective amount of a compound means an amount of a therapeutic agent, alone or in combination with other agents, which provides a prophylactic benefit in the prevention of the disease, disorder, or condition. The term "prophylactically effective amount" can encompass an amount that improves overall prophylaxis or enhances the prophylactic efficacy of another prophylactic agent.

As used herein, use of the phrase "at least one instance" refers to 1, 2, 3, 4, or more instances, but also encompasses a range, for example, from 1 to 4, from 1 to 3, from 1 to 2, from 2 to 4, from 2 to 3, or from 3 to 4 instances, inclusive.

BRIEF DESCRIPTION OF THE DRAWINGS

FIG. 1 shows the structure of HCN1 and alkylphenol binding sites and lipid ordering in ion channels.

four-fold symmetric arrangement of the subunits is seen clearly in FIG. 1B where one of the HCN1 subunits is ringed in a dashed line. In FIG. 1B, the sequences that form the radially-arrayed voltage-sensing paddle motifs are labelled S1-S4 in the lower right subunit. The horizontal gray bars in FIG. 1A represent approximate boundaries of the membrane bilayer. "Out" and "in" indicate the orientation of the tetrameric channel in the bilayer.

In FIG. 1H, the spheres intercalated between each voltage-sensing paddle indicates the hypothetical location of anchors (not to scale) with the tether and pharmacophore intercalated into the "targeting groove" between the S1-S4 paddles and going perpendicularly into the page.

FIG. 2 shows a sequence alignment for HCN1-4 (FIG. 2A) and a cryo-EM structure (FIG. 2B) of sequences corresponding to the minimal alkylbenzene-sensitive HCN1 channel core HCN1-ΔNvΔC.

FIG. 22A and FIG. 22B are plots showing $\Delta V_{1/2}$ as a function of concentration of iso-propyl and tert-butyl phenols and cyclohexanols. FIG. 22C, FIG. 22D, and FIG. 22E are plots showing $\Delta V_{1/2}$ as a function of concentration of 2,6-DIPCH, 2,6-DTBCH, and 2,6-DIPP in the presence of 3 µM 2,6-DTBP. FIG. 22F is a graph showing association constants determined from the fits of the common site model with N=4 (as per FIG. 22A-E) transformed to free energy terms according to -(RT)LnK.

DETAILED DESCRIPTION OF CERTAIN EMBODIMENTS OF THE INVENTION

HCN1 channels are assembled as tetramers in a cruciform arrangement with the four voltage-sensing "paddles" (formed from S1-S4) arranged around a central complex (formed from the S5-S6 sequences) (FIG. 1). The ion conducting pore lies at the central axis of symmetry. While there is an intriguing difference between HCN and Kv channels that may relate to the inverted voltage dependence of gating (HCN subunits are four spokes around an axis—see coding in the lower panel of FIG. 1B, whereas in Kv channels the voltage sensor of one subunit rests on the S5-S6 of its neighbor—not shown), in both molecules there are substantial voids between each of the voltage sensors. These voids leave an aspect of each S5-S6 motif exposed to membrane lipid (FIG. 1B, 1C). Indeed, at adequate resolution, lipids in these "voids" are visualized in solved structures (zig zag grey lines in FIGS. 1C and 1D).

Figure 1A:
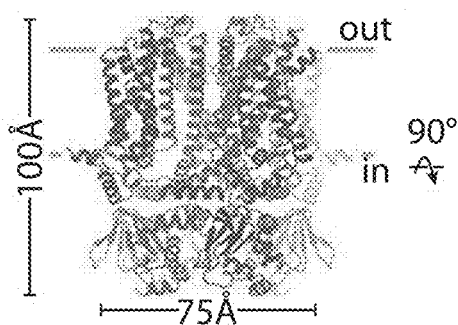
FIG. 1A and FIG. 1B: Cryo-EM structure of the HCN1 tetramer in the ligand-free state, viewed parallel to the membrane (FIG. 1A) or from the extracellular side (FIG. 1B). The "non-swapped"
Figure 1B:
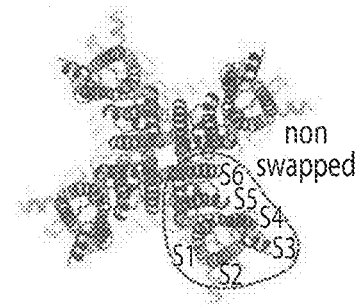
Figure 1C:
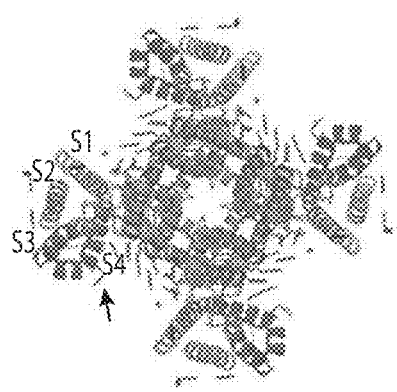
FIG. 1C and FIG. 1D: Structure of a Kv channel crystallized in the presence of lipid as viewed from the extracellular face (left) and the side (right). For clarity, on the right, only a single S1-S4 voltage-sensing domain and its interface with the lipid-facing shell of the pore (right) is shown. In both FIG. 1C and FIG. 1D, co-crystalized lipids are resolved and are depicted as zig-zag lines in the voids between adjacent voltage-sensing paddles (in FIG. 1C) and adjacent to the paddle and the membrane-facing surface of the pore (in FIG. 1C and FIG. 1D). The arrow identifies outer S4 Arg residues projecting towards the lipid membrane.
Figure 1D:
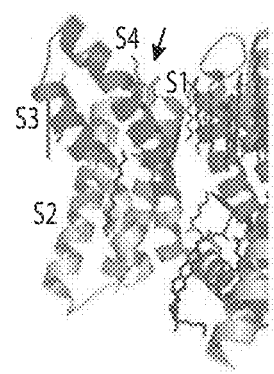
Figure 1E:
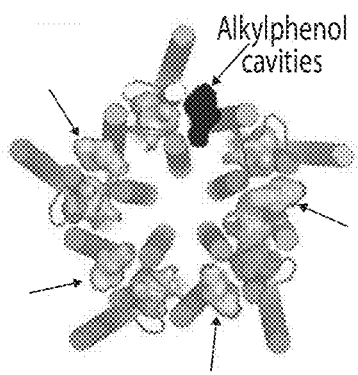
FIG. 1E and FIG. 1F: Molecular surface of one of the five general-anesthetic intrasubunit cavities identified in GLIC (Gloeobacter Ligand-gated Ion Channel, a bacterial homologue of the pentameric ligand gated ion channels that are targets for alkylphenols; Bocquet et al., Nature 2007 445, 116-119; Nury et al., Nature 2011, 469, 428-431) is shown in black, the locations of all five of the radially-symmetrical cavities are shown by the arrows. The unlabeled light grey molecular surface volumes flag the location of the neighboring inter-subunit cavities and, on the lower right, one of the communication tunnels that link the sites (FIG. 1E). A schematic representation of the helical arrangement of a single subunit of a pentameric ligand-gated channel with an alkylphenol docked within the intrasubunit cavity (viewed from outside) (FIG. 1F).
Figure 1F:
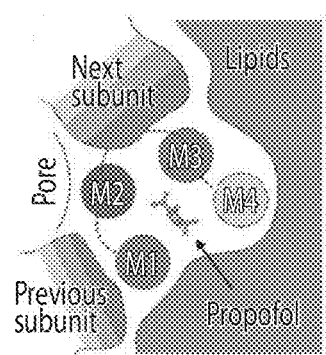
Figure 1G:
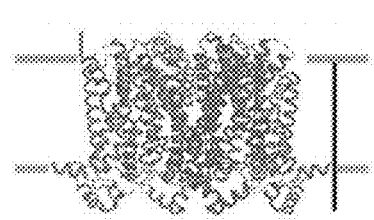
FIG. 1G and FIG. 1H: Anticipated structure of the minimal alkylphenol sensitive HCN1 channel, HCN1-ΔNvΔC. As in FIG. 1A, the horizontal grey bars in FIG. 1G indicate the approximate boundaries of the membrane bilayer. The left scale bar on FIG. 1G represents the distance from the extracellular apex of the channel to the membrane surface. This distance is ~14 Å. The right scale bar on FIG. 1G represents the distance from the extracellular surface of the membrane to the most internal aspects of the coupling loops that link the transmembrane helices. This distance is ~60 Å and represents the maximal theoretical orthoganol reach required for the tethered pharmacophore and, hence, of the tether.
Figure 1H:
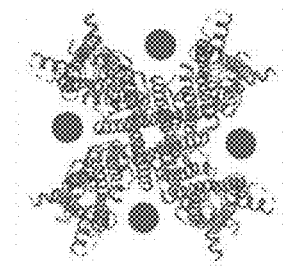
Figure 2A:
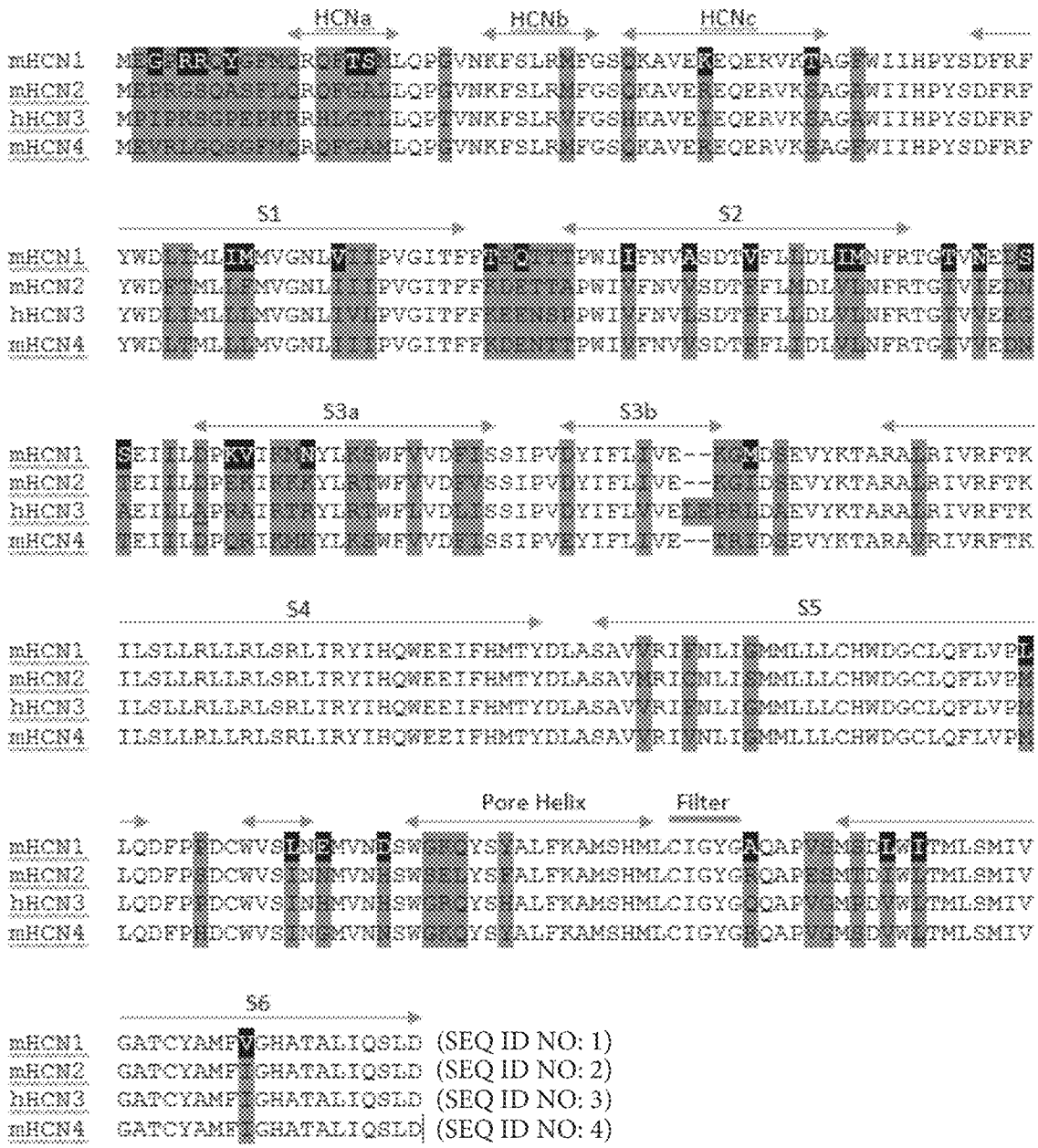
FIG. 2A: Within this core structure, there are 34 residues that are unique to mHCN1 with respect to mHCN2, hHCN3, and mHCN4 (indicated by residues in white text on black highlights) and 50 residues that are divergent from at least one other isoform (indicated by residues highlighted in grey). Residues that are not highlighted exhibit four-fold conservation across the indicated isoforms. Alignments were obtained using Clustal Omega(1.2.4) (www.ebi.ac.uk/Tools/msa/clustalo/) for mouse (m)HCN1 (O88704.1), mHCN2 (O88703.1), human (h)HCN3 (Q9P1Z3.2), and mHCN4 (O70507.2).
Figure 2B:
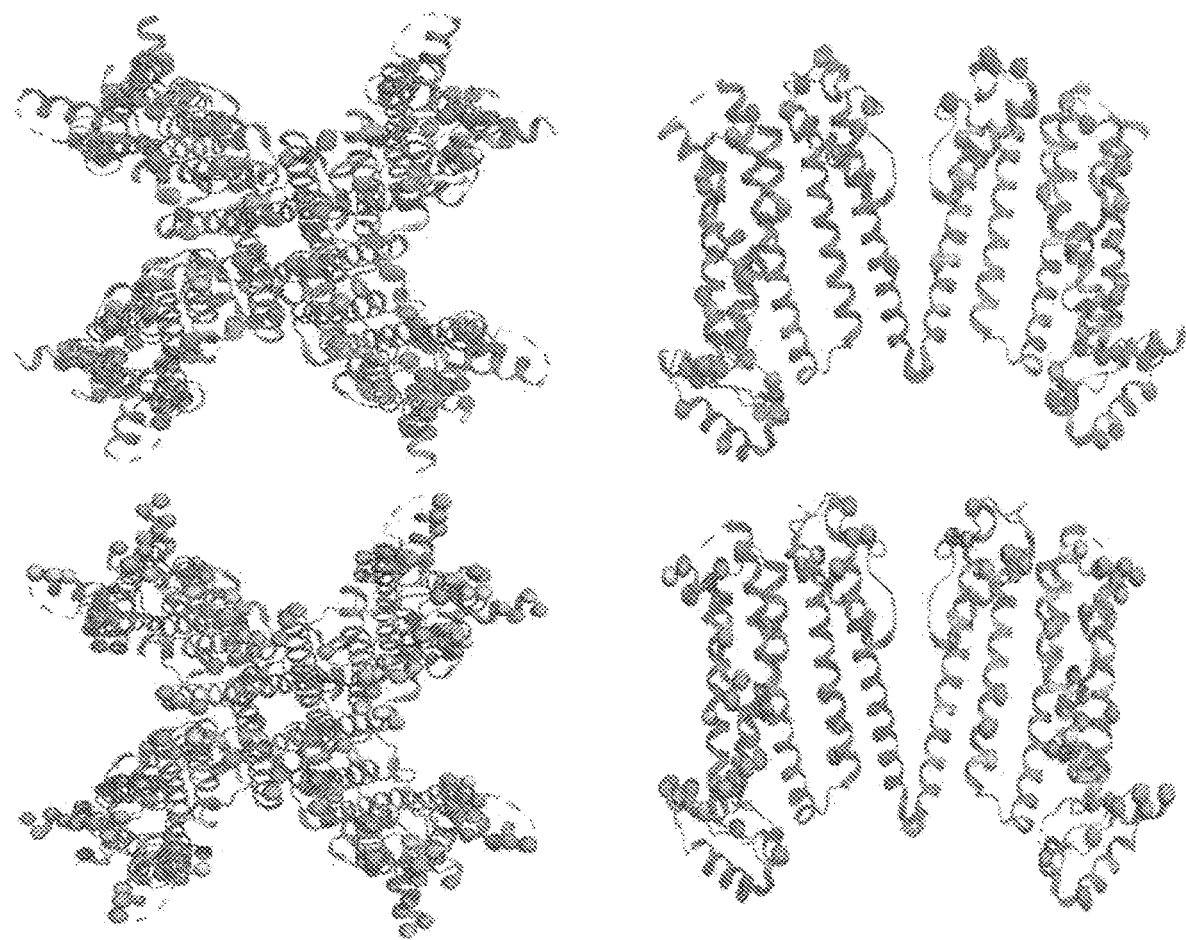
FIG. 2B: Top-down view of the tetramer of the core channel as predicted from the cryo-EM structure of the hHCN1 tetramer (left panels) and side-on view with front and back subunits removed for clarity (right panels). Note, the mouse and human HCN1 sequences are identical in the region defined by mHCN1-ΔNvΔC. HCN1 unique residues are shown as spheres on the upper row; residues that are common to HCN1 and at least one other of the HCN1 sequences (but not all) are shown as spheres on the lower row. The structure is based on atomic coordinates of HCN1 in the cAMP unbound state from Lee & MacKinnon 2017 (Cell, 168(1-2) 111-120) and deposited in the protein data bank (uniprot.org) under accession code 5U6O.

Crystallography shows propofol docks in cavities in $GABA_A$-Rs (FIGS. 1E and 1F) where it likely displaces either native acyl chains or water. Mass tagging with a photoactivatable alkylphenol, coupled with molecular dynamics modeling, reveals the alkylphenols intercalate al-β3 subunits in these receptors. Deletion analysis has demonstrated that only the core of HCN1 is required for the channel to exhibit full alkylphenol sensitivity; much of the cytoplasmic N-terminus and all the cytoplasmic C-terminus can be removed without compromising drug function. The minimal alkylphenol-sensitive channel omits ~64% of the full-length human HCN1 sequence (FIG. 1G and FIG. 1H). FIG. 2A shows the alignment of HCN1-4 across the region corresponding to the alkylphenol-sensitive core. FIG. 2B shows isoform divergence mapped onto the cryo-EM structure.

FIG. 1G and FIG. 1H show the minimal channel (HCN1-ΔNvΔC) along with the approximate locations of the membrane surfaces (horizontal grey bars) and scale bars to illustrate the approximate distance from the apex of the extracellular loops to external face of the membrane (vertical grey bar) and from there to the inner most aspect of the loops between transmembrane structures (vertical black bar).

Kinetic modeling and other studies indicate 2,6-DTBP modifies HCN1 gating by discriminating between the closed and open conformations of the pore and does so by interacting with a site it accesses via the lipid phase. The presence of vertical lipid-facing voids running the length of the channel, with an aspect of these voids being the external aspect (with respect to the central ion conduction path) of the S5-S6 pore motif is consistent with a location somewhere along this surface being the location of the alkylphenol site. This description of a prototypical alkylphenol binding site, as per GABAA receptors, is consistent with the presumptive location as identified in HCN1.

That the lipid-filled vertical voids run the length of the channel from the external face to the cytoplasm provide evidence that a physical channel (a "targeting groove") for tethered pharmacophore delivery exists and its geometry is consistent with delivery of the pharmacophore regardless the distance between the external surface and the alkylphenol site.

Compounds

Provided herein are novel compounds (e.g., compounds of Formula (I) and Formula (II)) that modulate HCN channels, intermembrane proteins that serve as non-selective voltage-gated cation channels in the plasma membranes of excitable cells including those of heart, central (CNS) and peripheral (PNS) nervous system. In certain embodiments, the compounds are selective antagonists and/or inhibitors of the HCN isoform, HCN1, and may be useful in the treatment of pain (e.g., chronic pain). The compounds may be provided for use in any composition, kit, or method described herein as the compound or a pharmaceutically acceptable salt.

In certain embodiments, the compounds have a structure (e.g., FIG. 3) comprising an anchor moiety ("T") that may not cross the lipid bilayer of the cell membrane, thus restricting the anchor end of the compound to the extracellular space. A linker ("$L^1$-$L^2$") attached to the anchor on one end and the pharmacophore on the other serves to orient the compound and span the cell membrane, allowing the pharmacophore to reach its effector site with an orientation that permits functionally-effective binding (e.g., with HCN1 to inhibit gating).

Provided are compounds of Formula (I):

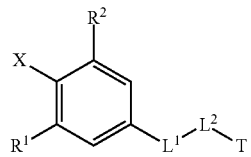
(I)

and pharmaceutically acceptable salts thereof;
wherein:
$R^1$ is unsubstituted alkyl;
$R^2$ is unsubstituted alkyl;
X is halogen, —OP, —N($R^A$)$_2$, —NR$^A$N($R^A$)$_2$, —SP, or —NCO;
P is hydrogen, an oxygen protecting group, a sulfur protecting group, or substituted or unsubstituted heterocyclyl;
$L^1$ is —(C=O)—, —CH$_2$—, —CH=CH—, —C≡C—, —O—, —S—, or —NR$^A$—;
$L^2$ is substituted or unsubstituted alkylene, substituted or unsubstituted alkenylene, substituted or unsubstituted alkynylene, substituted or unsubstituted heteroalkylene, substituted or unsubstituted heteroalkenylene, or substituted or unsubstituted heteroalkynylene, wherein $L^2$ comprises a chain of at least 8 continuous non-hydrogen atoms from its point of attachment to $L^1$ to its point of attachment to T;
T is substituted alkyl, substituted or unsubstituted alkenyl, substituted or unsubstituted alkynyl, substituted or unsubstituted heteroalkyl, —OR$^C$, —N($R^A$)$_2$, —SR$^A$, —CO$_2$H, halogen, —OS(O$_2$)R$^B$, —O(C=O)R$^C$, —(C=O)OR$^C$, —O(C=O)OR$^C$, —(C=O)N($R^A$)$_2$, —O(C=O)N($R^A$)$_2$, —NR$^A$(C=O)N($R^A$)$_2$, —CN, —CHO, —N$_3$, —N=C=S,

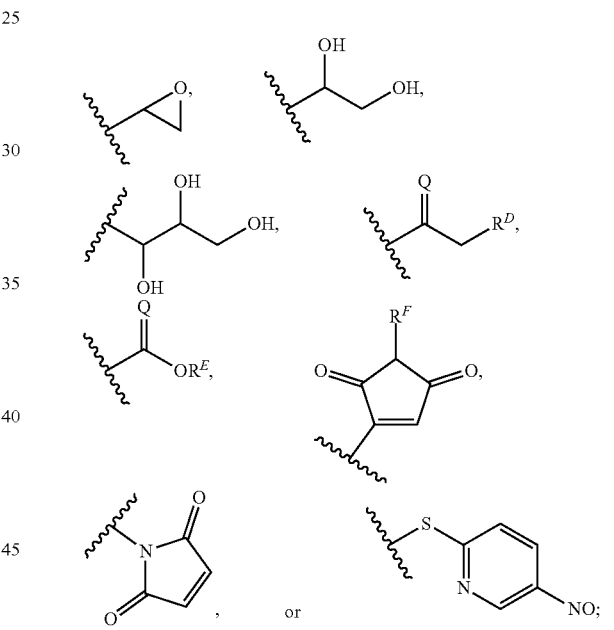

Q is S or O;
each $R^A$ is independently hydrogen, substituted or unsubstituted alkyl, substituted or unsubstituted heteroalkyl, substituted or unsubstituted acyl, substituted or unsubstituted heterocyclyl, a nitrogen protecting group, or a sulfur protecting group;
$R^B$ is substituted or unsubstituted alkyl or substituted or unsubstituted aryl;
$R^C$ is substituted or unsubstituted alkyl, substituted or unsubstituted aryl, substituted or unsubstituted heterocyclyl, substituted or unsubstituted heteroaryl, or an oxygen protecting group;
$R^D$ is halogen or —OS(O$_2$)R$^B$;
$R^E$ is hydrogen, substituted or unsubstituted alkyl, substituted or unsubstituted carbocyclyl, substituted or unsubstituted heterocyclyl, substituted or unsubstituted aryl, substituted or unsubstituted heteroaryl, or an oxygen protecting group; and $R^F$ is hydrogen, substituted or unsubstituted alkyl, or a nitrogen protecting group;
provided that the compound is not:

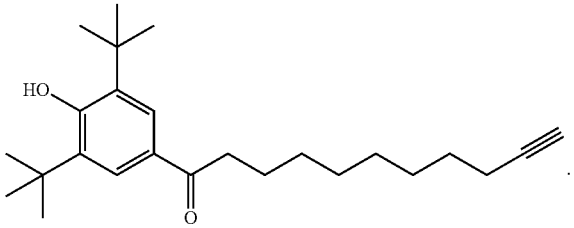 [SMILES: C#CCCCCCCCCC(=O)c1cc(C(C)(C)C)c(O)c(C(C)(C)C)c1]

Groups $R^1$ and $R^2$

As described herein, $R^1$ is unsubstituted alkyl. In certain embodiments, $R^1$ is unsubstituted $C_{1-6}$ alkyl. In certain embodiments, $R^1$ is unsubstituted $C_{1-4}$ alkyl. In certain embodiments, $R^1$ is neopentyl, tert-butyl, sec-butyl, isobutyl, n-butyl, isopropyl, n-propyl, ethyl, or methyl. In certain embodiments, $R^1$ is tert-butyl, sec-butyl, isobutyl, n-butyl, isopropyl, n-propyl, ethyl, or methyl. In certain embodiments, $R^1$ is tert-butyl, isobutyl, isopropyl, ethyl, or methyl. In certain embodiments, $R^1$ is tert-butyl, isobutyl, isopropyl, ethyl, or methyl. In certain embodiments, $R^1$ is tert-butyl, isobutyl, isopropyl, or ethyl. In certain embodiments, $R^1$ is tert-butyl, isobutyl, or isopropyl. In certain embodiments, $R^1$ is tert-butyl or isopropyl. In certain embodiments, $R^1$ is isopropyl. In certain embodiments, $R^1$ is tert-butyl.

As described herein, $R^2$ is unsubstituted alkyl. In certain embodiments, $R^2$ is unsubstituted $C_{1-6}$ alkyl. In certain embodiments, $R^2$ is unsubstituted $C_{1-4}$ alkyl. In certain embodiments, $R^2$ is neopentyl, tert-butyl, sec-butyl, isobutyl, n-butyl, isopropyl, n-propyl, ethyl, or methyl. In certain embodiments, $R^2$ is tert-butyl, sec-butyl, isobutyl, n-butyl, isopropyl, n-propyl, ethyl, or methyl. In certain embodiments, $R^2$ is tert-butyl, isobutyl, isopropyl, ethyl, or methyl. In certain embodiments, $R^2$ is tert-butyl, isobutyl, isopropyl, ethyl, or methyl. In certain embodiments, $R^2$ is tert-butyl, isobutyl, isopropyl, or ethyl. In certain embodiments, $R^2$ is tert-butyl, isobutyl, or isopropyl. In certain embodiments, $R^2$ is tert-butyl or isopropyl. In certain embodiments, $R^2$ is isopropyl. In certain embodiments, $R^2$ is tert-butyl.

In certain embodiments, $R^1$ is unsubstituted $C_{1-6}$ alkyl, and $R^2$ is unsubstituted $C_{1-6}$ alkyl. In certain embodiments, $R^1$ is unsubstituted $C_{1-4}$ alkyl, and $R^2$ is unsubstituted $C_{1-4}$ alkyl. In certain embodiments, $R^1$ is neopentyl, tert-butyl, sec-butyl, isobutyl, n-butyl, isopropyl, n-propyl, ethyl, or methyl; and $R^2$ is neopentyl, tert-butyl, sec-butyl, isobutyl, n-butyl, isopropyl, n-propyl, ethyl, or methyl. In certain embodiments, $R^1$ is tert-butyl, sec-butyl, isobutyl, n-butyl, isopropyl, n-propyl, ethyl, or methyl; and $R^2$ is tert-butyl, sec-butyl, isobutyl, n-butyl, isopropyl, n-propyl, ethyl, or methyl. In certain embodiments, $R^1$ is tert-butyl, isobutyl, isopropyl, ethyl, or methyl; and $R^2$ is tert-butyl, isobutyl, isopropyl, ethyl, or methyl. In certain embodiments, $R^1$ is tert-butyl, isobutyl, isopropyl, ethyl, or methyl; and $R^2$ is tert-butyl, isobutyl, isopropyl, ethyl, or methyl. In certain embodiments, $R^1$ is tert-butyl, isobutyl, isopropyl, or ethyl; and $R^2$ is tert-butyl, isobutyl, isopropyl, or ethyl. In certain embodiments, $R^1$ is tert-butyl, isobutyl, isopropyl; and $R^2$ is tert-butyl, isobutyl, or isopropyl. In certain embodiments, $R^1$ is tert-butyl or isopropyl; and $R^2$ is Cert-butyl or isopropyl. In certain embodiments, $R^1$ is isopropyl; and $R^2$ is isopropyl. In certain embodiments, $R^1$ is isopropyl; and $R^2$ is tert-butyl. In certain embodiments, $R^1$ is tert-butyl; and $R^2$ is isopropyl. In certain embodiments, $R^1$ is tert-butyl, and $R^2$ is tert-butyl.

Group X

As described herein, X is halogen, —OP, —N($R^A$)$_2$, —NR$^A$N($R^A$)$_2$, —SP, or —NCO; P is hydrogen, an oxygen protecting group, a sulfur protecting group, or substituted or unsubstituted heterocyclyl; and each $R^A$ is independently hydrogen, substituted or unsubstituted alkyl, substituted or unsubstituted heteroalkyl, substituted or unsubstituted acyl, substituted or unsubstituted heterocyclyl, a nitrogen protecting group, or a sulfur protecting group In certain embodiments, X is halogen, —OP, —N($R^A$)$_2$, —SP, or —NCO; P is hydrogen, an oxygen protecting group, or a sulfur protecting group; and each $R^A$ is independently hydrogen, substituted or unsubstituted alkyl, substituted or unsubstituted heteroalkyl, substituted or unsubstituted acyl, or a nitrogen protecting group. In certain embodiments, X is halogen, —OP, —SP, or —NCO; and P is hydrogen, an oxygen protecting group, or a sulfur protecting group. In certain embodiments, X is halogen, —OH, —SH, or —NCO. In certain embodiments, X is —F, —Cl, —Br, —I, —OH, —SH, or —NCO. In certain embodiments, X is —F, —Cl, —OH, —SH, or —NCO. In certain embodiments, X is —F, —OH, —SH, or —NCO. In certain embodiments, X is —F, —OH, or —SH. In certain embodiments, X is —OH or —SH. In certain embodiments, X is —F or —OH. In certain embodiments, X is —F. In certain embodiments, X is —Cl. In certain embodiments, X is —Br. In certain embodiments, X is —I. In certain embodiments, X is —OH. In certain embodiments, X is —OP, wherein P is an oxygen protecting group. In certain embodiments, X is —SH. In certain embodiments, X is —SP, wherein P is a sulfur protecting group. In certain embodiments, X is —NCO.

Group $L^1$

As described herein, $L^1$ is —(C=O)—, —CH$_2$—, —CH=CH—, —C≡C—, —O—, —S—, or —NR$^A$—. In certain embodiments, $L^1$ is —(C=O)—, —CH=CH—, or —C≡C—. In certain embodiments, $L^1$ is —CH$_2$—. In certain embodiments, $L^1$ is —CH=CH—. In certain embodiments, $L^1$ is —C≡C—. In certain embodiments, $L^1$ is —O—. In certain embodiments, $L^1$ is —S—. In certain embodiments, $L^1$ is —NR$^A$—, wherein $R^A$ is hydrogen, substituted or unsubstituted alkyl, substituted or unsubstituted heteroalkyl, or a nitrogen protecting group. In certain embodiments, $L^1$ is —(C=O)—.

Group $L^2$

As described herein, $L^2$ is substituted or unsubstituted alkylene, substituted or unsubstituted alkenylene, substituted or unsubstituted alkynylene, substituted or unsubstituted heteroalkylene, substituted or unsubstituted heteroalkenylene, or substituted or unsubstituted heteroalkynylene, wherein $L^2$ comprises a chain of at least 8 continuous non-hydrogen atoms from its point of attachment to $L^1$ to its point of attachment to T. In certain embodiments, $L^2$ is substituted or unsubstituted alkylene, substituted or unsubstituted alkenylene, substituted or unsubstituted heteroalkylene, or substituted or unsubstituted heteroalkenylene, wherein $L^2$ comprises a chain of at least 8 continuous non-hydrogen atoms from its point of attachment to $L^1$ to its point of attachment to T. In certain embodiments, $L^2$ is substituted or unsubstituted $C_{8-30}$ alkylene; substituted or unsubstituted $C_{8-30}$ alkenylene; substituted or unsubstituted $C_{4-30}$ heteroalkylene; or substituted or unsubstituted $C_{4-30}$ heteroalkenylene. In certain embodiments, $L^2$ is substituted or unsubstituted $C_{8-20}$ alkylene; substituted or unsubstituted $C_{8-20}$ alkenylene; substituted or unsubstituted $C_{4-20}$ heteroalkylene; or substituted or unsubstituted $C_{4-20}$ heteroalkenylene. In certain embodiments, $L^2$ is substituted or unsubstituted $C_{15-20}$ alkylene; substituted or unsubstituted $C_{15-20}$ alkenylene; substituted or unsubstituted $C_{8-20}$ heteroalkylene; or substituted or unsubstituted $C_{8-20}$ heteroalkenylene. In certain embodiments, $L^2$ is substituted or unsubstituted $C_{8-16}$ alkylene; substituted or unsubstituted $C_{8-16}$ alkenylene; substituted or unsubstituted $C_{4-16}$ heteroalkylene; or substituted or unsubstituted $C_{4-16}$ heteroalkenylene. In certain embodiments, $L^2$ is substituted or unsubstituted $C_{8-12}$ alkylene; substituted or unsubstituted $C_{8-12}$ alkenylene; substituted or unsubstituted $C_{4-12}$ heteroalkylene; or substituted or unsubstituted $C_{4-12}$ heteroalkenylene.

In certain embodiments, $L^2$ is substituted or unsubstituted $C_{8-30}$ alkylene; or substituted or unsubstituted $C_{8-30}$ alkenylene. In certain embodiments, $L^2$ is substituted $C_{8-30}$ alkylene; or substituted $C_{8-30}$ alkenylene. In certain embodiments, $L^2$ is unsubstituted $C_{8-30}$ alkylene; or unsubstituted $C_{8-30}$ alkenylene. In certain embodiments, $L^2$ is substituted $C_{8-20}$ alkylene; or substituted $C_{8-20}$ alkenylene. In certain embodiments, $L^2$ is unsubstituted $C_{8-20}$ alkylene; or unsubstituted $C_{8-20}$ alkenylene. In certain embodiments, $L^2$ is substituted $C_{8-16}$ alkylene; or substituted $C_{8-16}$ alkenylene. In certain embodiments, $L^2$ is unsubstituted $C_{8-16}$ alkylene; or unsubstituted $C_{8-16}$ alkenylene. In certain embodiments, $L^2$ is substituted $C_{8-12}$ alkylene; or substituted $C_{8-12}$ alkenylene. In certain embodiments, $L^2$ is unsubstituted $C_{8-12}$ alkylene; or unsubstituted $C_{8-12}$ alkenylene.

In certain embodiments, $L^2$ is substituted or unsubstituted $C_{8-30}$ alkylene; or substituted or unsubstituted $C_{4-30}$ heteroalkylene. In certain embodiments, $L^2$ is substituted $C_{8-30}$ alkylene; or substituted $C_{4-30}$ heteroalkylene. In certain embodiments, $L^2$ is unsubstituted $C_{8-30}$ alkylene; or unsubstituted $C_{4-30}$ heteroalkylene. In certain embodiments, $L^2$ is substituted $C_{8-20}$ alkylene; or substituted $C_{4-20}$ heteroalkylene. In certain embodiments, $L^2$ is unsubstituted $C_{8-20}$ alkylene; or unsubstituted $C_{4-20}$ heteroalkylene. In certain embodiments, $L^2$ is substituted $C_{8-16}$ alkylene; or substituted $C_{4-16}$ heteroalkylene. In certain embodiments, $L^2$ is unsubstituted $C_{8-16}$ alkylene; or unsubstituted $C_{4-16}$ heteroalkylene. In certain embodiments, $L^2$ is substituted $C_{8-12}$ alkylene; or substituted $C_{4-12}$ heteroalkylene. In certain embodiments, $L^2$ is unsubstituted $C_{8-12}$ alkylene; or unsubstituted $C_{4-12}$ heteroalkylene.

In certain embodiments, $L^2$ is substituted or unsubstituted alkylene. In certain embodiments, $L^2$ is substituted or unsubstituted $C_{8-30}$ alkylene. In certain embodiments, $L^2$ is substituted $C_{8-30}$ alkylene. In certain embodiments, $L^2$ is unsubstituted $C_{8-30}$ alkylene. In certain embodiments, $L^2$ is substituted $C_{8-20}$ alkylene. In certain embodiments, $L^2$ is unsubstituted $C_{8-20}$ alkylene. In certain embodiments, $L^2$ is substituted $C_{8-16}$ alkylene. In certain embodiments, $L^2$ is unsubstituted $C_{8-16}$ alkylene. In certain embodiments, $L^2$ is substituted $C_{8-12}$ alkylene. In certain embodiments, $L^2$ is unsubstituted $C_{8-12}$ alkylene.

In certain embodiments, $L^2$ is substituted or unsubstituted alkenylene. In certain embodiments, $L^2$ is substituted or unsubstituted $C_{8-30}$ alkenylene. In certain embodiments, $L^2$ is substituted $C_{8-30}$ alkenylene. In certain embodiments, $L^2$ is unsubstituted $C_{8-30}$ alkenylene. In certain embodiments, $L^2$ is substituted $C_{8-20}$ alkenylene. In certain embodiments, $L^2$ is unsubstituted $C_{8-20}$ alkenylene. In certain embodiments, $L^2$ is substituted $C_{8-16}$ alkenylene. In certain embodiments, $L^2$ is unsubstituted $C_{8-16}$ alkenylene. In certain embodiments, $L^2$ is substituted $C_{8-12}$ alkenylene. In certain embodiments, $L^2$ is unsubstituted $C_{8-12}$ alkenylene.

In certain embodiments, $L^2$ is substituted or unsubstituted heteroalkylene. In certain embodiments, $L^2$ is substituted or unsubstituted $C_{4-30}$ heteroalkylene. In certain embodiments, $L^2$ is substituted $C_{4-30}$ heteroalkylene. In certain embodiments, $L^2$ is unsubstituted $C_{4-30}$ heteroalkylene. In certain embodiments, $L^2$ is substituted $C_{4-20}$ heteroalkylene. In certain embodiments, $L^2$ is unsubstituted $C_{4-20}$ heteroalkylene. In certain embodiments, $L^2$ is substituted $C_{4-16}$ heteroalkylene. In certain embodiments, $L^2$ is unsubstituted $C_{4-16}$ heteroalkylene. In certain embodiments, $L^2$ is substituted $C_{4-12}$ heteroalkylene. In certain embodiments, $L^2$ is unsubstituted $C_{4-12}$ heteroalkylene.

In certain embodiments, $L^2$ comprises a chain of at least 8 continuous non-hydrogen atoms from its point of attachment to $L^1$ to its point of attachment to T. In certain embodiments, $L^2$ comprises a chain of at least 9, 10, 11, 12, 13, 14, 15, 16, 17, 18, 19, 20, 21, 22, 23, 24, 25, 26, 27, 28, 29, or 30 continuous non-hydrogen atoms from its point of attachment to $L^1$ to its point of attachment to T. In certain embodiments, $L^2$ comprises a chain of 8-50 continuous non-hydrogen atoms from its point of attachment to $L^1$ to its point of attachment to T. In certain embodiments, $L^2$ comprises a chain of 8-40 continuous non-hydrogen atoms from its point of attachment to $L^1$ to its point of attachment to T. In certain embodiments, $L^2$ comprises a chain of 8-30 continuous non-hydrogen atoms from its point of attachment to $L^1$ to its point of attachment to T. In certain embodiments, $L^2$ comprises a chain of 8-25 continuous non-hydrogen atoms from its point of attachment to $L^1$ to its point of attachment to T. In certain embodiments, $L^2$ comprises a chain of 8-20 continuous non-hydrogen atoms from its point of attachment to $L^1$ to its point of attachment to T. In certain embodiments, $L^2$ comprises a chain of 8-16 continuous non-hydrogen atoms from its point of attachment to $L^1$ to its point of attachment to T. In certain embodiments, $L^2$ comprises a chain of 12-30 continuous non-hydrogen atoms from its point of attachment to $L^1$ to its point of attachment to T. In certain embodiments, $L^2$ comprises a chain of 12-25 continuous non-hydrogen atoms from its point of attachment to $L^1$ to its point of attachment to T. In certain embodiments, $L^2$ comprises a chain of 16-25 continuous non-hydrogen atoms from its point of attachment to $L^1$ to its point of attachment to T. In certain embodiments, $L^2$ comprises a chain of 16-20 continuous non-hydrogen atoms from its point of attachment to $L^1$ to its point of attachment to T.

Group T

The anchor moiety ("T") serves different functions. In some embodiments, the anchor moiety restricts the compound to the periphery and the extracellular space. In some embodiments, the anchor serves to target the pharmacaphore to peripheral sensory neurons (e.g., peripheral HCN1 channels). In some embodiments, the anchor moiety is a reactive group (e.g., electrophilic) that may function to facilitate conversion of the anchor moiety to another anchor moiety.

As described herein, T is substituted alkyl, substituted or unsubstituted alkenyl, substituted or unsubstituted alkynyl, substituted or unsubstituted heteroalkyl, —OR$^C$, —N(R$^A$)$_2$, —SR$^A$, —CO$_2$H, halogen, —OS(O$_2$)R$^B$, —O(C=O)R$^C$, —(C=O)OR$^C$, —O(C=O)OR$^C$, —(C=O)N(R$^A$)$_2$, —O(C=O)N(R$^A$)$_2$, —NR$^A$(C=O)N(R$^A$)$_2$, —CN, —CHO, —N$_3$, —N=C=S,

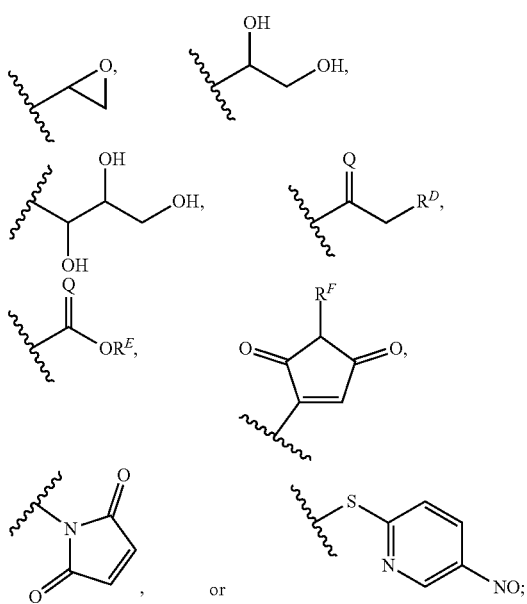

Q is S or O; each $R^A$ is independently hydrogen, substituted or unsubstituted alkyl, substituted or unsubstituted heteroalkyl, substituted or unsubstituted acyl, substituted or unsubstituted heterocyclyl, a nitrogen protecting group, or a sulfur protecting group; $R^B$ is substituted or unsubstituted alkyl or substituted or unsubstituted aryl; $R^C$ is substituted or unsubstituted alkyl, substituted or unsubstituted aryl, substituted or unsubstituted heterocyclyl, substituted or unsubstituted heteroaryl, or an oxygen protecting group; $R^D$ is halogen or —OS(O$_2$)$R^B$; $R^E$ is hydrogen, substituted or unsubstituted alkyl, substituted or unsubstituted carbocyclyl, substituted or unsubstituted heterocyclyl, substituted or unsubstituted aryl, substituted or unsubstituted heteroaryl, or an oxygen protecting group; and $R^F$ is hydrogen, substituted or unsubstituted alkyl, or a nitrogen protecting group.

In certain embodiments, T is substituted alkyl, substituted or unsubstituted alkenyl, substituted or unsubstituted alkynyl, substituted or unsubstituted heteroalkyl, —OH, —NH$_2$, —SH, —CO$_2$H, halogen, —OS(O$_2$)$R^B$, —O(C=O)$R^C$, —(C=O)O$R^C$, —O(C=O)O$R^C$, or

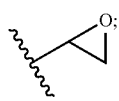

$R^B$ is substituted or unsubstituted alkyl or substituted or unsubstituted aryl; and $R^C$ is substituted or unsubstituted alkyl, substituted or unsubstituted aryl, substituted or unsubstituted heterocyclyl, or substituted or unsubstituted heteroaryl.

In certain embodiments, T is substituted alkyl, substituted or unsubstituted alkenyl, substituted or unsubstituted alkynyl, substituted or unsubstituted heteroalkyl, —OH, —NH$_2$, —SH, —CO$_2$H, halogen, or —OS(O$_2$)$R^B$; and $R^B$ is substituted or unsubstituted alkyl or substituted or unsubstituted aryl.

In certain embodiments, T is substituted alkyl, substituted or unsubstituted alkenyl, substituted or unsubstituted alkynyl, substituted or unsubstituted heteroalkyl, —OH, —NH$_2$, —SH, —CO$_2$H, halogen, or —OS(O$_2$)$R^B$; and $R^B$ is methyl, trifluoromethyl, toluyl, or p-nitrophenyl.

In certain embodiments, T is substituted alkyl, substituted or unsubstituted alkenyl, substituted or unsubstituted alkynyl, substituted or unsubstituted heteroalkyl, —OH, —NH$_2$, —SH, —CO$_2$H, or halogen.

In certain embodiments, T is substituted or unsubstituted alkenyl, substituted alkyl, substituted or unsubstituted heteroalkyl, —OH, halogen, or —(C=O)O$R^C$; and $R^C$ is substituted or unsubstituted heterocyclyl. In certain embodiments, T is substituted or unsubstituted alkenyl, substituted alkyl, —OH, halogen, or —(C=O)O$R^C$; and $R^C$ is substituted or unsubstituted heterocyclyl.

In certain embodiments, T is substituted alkyl, substituted or unsubstituted alkenyl, substituted or unsubstituted alkynyl, substituted or unsubstituted heteroalkyl, —OH, or —Cl.

In certain embodiments, T is substituted alkyl, substituted or unsubstituted alkenyl, substituted or unsubstituted heteroalkyl, —OH, or halogen. In certain embodiments, T is substituted alkyl, substituted or unsubstituted alkenyl, —OH, or halogen. In certain embodiments, T is substituted alkyl, substituted or unsubstituted alkenyl, —OH, or —Cl.

In certain embodiments, T is —Cl, —OH,

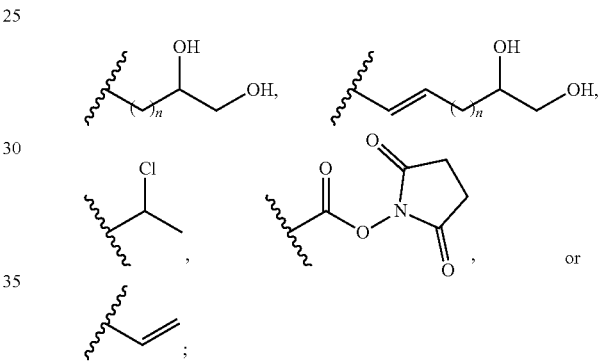

and n is an integer from 0-8. In certain embodiments, T is —Cl, —OH,

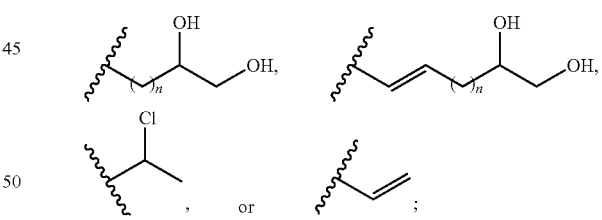

and n is an integer from 0-8. In certain embodiments, T is —Cl. In certain embodiments, T is —OH. In certain embodiments, T is

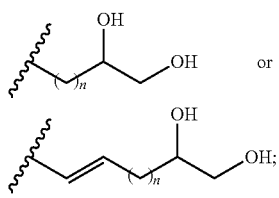

and n is an integer from 0-8. In certain embodiments, T is

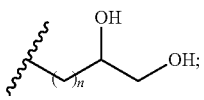

and n is an integer from 0-8. In certain embodiments, T is

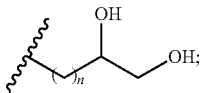

and n is 8. In certain embodiments, T is

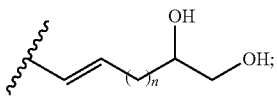

and n is an integer from 0-8. In certain embodiments, T is

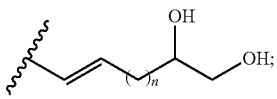

and n is 8. In certain embodiments, T is

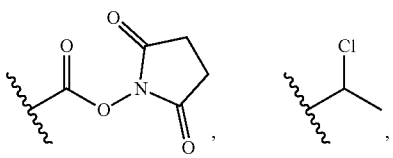

In certain embodiments, T is

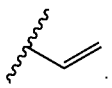

In certain embodiments, T is

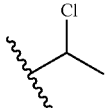

In certain embodiments, T is

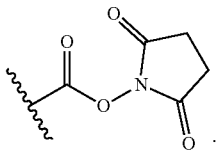 [SMILES: *C(=O)ON1C(=O)CCC1=O]

Certain Embodiments

In certain embodiments, -$L^1$-$L^2$-T is

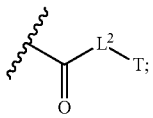

wherein $L^2$ is substituted or unsubstituted $C_{8-30}$ alkylene, substituted or unsubstituted $C_{8-30}$ alkenylene, substituted or unsubstituted $C_{4-30}$ heteroalkylene, or substituted or unsubstituted $C_{4-30}$ heteroalkenylene; and T is substituted alkyl, substituted or unsubstituted alkenyl, substituted or unsubstituted alkynyl, substituted or unsubstituted heteroalkyl, —OH, —$NH_2$, —SH, —$CO_2H$, halogen, —$OS(O_2)R^B$, or —(C=O)$OR^C$; $R^C$ is substituted or unsubstituted heterocyclyl; and $R^B$ is substituted or unsubstituted alkyl or substituted or unsubstituted aryl.

In certain embodiments, -$L^1$-$L^2$-T is

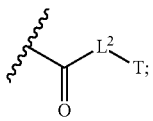

wherein $L^2$ is substituted or unsubstituted $C_{8-20}$ alkylene, substituted or unsubstituted $C_{8-20}$ alkenylene, substituted or unsubstituted $C_{4-20}$ heteroalkylene, or substituted or unsubstituted $C_{4-20}$ heteroalkenylene; and T is substituted alkyl, substituted or unsubstituted alkenyl, substituted or unsubstituted alkynyl, substituted or unsubstituted heteroalkyl, —OH, —$NH_2$, —SH, —$CO_2H$, halogen, —$OS(O_2)R^B$, or —(C=O)$OR^C$; $R^C$ is substituted or unsubstituted heterocyclyl; and $R^B$ is substituted or unsubstituted alkyl or substituted or unsubstituted aryl.

In certain embodiments, -$L^1$-$L^2$-T is

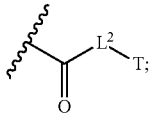

wherein $L^2$ is substituted or unsubstituted $C_{8-16}$ alkylene, substituted or unsubstituted $C_{8-16}$ alkenylene, substituted or unsubstituted $C_{4-16}$ heteroalkylene, or substituted or unsubstituted $C_{4-16}$ heteroalkenylene; and T is substituted alkyl, substituted or unsubstituted alkenyl, substituted or unsubstituted alkynyl, substituted or unsubstituted heteroalkyl, —OH, —$NH_2$, —SH, —$CO_2H$, halogen, —$OS(O_2)R^B$, or —(C═O)OR$^C$; R$^C$ is substituted or unsubstituted heterocyclyl; and R$^B$ is substituted or unsubstituted alkyl or substituted or unsubstituted aryl.

In certain embodiments, -L$^1$-L$^2$-T is

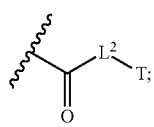

wherein L$^2$ is substituted or unsubstituted C$_{8-12}$ alkylene, substituted or unsubstituted C$_{8-12}$ alkenylene, substituted or unsubstituted C$_{4-12}$ heteroalkylene, or substituted or unsubstituted C$_{4-12}$ heteroalkenylene; and T is substituted alkyl, substituted or unsubstituted alkenyl, substituted or unsubstituted alkynyl, substituted or unsubstituted heteroalkyl, —OH, —NH$_2$, —SH, —CO$_2$H, halogen, —OS(O$_2$)R$^B$, or —(C═O)OR$^C$; R$^C$ is substituted or unsubstituted heterocyclyl; and R$^B$ is substituted or unsubstituted alkyl or substituted or unsubstituted aryl.

In certain embodiments, -L$^1$-L$^2$-T is

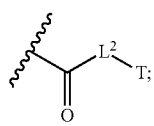

wherein L$^2$ is substituted or unsubstituted C$_{8-12}$ alkylene, or substituted or unsubstituted C$_{8-12}$ alkenylene; and T is substituted alkyl, substituted or unsubstituted alkenyl, —OH, —NH$_2$, —SH, —CO$_2$H, halogen, —OS(O$_2$)R$^B$, or —(C═O)OR$^C$; R$^C$ is substituted or unsubstituted heterocyclyl; and R$^B$ is substituted or unsubstituted alkyl or substituted or unsubstituted aryl.

In certain embodiments, -L$^1$-L$^2$-T is

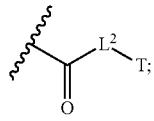

wherein L$^2$ is substituted or unsubstituted C$_{8-12}$ alkylene, or substituted or unsubstituted C$_{8-12}$ alkenylene; and T is substituted alkyl, substituted or unsubstituted alkenyl, —OH, or —Cl.

In certain embodiments, -L$^1$-L$^2$-T is

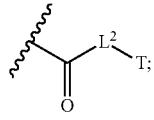

wherein L$^2$ is substituted or unsubstituted C$_{8-30}$ alkylene, or substituted or unsubstituted C$_{8-30}$ alkenylene; T is —Cl, —OH,

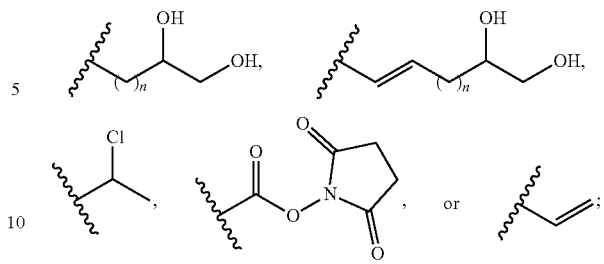

and n is an integer from 0-8.

In certain embodiments, -L$^1$-L$^2$-T is

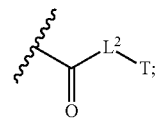

wherein L$^2$ is substituted or unsubstituted C$_{8-12}$ alkylene, or substituted or unsubstituted C$_{8-12}$ alkenylene; T is —Cl, —OH,

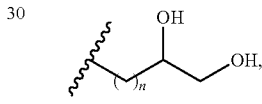

and n is an integer from 0-8.

In certain embodiments, -L$^1$-L$^2$-T is

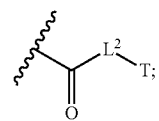

wherein L$^2$ is substituted or unsubstituted C$_{8-12}$ alkylene, or substituted or unsubstituted C$_{8-12}$ alkenylene; T is —Cl, —OH,

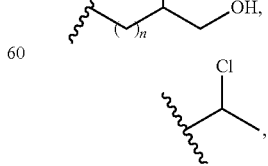

and n is an integer from 0-8.

In certain embodiments, -L¹-L²-T is

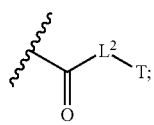

wherein L² is substituted or unsubstituted $C_{8-12}$ alkylene, or substituted or unsubstituted $C_{8-12}$ alkenylene; T is

and n is an integer from 0-8.

In certain embodiments, -L¹-L²-T is

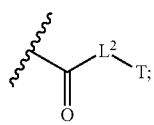

wherein L² is substituted or unsubstituted $C_{8-30}$ alkylene, substituted or unsubstituted $C_{8-30}$ alkenylene, substituted or unsubstituted $C_{4-30}$ heteroalkylene; and T is

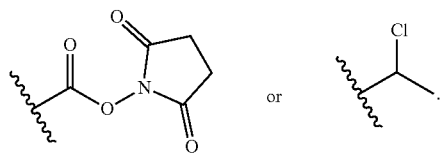

In certain embodiments, -L¹-L²-T is

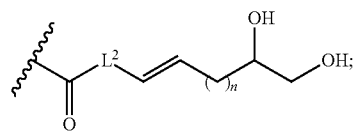

wherein L² is substituted or unsubstituted $C_{8-12}$ alkylene; substituted or unsubstituted $C_{8-12}$ alkenylene; substituted or unsubstituted $C_{4-12}$ heteroalkylene; or substituted or unsubstituted $C_{4-12}$ heteroalkenylene; and n is an integer from 0-8.

In certain embodiments, the compound of Formula (I) is of Formula (I-a):

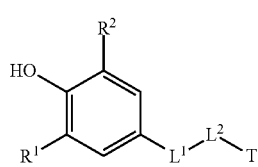

(I-a)

or a pharmaceutically acceptable salt thereof, wherein R¹, R², L¹, L², and T are as defined herein.

In certain embodiments, the compound of Formula (I) is of Formula (I-b):

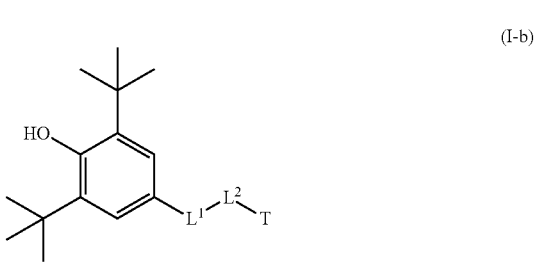

(I-b)

or a pharmaceutically acceptable salt thereof, wherein L¹, L², and T are as defined herein.

In certain embodiments, the compound of Formula (I) is of Formula (I-b1):

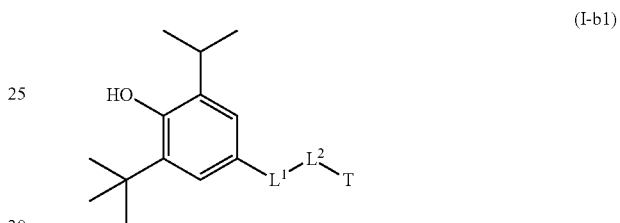

(I-b1)

or a pharmaceutically acceptable salt thereof, wherein L¹, L², and T are as defined herein.

In certain embodiments, the compound of Formula (I) is of Formula (I-b2):

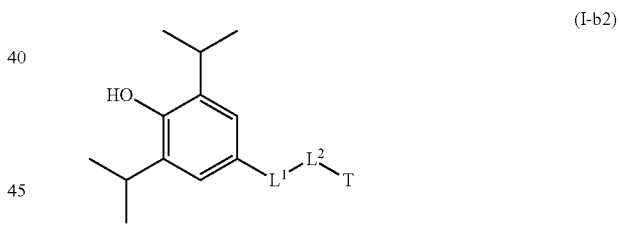

(I-b2)

or a pharmaceutically acceptable salt thereof, wherein L¹, L², and T are as defined herein.

In certain embodiments, the compound of Formula (I) is of Formula (I-c):

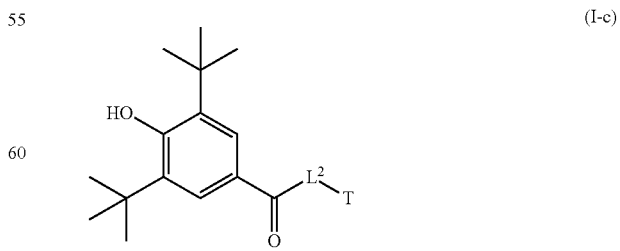

(I-c)

or a pharmaceutically acceptable salt thereof, wherein L¹, L², and T are as defined herein.

In certain embodiments, the compound of Formula (I) is of Formula (I-c1):

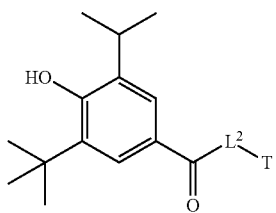

(I-c1)

or a pharmaceutically acceptable salt thereof, wherein $L^1$, $L^2$, and T are as defined herein.

In certain embodiments, the compound of Formula (I) is of Formula (I-c2):

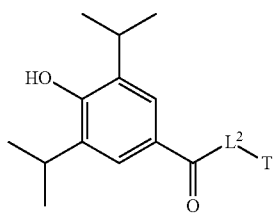

(I-c2)

or a pharmaceutically acceptable salt thereof, wherein $L^1$, $L^2$, and T are as defined herein.

In certain embodiments, the compound of Formula (I) is of Formula (I-d):

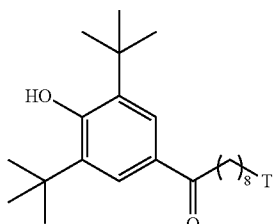

(I-d)

or a pharmaceutically acceptable salt thereof, wherein T is as defined herein.

In certain embodiments, the compound of Formula (I) is of Formula (I-d1):

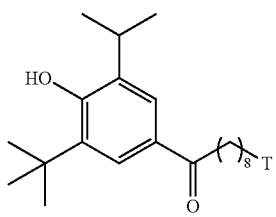

(I-d1)

or a pharmaceutically acceptable salt thereof, wherein T is as defined herein.

In certain embodiments, the compound of Formula (I) is of Formula (I-d2):

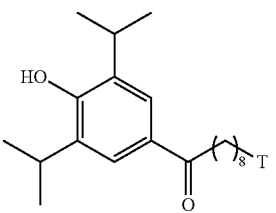

(I-d2)

or a pharmaceutically acceptable salt thereof, wherein T is as defined herein.

In certain embodiments, the compound of Formula (I) is of Formula (I-e):

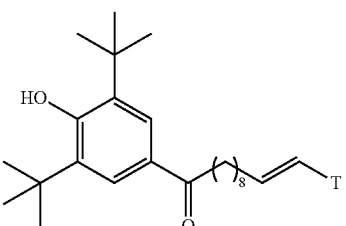

(I-e)

or a pharmaceutically acceptable salt thereof, wherein T is as defined herein.

In certain embodiments, the compound of Formula (I) is of Formula (I-e1):

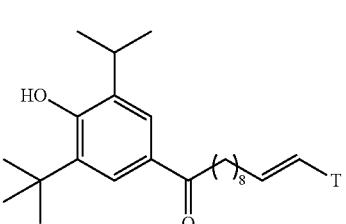

(I-e1)

or a pharmaceutically acceptable salt thereof, wherein T is as defined herein.

In certain embodiments, the compound of Formula (I) is of Formula (I-e2):

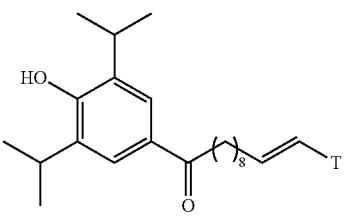

(I-e2)

or a pharmaceutically acceptable salt thereof, wherein T is as defined herein.

In certain embodiments, the compound of Formula (I) is of formula:
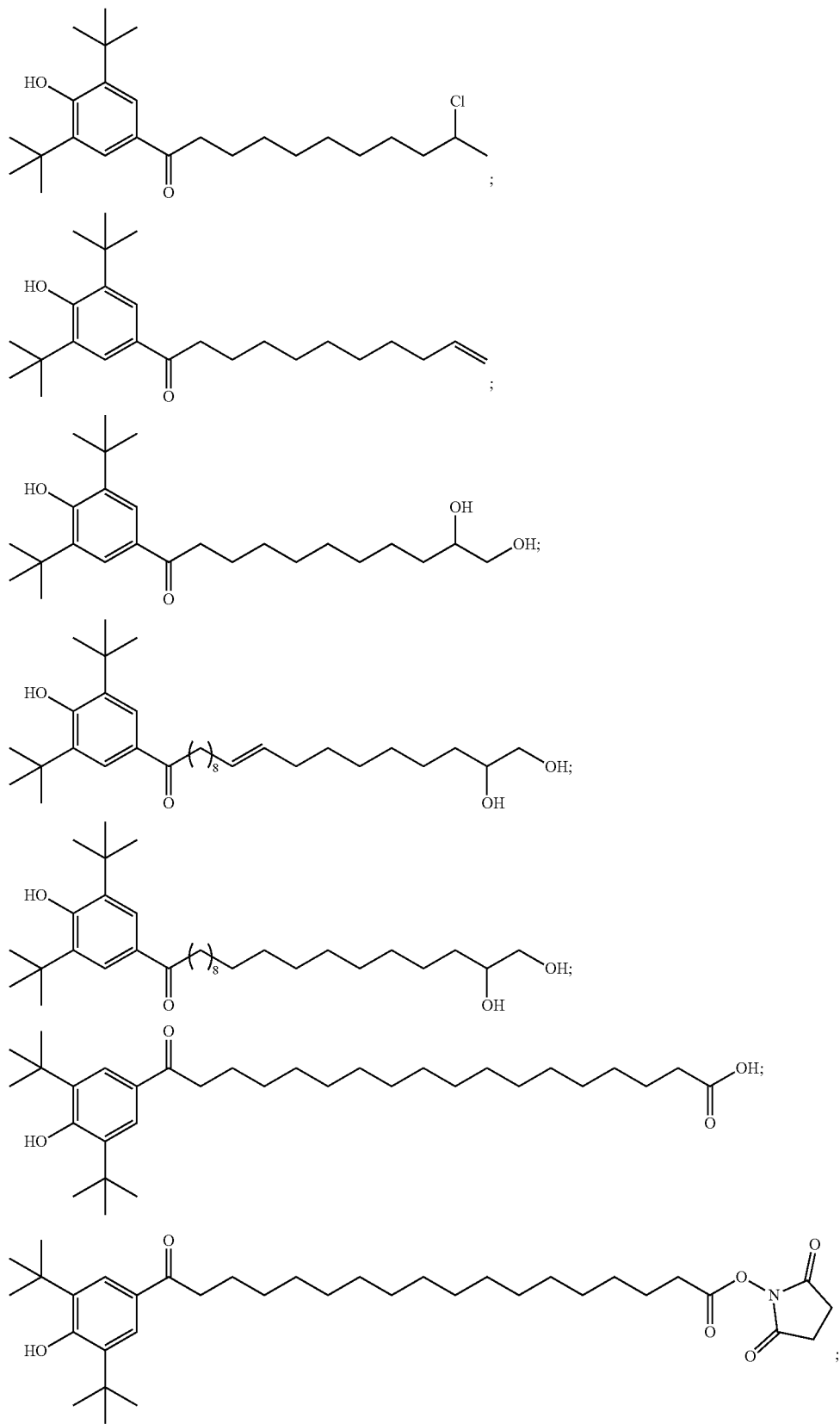

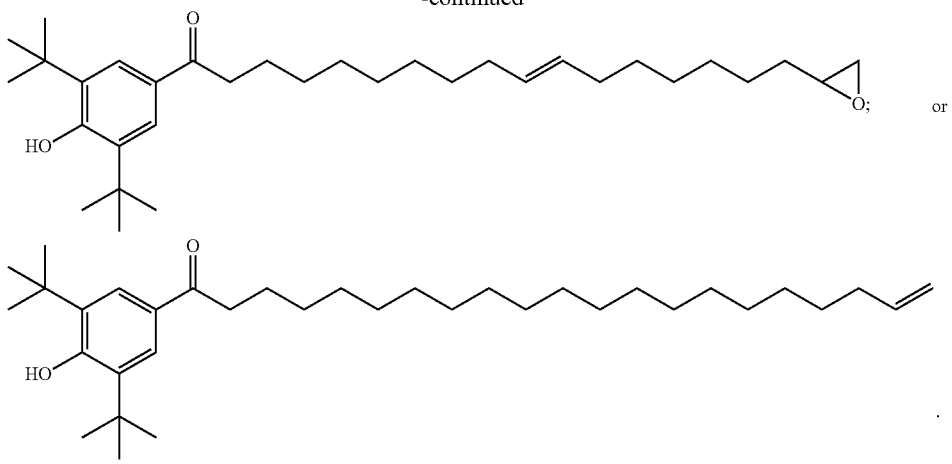

Methods of Treatment and Uses.

The present disclosure provides methods of treating pain (e.g. chronic pain) in a subject in need thereof, the method comprising administering an effective amount of a compound of any of Formula (I), Formula (II), or a pharmaceutically acceptable salt thereof. In certain embodiments, the chronic pain is a neuropathic pain characterized by one or more symptoms selected from the group consisting of persistent negative sensory perception, hyperalgesia, allodynia, burning sensation, and unusual nociceptive descriptors.

The present disclosure provides methods of modulating (e.g., inhibiting or increasing) the activity (e.g., aberrant activity, or undesired activity, such as increased or decreased activity) of HCN channel gating (e.g., HCN1 channel gating). The present disclosure provides methods of modulating (e.g., inhibiting or increasing) the activity (e.g., aberrant activity, such as increased or decreased activity) of HCN channel gating (e.g., HCN1 channel gating) in a subject. In certain embodiments, the methods inhibit HCN (e.g., HCN1) channel gating. The present disclosure also provides methods for the treatment of a wide range of diseases, such as diseases associated with the aberrant activity (e.g., increased activity) of HCN channel gating, e.g., pain (e.g., chronic pain), in a subject.

The present disclosure further provides methods of using the compounds described herein, e.g., as biological probes to study the inhibition of the activity of HCN channel gating (e.g., HCN1 channel gating), and as therapeutics, e.g., in the treatment of diseases associated with the overexpression and/or aberrant activity of HCN channel gating (e.g., HCN1 channel gating). In certain embodiments, the compounds inhibit HCN channel gating (e.g., HCN1 channel gating). In certain embodiments, the compounds inhibit HCN channel gating (e.g., HCN1 channel gating) without enhancing (e.g., increasing the activity of) a gamma-aminobutyric acid-A (GABA-A) receptor. In certain embodiments, the compounds inhibit HCN channel gating (e.g., HCN1 channel gating) without modulating the activity of a GABA-A receptor. In certain embodiments, the diseases treated and/or prevented include, but are not limited to, pain (e.g., chronic pain) in a subject. In certain embodiments, the pain is associated with the aberrant activity of HCN channel gating (e.g., HCN1 channel gating). Also provided by the present disclosure are pharmaceutical compositions, kits, methods, and uses of a compound of Formula (I), or Formula (II) as described herein.

Certain compounds described herein bind, covalently modify, antagonize, and/or inhibit HCN channel gating (e.g., HCN1 channel gating). In certain embodiments, the compounds described herein modulate the activity of HCN channel gating (e.g., HCN1 channel gating). In certain embodiments, the compounds described herein inhibit the activity of HCN channel gating (e.g., HCN1 channel gating).

It is expected that the compounds described herein may be useful in treating and/or preventing diseases associated with aberrant activity (e.g., increased activity, undesired activity, abnormal activity) of HCN channel gating (e.g., HCN1 channel gating). It is known in the art that HCN channel gating is implicated in a wide range of diseases and conditions, such as pain (e.g., chronic pain) in a subject. Therefore, the compounds described herein are expected to be useful in treating and/or preventing diseases (e.g., pain (e.g., chronic pain).

The present disclosure also provides a compound of Formula (I), or a pharmaceutically acceptable salt thereof, for use in the treatment of diseases, such as pain (e.g., chronic pain), in a subject. The present disclosure also provides a compound of Formula (II), or a pharmaceutically acceptable salt thereof, for use in the treatment of diseases, such as pain (e.g., chronic pain), in a subject.

The present disclosure also provides uses of a compound of Formula (I), or a pharmaceutically acceptable salt thereof, in the manufacture of a medicament for the treatment of diseases, such as pain (e.g., chronic pain). The present disclosure also provides uses of a compound of Formula (II), or a pharmaceutically acceptable salt thereof, in the manufacture of a medicament for the treatment of diseases, such as pain (e.g., chronic pain).

In certain embodiments, provided are methods of decreasing the activity of HCN channel gating (e.g., HCN1 channel gating) in a subject (e.g., cell, tissue) by a method described herein by at least about 1%, at least about 3%, at least about 10%, at least about 20%, at least about 30%, at least about 40%, at least about 50%, at least about 60%, at least about 70%, at least about 80%, or at least about 90%. In certain embodiments, the activity of HCN channel gating (e.g., HCN1 channel gating) in a subject or cell is decreased by a method described herein by at least about 1%, at least about 3%, at least about 10%, at least about 20%, at least about 30%, at least about 40%, at least about 50%, at least about 60%, at least about 70%, at least about 80%, or at least about 90%. In some embodiments, the activity of HCN channel gating (e.g., HCN1 channel gating) in a subject is selectively inhibited by the method. In some embodiments, the activity of HCN channel gating (e.g., HCN1 channel gating) in a subject or cell is selectively decreased by the method.

In another aspect, the present disclosure provides methods of inhibiting the activity of HCN channel gating (e.g., HCN1 channel gating) in a cell, the methods comprising contacting the cell with an effective amount of a compound, or a pharmaceutical composition thereof, as described herein.

In certain embodiments, the subject being treated is a mammal. In certain embodiments, the subject is a human. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent, dog, or non-human primate. In certain embodiments, the subject is a non-human transgenic animal, such as a transgenic mouse or transgenic pig. In certain embodiments, the subject is a fish or reptile. In certain embodiments, the subject is an animal. The animal may be of either sex and may be at any stage of development. In certain embodiments, the subject described herein is a human. In certain embodiments, the subject is a non-human animal. In certain embodiments, the subject is a mammal.

In certain embodiments, the cell being contacted with a compound or composition described herein is in vitro. In certain embodiments, the cell being contacted with a compound or composition described herein is in vivo.

In certain embodiments, the disease (e.g., pain) to be treated or prevented using the compounds described herein may be associated with the overexpression of HCN channel gating (e.g., HCN1 channel gating). A disease (e.g., pain) may be associated with aberrant activity of HCN channel gating (e.g., HCN1 channel gating). Aberrant activity of HCN channel gating (e.g., HCN1 channel gating) may be elevated and/or inappropriate and/or undesired activity of HCN channel. The compounds described herein, and pharmaceutically acceptable salts, solvates thereof, may inhibit the activity of HCN channel gating (e.g., HCN1 channel gating) and be useful in treating and/or preventing diseases (e.g., pain). The compounds described herein, and pharmaceutically acceptable salts thereof, may inhibit the activity of HCN channel gating (e.g., HCN1 channel gating) and be useful in treating and/or preventing diseases (e.g., pain). The compounds described herein, and pharmaceutically acceptable salts thereof, may inhibit the activity of HCN channel gating (e.g., HCN1 channel gating) and be useful in treating and/or preventing diseases (e.g., pain).

Pharmaceutical Compositions, Kits, and Administration

The present disclosure also provides pharmaceutical compositions comprising a compound described herein and optionally a pharmaceutically acceptable excipient. In certain embodiments, a compound described herein is a compound of Formula (I), Formula (II), or a pharmaceutically acceptable salt thereof, and a pharmaceutically acceptable excipient.

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, a therapeutically effective amount is an amount effective for inhibiting the aberrant activity of HCN channel gating (e.g., HCN1 channel gating). In certain embodiments, a therapeutically effective amount is an amount effective for treating a disease (e.g., a disease associated with aberrant activity of HCN channel gating (e.g., pain) in a subject. In certain embodiments, a prophylactically effective amount is an amount effective for inhibiting the aberrant activity of HCN channel gating (e.g., HCN1 channel gating). In certain embodiments, a prophylactically effective amount is an amount effective for inhibiting the aberrant activity of HCN channel gating (e.g., HCN1 channel gating).

In certain embodiments, the effective amount is an amount effective for inhibiting the activity of HCN channel gating (e.g., HCN1 channel gating) by at least 10%, at least 20%, at least 30%, at least 40%, at least 50%, at least 60%, at least 70%, at least 80%, at least 90%, at least 95%, or at least 98%. In certain embodiments, the effective amount is an amount effective for inhibiting the activity of HCN channel gating (e.g., HCN1 channel gating) by not more than 10%, not more than 20%, not more than 30%, not more than 40%, not more than 50%, not more than 60%, not more than 70%, not more than 80%, not more than 90%, not more than 95%, or not more than 98%.

Another aspect of the disclosure relates to methods of inhibiting the activity of HCN channel gating (e.g., HCN1 channel gating) in a subject. In certain embodiments, the methods described herein include administering to a subject with an effective amount of a compound described herein, or a pharmaceutically acceptable salt thereof, or a pharmaceutical composition thereof.

In certain embodiments, the compound or pharmaceutical composition is a solid. In certain embodiments, the compound or pharmaceutical composition is a powder. In certain embodiments, the compound or pharmaceutical composition can be dissolved in a liquid to make a solution. In certain embodiments, the compound or pharmaceutical composition is dissolved in water to make an aqueous solution. In certain embodiments, the pharmaceutical composition is a liquid for parenteral injection. In certain embodiments, the pharmaceutical composition is a liquid for oral administration (e.g., ingestion). In certain embodiments, the pharmaceutical composition is a liquid (e.g., aqueous solution) for intravenous injection. In certain embodiments, the pharmaceutical composition is a liquid (e.g., aqueous solution) for subcutaneous injection.

After formulation with an appropriate pharmaceutically acceptable excipient in a desired dosage, the pharmaceutical compositions of the present disclosure can be administered to humans and other animals orally, parenterally, intracisternally, intraperitoneally, topically, bucally, or the like, depending on the disease or condition being treated.

In certain embodiments, a pharmaceutical composition comprising a compound of Formula I is administered, orally or parenterally, at dosage levels of each pharmaceutical composition sufficient to deliver from about 0.001 mg/kg to about 200 mg/kg in one or more dose administrations for one or several days (depending on the mode of administration). In certain embodiments, the effective amount per dose varies from about 0.001 mg/kg to about 200 mg/kg, about 0.001 mg/kg to about 100 mg/kg, about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, of subject body weight per day, one or more times a day, to obtain the desired therapeutic and/or prophylactic effect. In certain embodiments, the compounds described herein may be at dosage levels sufficient to deliver from about 0.001 mg/kg to about 200 mg/kg, from about 0.001 mg/kg to about 100 mg/kg, from about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In certain embodiments, the composition described herein is administered at a dose that is below the dose at which the agent causes non-specific effects.

In certain embodiments, the pharmaceutical composition is administered at a dose of about 0.001 mg to about 1000 mg per unit dose. In certain embodiments, the pharmaceutical composition is administered at a dose of about 0.01 mg to about 200 mg per unit dose. In certain embodiments, the pharmaceutical composition is administered at a dose of about 0.01 mg to about 100 mg per unit dose. In certain embodiments, pharmaceutical composition is administered at a dose of about 0.01 mg to about 50 mg per unit dose. In certain embodiments, the pharmaceutical composition is administered at a dose of about 0.01 mg to about 10 mg per unit dose. In certain embodiments, the pharmaceutical composition is administered at a dose of about 0.1 mg to about 10 mg per unit dose.

Pharmaceutical compositions described herein can be prepared by any method known in the art of pharmacology. In general, such preparatory methods include the steps of bringing the composition comprising a compound of Formula I into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfate, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazelnut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include, but are not limited to, pharmaceutically acceptable emulsions, microemulsions, solutions, suspensions, syrups, and elixirs. In addition to the active agents, the liquid dosage forms may contain inert diluents commonly used in the art such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can also include adjuvants such as wetting agents, emulsifying and suspending agents, sweetening, flavoring, and perfuming agents. In certain embodiments for parenteral administration, agents of the invention are mixed with solubilizing agents such CREMOPHOR EL® (polyethoxylated castor oil), alcohols, oils, modified oils, glycols, polysorbates, cyclodextrins, polymers, and combinations thereof.

Injectable preparations, for example, sterile injectable aqueous or oleaginous suspensions, may be formulated according to the known art using suitable dispersing or wetting agents and suspending agents. Sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active agents can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used. Ophthalmic formulation, ear drops, and eye drops are also contemplated as being within the scope of this invention. Additionally, the present disclosure contemplates the use of transdermal patches, which have the added advantage of providing controlled delivery of an agent to the body. Such dosage forms can be made by dissolving or dispensing the agent in the proper medium. Absorption enhancers can also be used to increase the flux of the agent across the skin. The rate can be controlled by either providing a rate controlling membrane or by dispersing the agent in a polymer matrix or gel.

Additionally, the carrier for a topical formulation can be in the form of a hydroalcoholic system (e.g., liquids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

In certain embodiments, a kit described herein includes a first container comprising a compound or pharmaceutical composition described herein. In certain embodiments, a kit described herein is useful in treating and/or preventing a disease, such as pain (e.g., chronic pain) in a subject. In certain embodiments, a kit described herein is useful in inhibiting the activity of HCN channel gating (e.g., HCN1 channel gating) in a subject.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease, (e.g., pain (e.g., chronic pain), inhibiting the activity of HCN channel gating (e.g., HCN1 channel gating) in a subject. A kit described herein may include one or more additional pharmaceutical agents described herein as a separate composition.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Example 1. Exemplary Compounds are Effective Antagonists of HCN1 Channels when Applied from the Outside in Two Electrode Voltage Clamp (TEVC)

Figure 3:
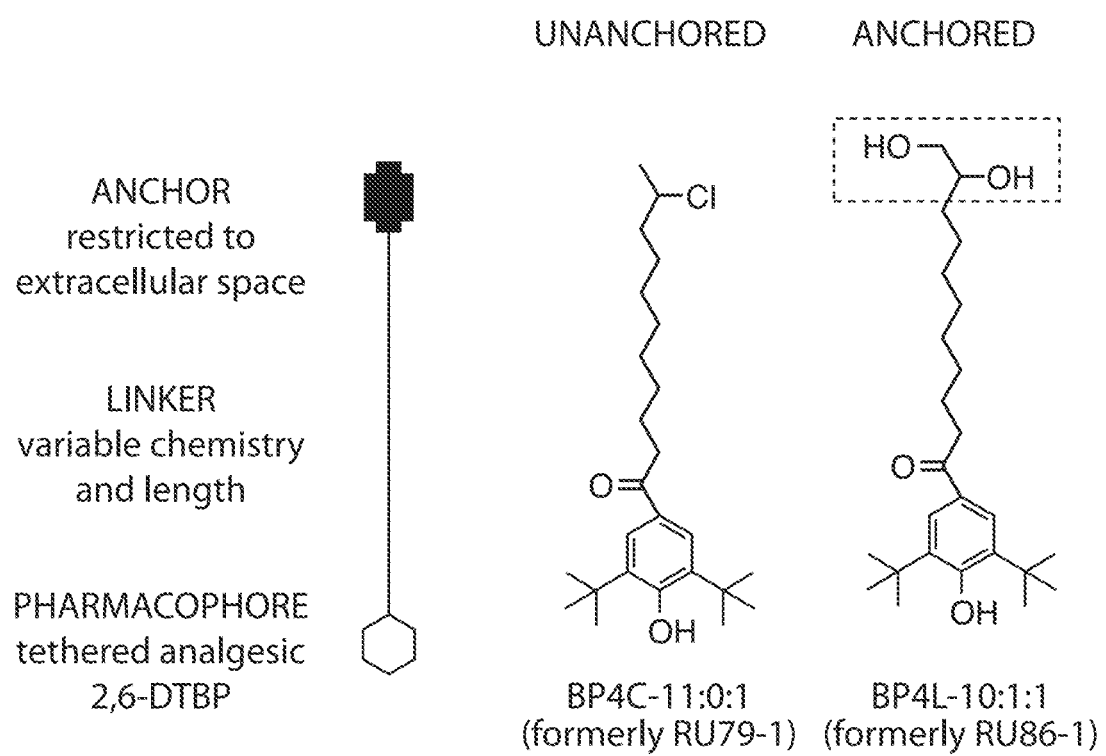
FIG. 3 shows a schematic representation of the conceptualized anchor-tethered 2,6-di-tert-butylphenol (2,6-DTBP) therapeutic and the structures of BP4C-11:0:1 and BP4L-10:0:1, two tethered derivatives of 2,6-DTBP. BP4L-10:0:1 incorporates a diol "anchor" (enclosed by the dashed box). BP4C-11:0:1 is unanchored.
Figure 4:
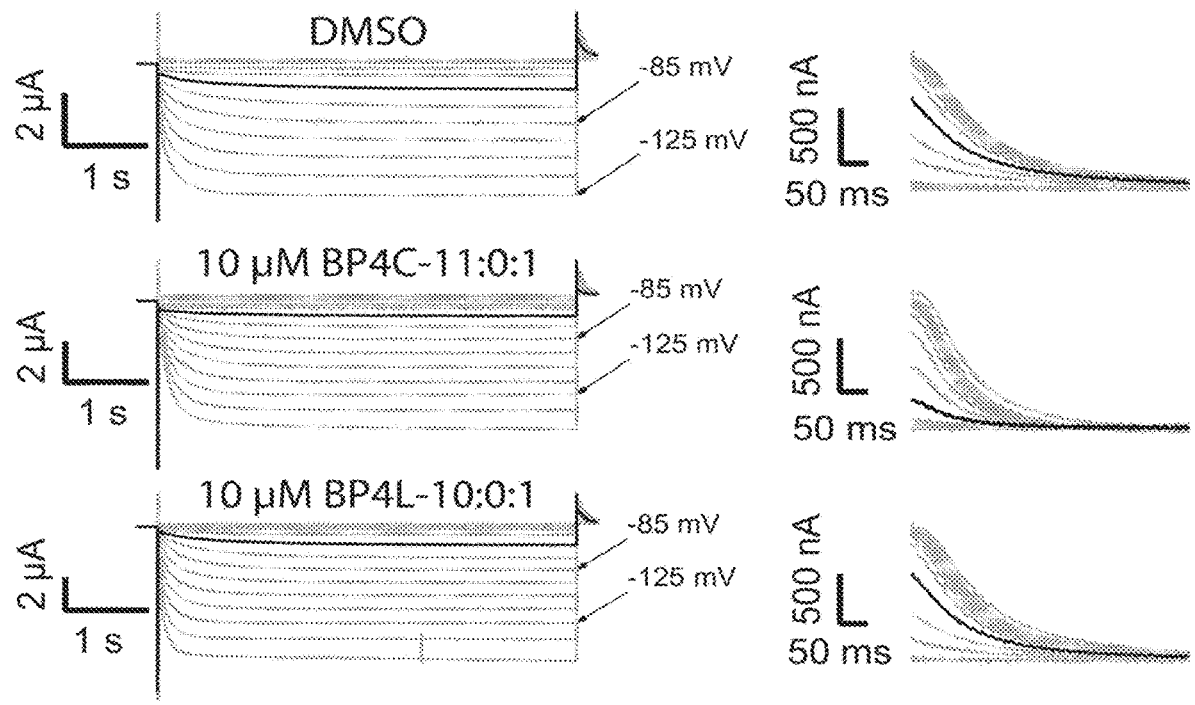
FIG. 4 shows records from three separate cells expressing HCN1-ΔNvΔCv each exposed to the indicated concentration of BP4C-11:0:1, BP4L-10:0:1 or DMSO vehicle alone. Records on the left are currents activated at hyperpolarizing step potentials, currents on the right are tails at 0 mV.
Figure 5:
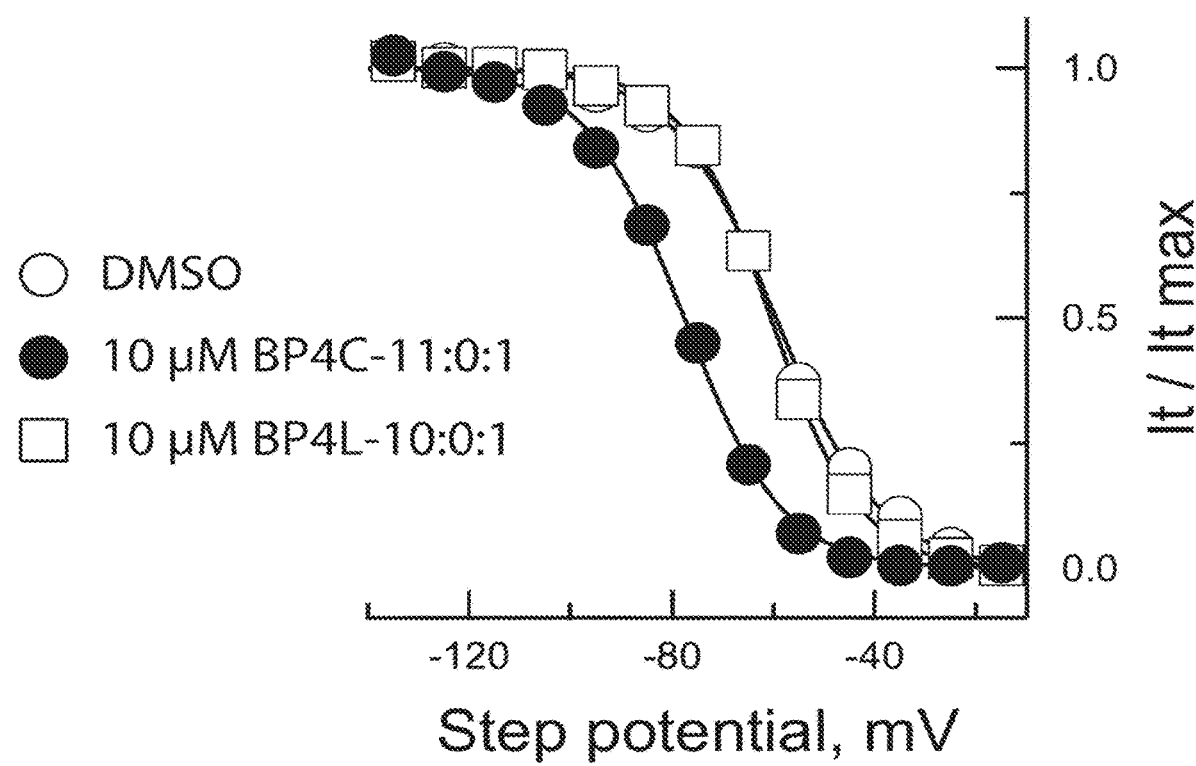
FIG. 5 shows tail current activation curves fit with the Boltzmann function for the three cells shown in FIG. 4.
Figure 6:
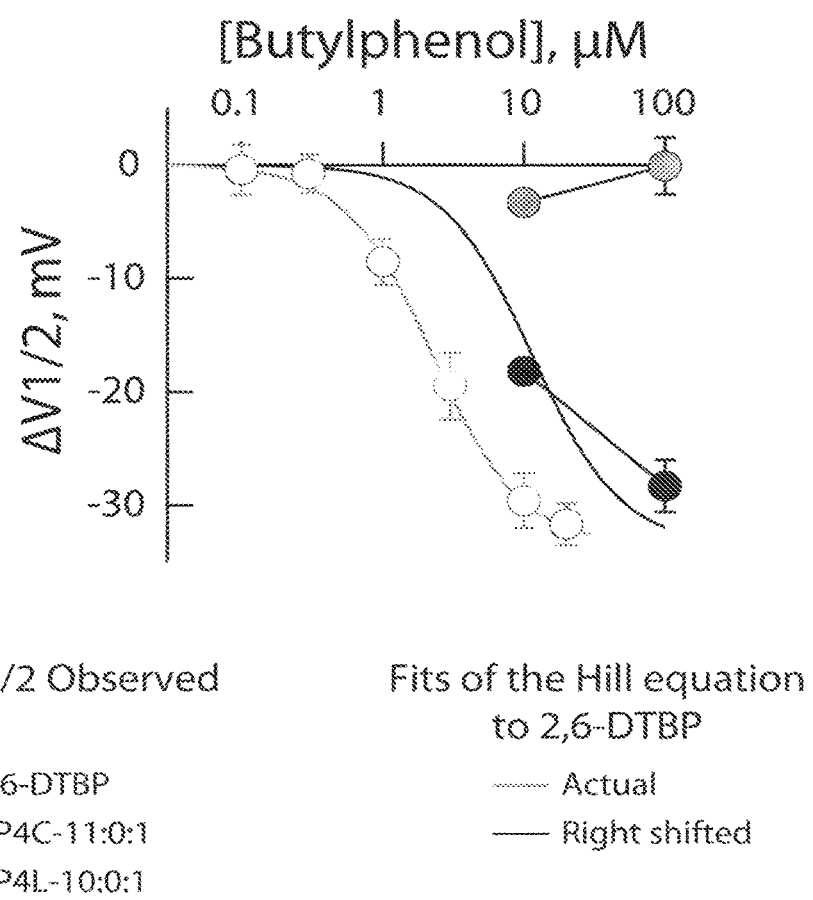
FIG. 6 shows the shift in the $V_{1/2}$ as a function of butylphenol concentration.

FIG. 3 shows BP4C-11:0:1 and BP4L-10:0:1 with respect to the hypothetical anchor-tethered 2,6-DTBP. FIG. 4 shows records from three separate cells expressing HCN1-ΔNvΔCv. Each cell was pre-incubated for 20 minutes in recording solution containing 0.04% DMSO alone or with 10 µM BP4C-11:0:1 or BP4L-10:0:1 as indicated. Current-voltage relationships (IVs) were collected with 3 and 5 second activation steps (5 s sweeps shown in each case here). There was no systematic difference in the $V_{1/2}$ reported by the two protocols showing activation was equilibrated at each voltage in both cases under all drug and vehicle conditions (not shown). Sweeps and tails obtained in response to activation at −65 mV are highlighted in black. Tail current activation curves fit with the Boltzmann function are shown for the three cells shown in FIG. 4 (FIG. 5). Data for BP4C-11:0:1 are from 9 cells (3 cells expressing wtHCN1 at 10 μM, 3 cells expressing HCN1-ΔNvΔCv at 10 μM; 2 cells expressing wtHCN1 at 100 μM, 1 HCN1-ΔNvΔCv at 100 μM). Data for BP4L-10:0:1 are from 6 cells (3 cells expressing HCN1-ΔNvΔCv at 10 μM and 3 cells expressing wt HCN1 at 100 μM). Smooth lines are a fit of the Hill function to the 2,6-DTBP data and a right-shifted version thereof as indicated.

BP4C-11:0:1 is a tethered, but unanchored, 2,6-DTBP. That is, BP4C-11:0:1 is a molecule that should relatively freely distribute into the membrane. Indeed, the new data greatly expands on that as they prove: 4-adduct tolerance is retained when the bulkier 2,6-DTBP pharmacophore is used instead of the di-iso-propylphenol head-group. Long tethers can be attached to the 4 position, something that was previously an assumption.

BP4L-10:0:1 is a tethered and anchored 2,6-DTBP, with the diol group being strongly favored to remain in the aqueous compartment. This shows pharmacophore penetration of the membrane is still required when the bulkier 2,6-DTBP pharmacophore is used instead of the di-iso-propylphenol. The alkylphenol site on HCN1 is a significant, and presumably measurable (albeit still unknown), depth into the membrane.

BP4C-11:0:1 and BP4L-10:0:1 solubilized readily into DMSO (dimethyl sulfoxide) and were reasonably easy to disperse into an aqueous buffer.

Data were collected from both wild-type HCN1 (wtHCN1) and a truncated HCN1 channel heterologously expressed in *Xenopus* oocytes, wherein the variable N and C domains were removed but the cyclic left intact nucleotide binding domain (CNBD) (HCN1-ΔNvΔCv). HCN1-ΔNvΔCv gates essentially identically to wtHCN1 but has the advantage that it is amenable to inside-out patch clamp (IOPC) recording techniques whereas wtHCN1 is extremely difficult to record in IOPC due to its propensity to cluster. Recordings for the data presented here where obtained using two-electrode voltage clamp.

Data are presented as shift in $V_{1/2}$ ($\Delta V_{1/2}$) with respect to the appropriate solvent vehicle, where $V_{1/2}$ is the midpoint of voltage activation. As cells were exposed to no more than one condition, the population mean of the vehicle was subtracted from each individual plus-drug measure. Drug effects were indistinguishable with respect to wtHCN1 and HCN1-ΔNvΔCv. Accordingly, $\Delta V_{1/2}$ values for wtHCN1 and HCN1-ΔNvΔCv were combined for this preliminary data set and the data are referred to as simply HCN1 unless they are from a specific cell.

Example 2. 2,6-DTBP is a Potent HCN1-Selective Inverse Agonist

Figure 7:
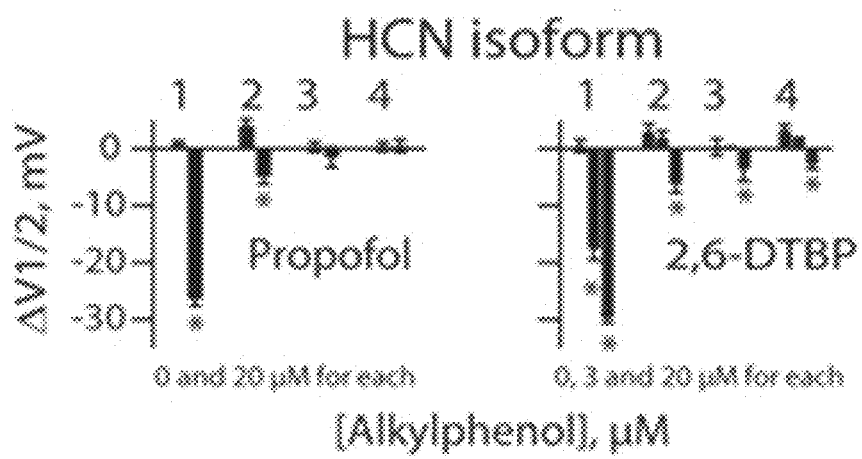
FIG. 7 shows the effect of propofol and 2,6-DTBP on $V_{1/2}$ of HCN1-4 channels. * indicates responses statistically different from control.
Figure 8:
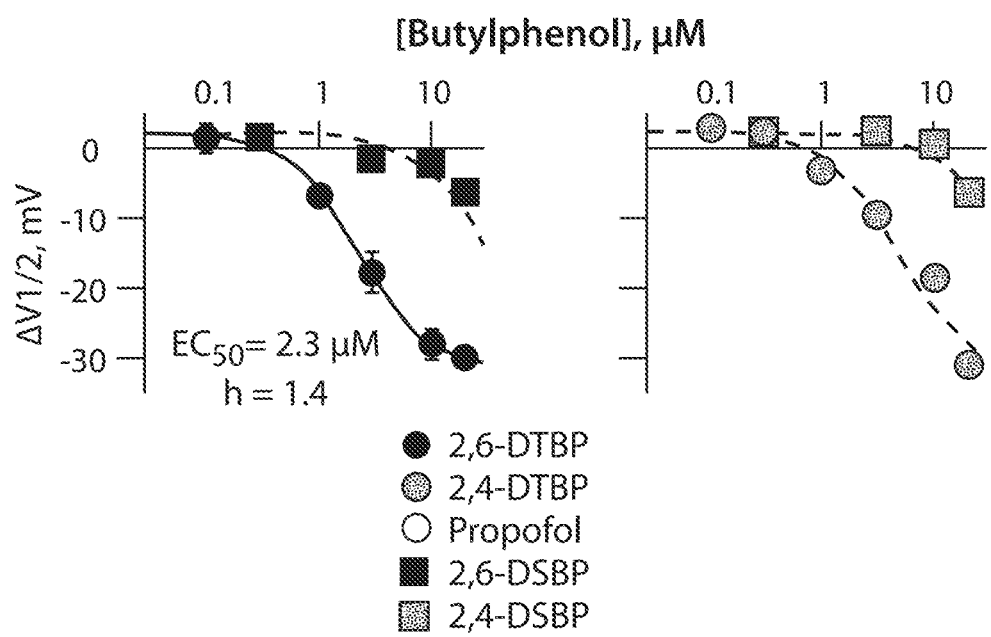
FIG. 8 shows the effect of 2,6- (left) or 2,4- (right) di-butylphenols on $V_{1/2}$ of HCN1 channels.

The effect of propofol and 2,6-DTBP on $V_{1/2}$ of HCN1-4 channels. * indicates responses statistically different from control (FIG. 7). Effect of 2,6- (left) or 2,4- (right) di-butylphenols on $V_{1/2}$ of HCN1 channels. The solid line and indicated parameter values are from a fit of the Hill function to the 2,6-DTBP relation; dashed lines are the 2,6-DTBP fit offset by 2-, 15-, and 23-fold for 2,4-DTBP, 2,6-DSBP, and 2,4-DSBP, respectively. The shift in $V_{1/2}$ was significant at >1 μM for DTBPs and at 20 μM for DSBPs (FIG. 8).

Figure 9:
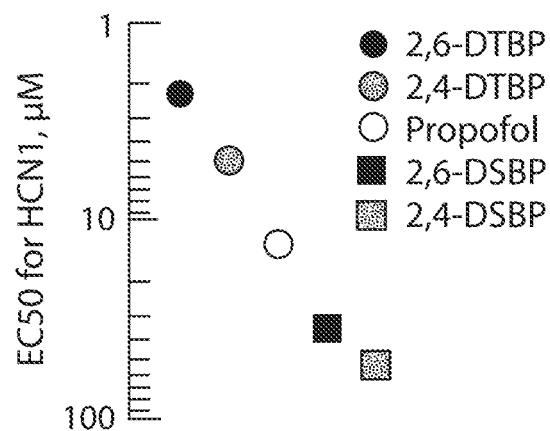
FIG. 9 shows the rank order of HCN1 antagonism as estimated from $EC_{50}$.
Figure 10:
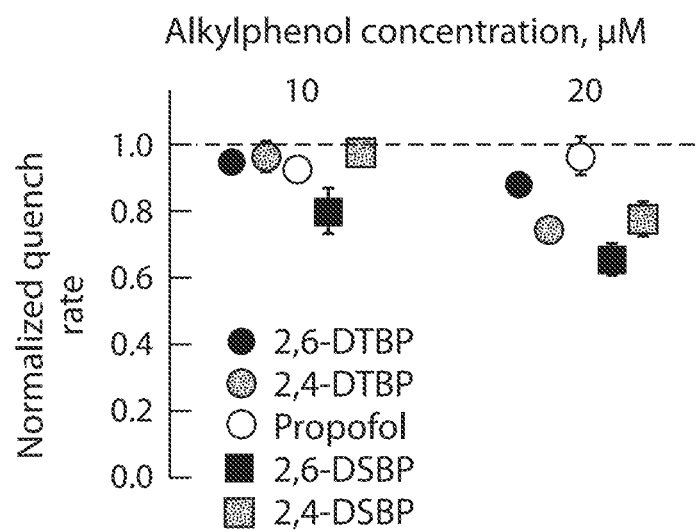
FIG. 10 shows the T1+-mediated fluorescent quench rate in large unilamellar vesicles, demonstrating that these compounds have minimal membrane effects.
Figure 11:
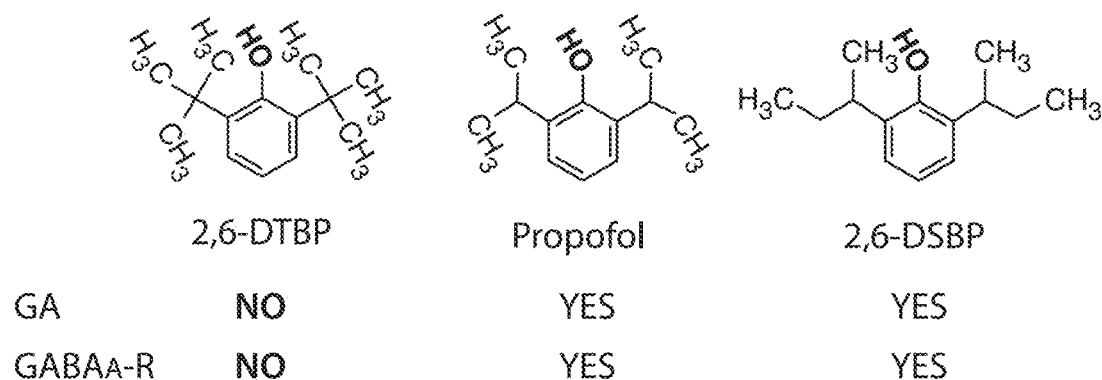
FIG. 11 shows the structure of three 2,6-alklyphenols and their efficacy as general anesthetics (GA) and positive modulators of $GABA_A$ receptor ($GABA_A$-R) function.

Rank order of HCN1 antagonism as estimated from $EC_{50}$ is shown in FIG. 9. T1+-mediated fluorescent quench rate in large unilamellar vesicles, demonstrating that these compounds have minimal membrane effects (FIG. 10). Structure of three 2,6-alklyphenols and their efficacy as general anesthetics (GA) and positive modulators of GABAA receptor (GABAA-R) function (FIG. 11).

Thus demonstrating that the novel compounds of the present technology have use as an anti-hyperalgesic for the treatment of peripheral neuropathic pain. The data demonstrated that: (1) 2,6- and 2,4-di-tert-butylphenol (2,6- and 2,4-DTBP) are more potent HCN1 inverse agonists than the intravenous general anesthetic propofol (2,6-di-iso-propylphenol), (2) 2,6- and 2,4-di-sec-butylphenol (2,6- and 2,4-DSBP) are less potent, and (3) 2,6-DTBP retains propofol's selectivity for HCN1 vs. HCN2-4.

Figure 12:
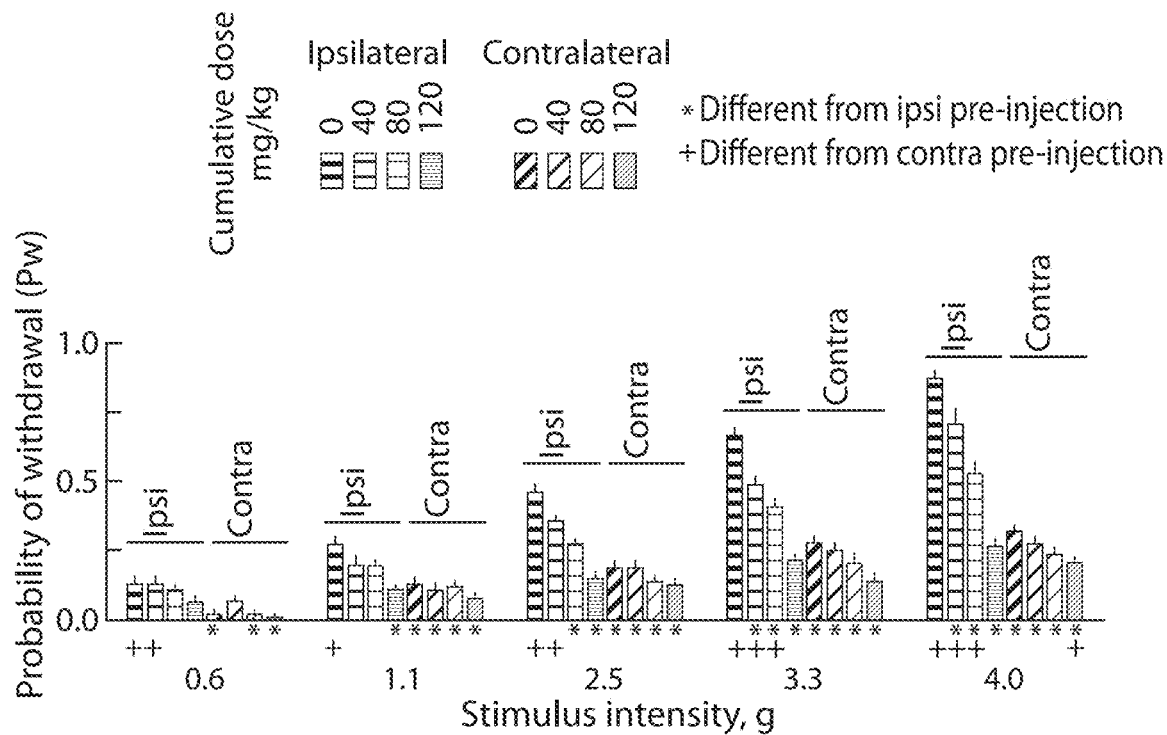
FIG. 12 shows the $P_{W,IPSI}$ and $P_{W,CONTRA}$ (probability of withdrawal of paw ipsi- or contra-lateral to nerve ligation) and effect of indicated cumulative i.p. dose of 2,6-DTBP as a function of stimulus fiber strength.
Figure 13:
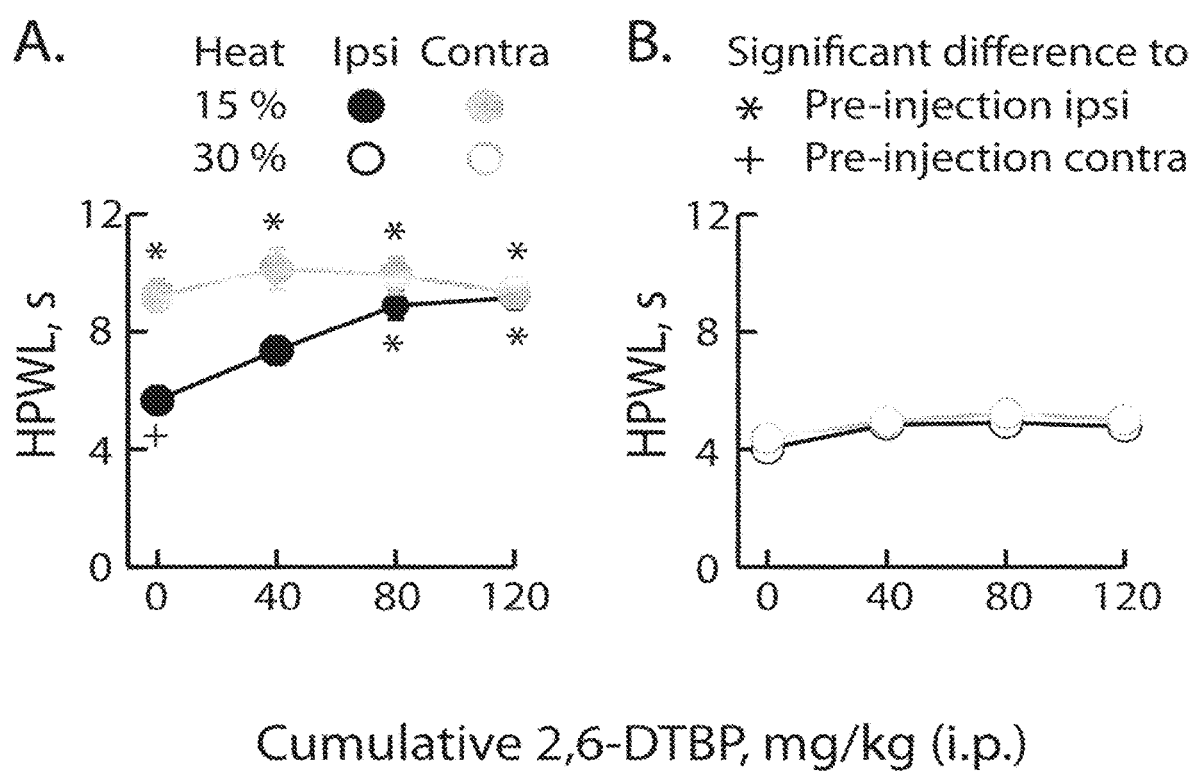
FIG. 13A and FIG. 13B show HPWL (hindpaw withdrawal latency) as a function of cumulative i.p. 2,6-DTBP dose and stimuls intensity. Heat source intensities of 15% and 30% (of 150 W max) elicit withdrawal responses between the fastest and slowest detection thresholds (2-3 and 30 s, respectively) with the lower setting optimal for examining thermal hyperalgesia and the higher setting examining a largely nociceptive response. 2,6-DTBP ameliorates thermal hyperalgesia without overt effect on thermal nociception.
Figure 14:
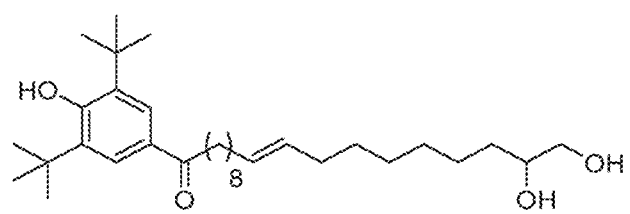
FIG. 14 shows the structure of BP4L-18:1:1 and BP4L-10:0:1.
Figure 14:
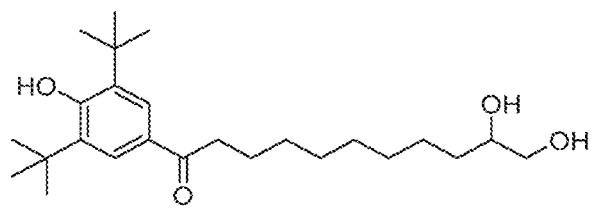

Example 3. 2,6-DTBP Selectively Suppresses Mechanical and Thermal Hyperalgesia with Respect to Mechanical and Thermal Nociception FIG. 12 shows $P_{W,IPSI}$ and $P_{W,CONTRA}$ (probability of withdrawal of paw ipsi- or contra-lateral to nerve ligation) and effect of indicated cumulative i.p. dose of 2,6-DTBP as a function of stimulus fiber strength (FIG. 12)). FIG. 13A and FIG. 13B show HPWL (hindpaw withdrawal latency) as a function of cumulative i.p. 2,6-DTBP dose at low (15%) and high (30%) stimulus intensity.

Notably, DTBPs are ineffective as general anesthetics due to lack of efficacy as agonists of GABA-A receptor function; additional data indicate that alkylphenols impair HCN1 gating via a sterically-defined site wherein a hydrogen-bond network contributes to initial binding energy with little involvement in coupling energy.

Example 4. Access of the Pharmacophore to its Site of Action Depends on Tether Length Novel chemical entities (NCEs) were synthesized which retained 2,6-DTBP as the pharmacophore with modification focusing on a "tether-anchor" with the aim of preserving HCN1-selective inhibition while preventing penetration across the lipid membrane (and ultimately, penetration into the CNS). One of those compounds, BP4L-18:1:1, has a number of the desired properties.

Figure 15:
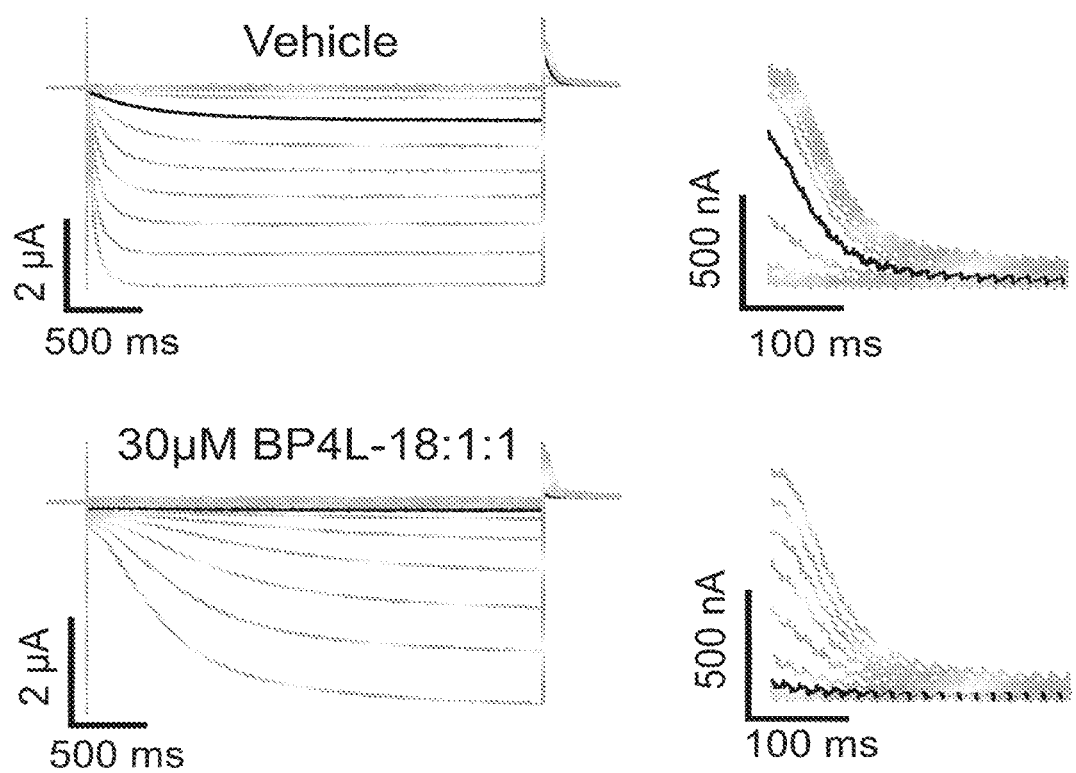
FIG. 15 shows current records from separate cells expressing HCN1. Each cell was pre-incubated for 20 mM in recording solution containing 20 mM 2-hydroxypropyl-β-cyclodextrin (HPβCD)+10 mM DMSO alone or with 30 μM BP4L-18:1:1 as indicated. Black sweeps are those recorded with an activation potential of −65 mV.
Figure 16:
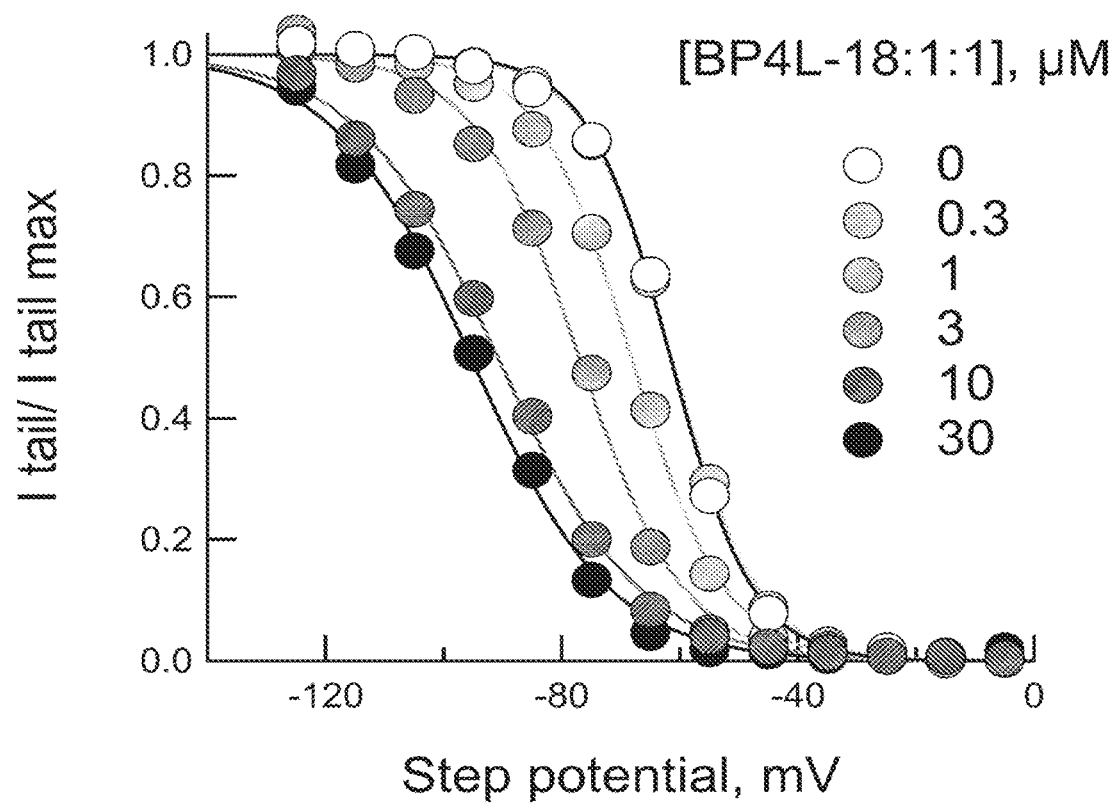
FIG. 16 shows inhibition of channel gating by BP4L-18:1:1 is concentration-dependent.
Figure 17:
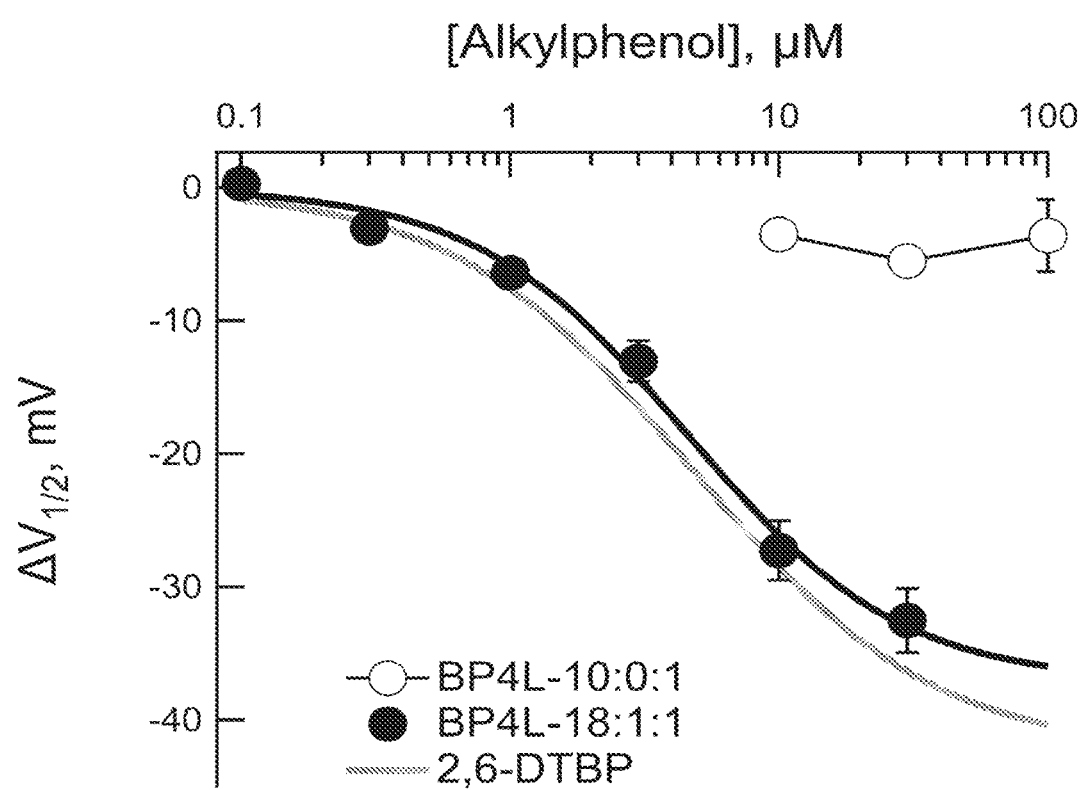
FIG. 17 shows BP4L-18:1:1 effectively inhibits channel gating with a potency and efficacy indistinguishable from free 2,6-DTBP (compare the black and grey Hill equation fit lines) while BP4L-10:0:1 (a pharmacophore with restricted access to the binding site) is largely ineffective.

Current records from separate cells expressing HCN1. Each cell was pre-incubated for 20 min in recording solution containing 20 mM 2-hydroxypropyl-β-cyclodextrin (HPβCD)+10 mM DMSO alone or with 30 μM BP4L-18:1:1 as indicated (FIG. 15). Black sweeps are those recorded with an activation potential of −65 mV. Inhibition of channel gating is concentration-dependent (FIG. 16). BP4L-18:1:1 effectively inhibits channel gating with a potency and efficacy indistinguishable from free 2,6-DTBP (compare the black and grey Hill fit lines in FIG. 17) while BP4L-10:0:1 (a pharmacophore with restricted access to the binding site) is largely ineffective (FIG. 17).

Figure 18:
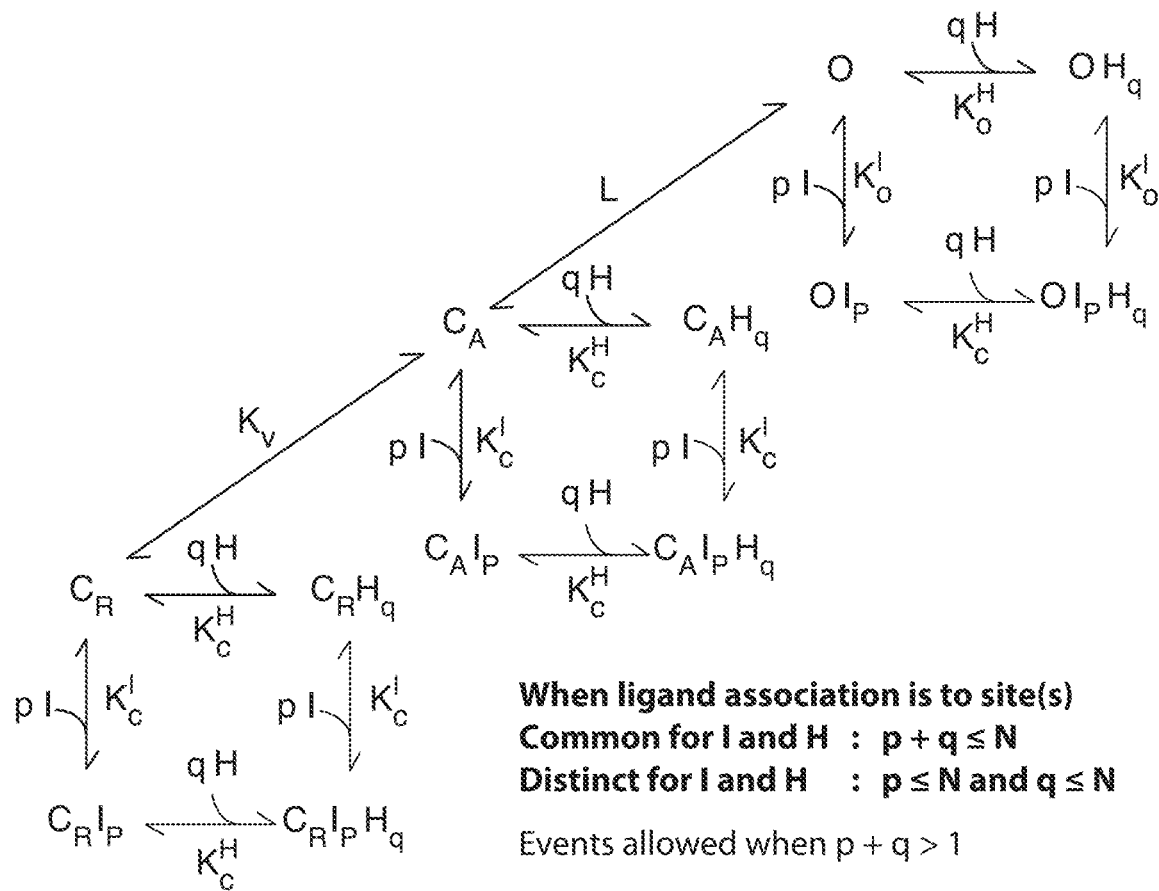
FIG. 18 shows alkylphenol and alkylcyclohexanol interaction with HCN1 channel gating modeled as, respectively, inverse agonist and partial inverse agonist coupling to channel opening.

Example 5. Alkylphenol and Alkylcyclohexanol Interaction with HCN1 Channel Gating Models FIG. 18 shows CR, CA and O represent the closed-resting, closed-activated and open states; KV and L the equilibrium constants describing activation and opening; I and H are an inverse agonist and a partial inverse agonist; p and q represent the number of binding events of I and H; KC and KO represent the association constants for I and H to closed and open channels with reference to I and H denoted by the appropriate superscript. For simplicity, only activation and opening transitions between un-liganded states are shown but all CR-CA and CA-O transitions are permissible. When H and I associate with common site(s) the model contains 3 states per plane, 9 states in total (N=1) and 15 states per plane, 45 states in total (N=4). When H and I associate with distinct site(s) the model contains 4 states per plane, 12 states in total (N=1) and 25 states per plane, 75 states in total (N=4). Importantly, as the equilibrium constants are the only free parameters and the number of equilibrium constants is independent of the expansion of the number of states, each of these models should be equally well determined if they are equally able to describe the data.

Figure 19A:
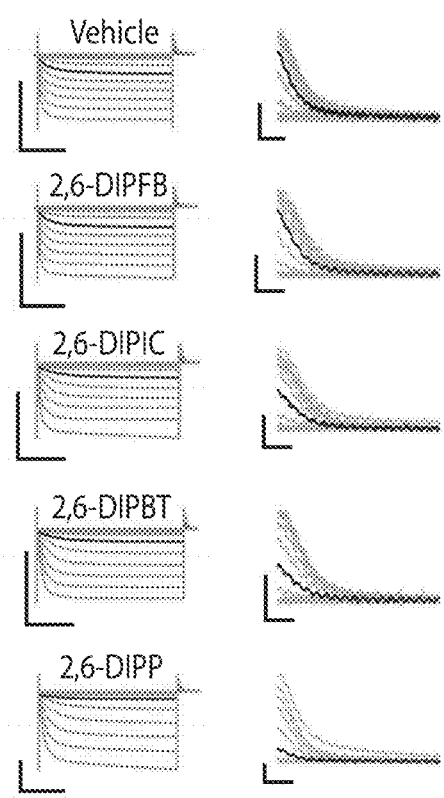
FIG. 19A and FIG. 19C are plots showing the current-voltage relationships of the dialkylbenzene compound structures in FIG. 19B. The plots show hydrogen bond functionality at position 1 is useful for dialkylbenzene inhibition of HCN1 gating. Black sweeps are those recorded at an activation potential of −75 mV (FIG. 19A).
Figure 19B:
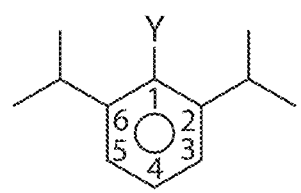
Figure 19C:
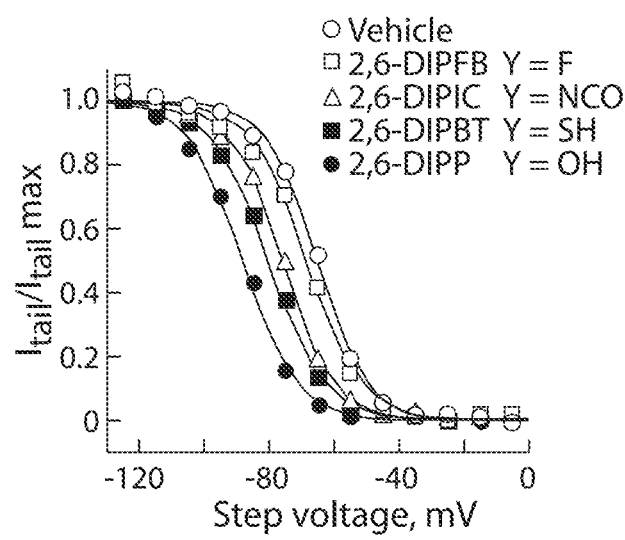

Example 6. Hydrogen Bond Functionality at Position 1 is Useful for Alkylbenzene Inhibition of HCN1 Gating FIG. 19A shows representative voltage-clamp recordings of HCN1 currents (left) following incubation for 20 min in the absence or presence of 10 µM of the indicated reagent. Tail currents (right) are shown on an expanded time scale. In each case the black trace is the current recorded at an activation potential of −75 mV. All recordings were obtained on the same day from distinct oocytes from a single donor frog. Scale bars are 2 µA and 1 s (left) and 200 nA and 50 ms (right). FIG. 19B shows chematic representation of 2,6-di-iso-propylbenzenes. Substitutions at the 1-position (as per the legend) describe molecules whose effects are reported in FIG. 19A and FIG. 19C. FIG. 19C shows ormalized steady-state activation curves constructed from the records shown in FIG. 19A. The smooth lines are fits of the Boltzmann function. Symbols represent molecules as described in FIG. 19B.

Figure 20:
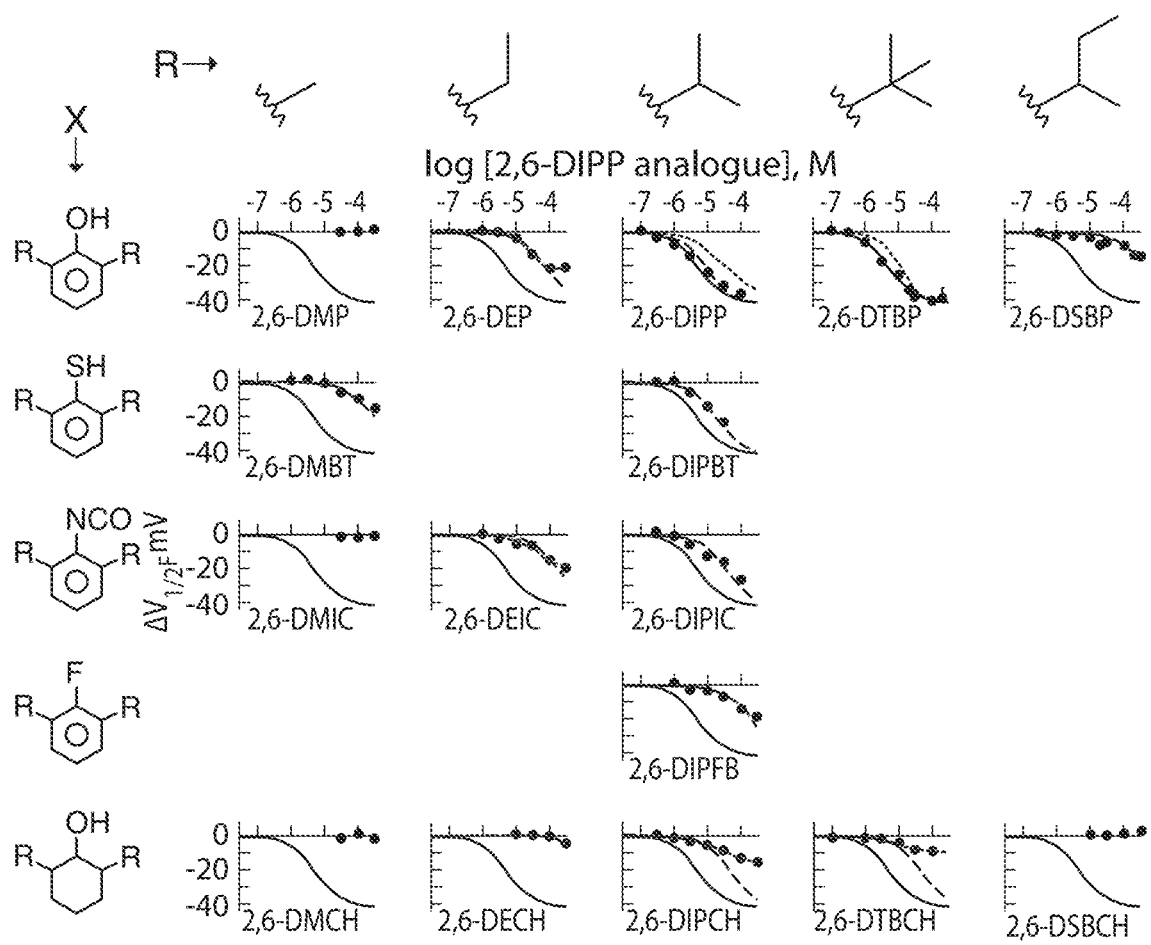
FIG. 20 shows inhibition by 2,6-di-alkylbenzene derivatives reveals hydrogen bond potential; alkyl side chain identity and the presence or absence of it electrons contribute differentially to the energetics of inverse agonism by this class of molecules. In each panel, the thick black lines are the fit of the Hill equation to 2,6-DTBP. Where present, the thin grey lines are the 2,6-DTBP Hill fit translated on the concentration axis by adjustment of the $EC_5O$ only; the thick grey lines are fits of the Hill equation to the concentration response in that panel; and the dashed grey lines in the 2,6-DIPP and 2,6-DTBP panels are the fits of the Hill equation to the 2,6-DIPCH and 2,6-DTBCH data with only the maximal response of the fit altered.

Example 7. Inhibition by 2,6-Di-Alkylbenzene Derivatives Reveals Hydrogen Bond Potential, Alkyl Side Chain Identity and the Presence or Absence of π-Electrons Differentially Contribute to Drug Function FIG. 20 shows the shift in the $V_{1/2}$ as a function of concentration of each of the indicated ligands. In each panel, the thick black lines are the fit of the Hill equation to 2,6-DTBP. Where present, the thin grey lines are the 2,6-DTBP Hill fit translated on the concentration axis by adjustment of the $EC_{50}$ only; the thick grey lines are fits of the Hill equation to the concentration response in that panel; and the dashed grey lines in the 2,6-DIPP and 2,6-DTBP panels are the fits of the Hill equation to the 2,6-DIPCH and 2,6-DTBCH data with only the maximal response of the fit altered such that the cyclohexanol fit lines were scaled according to the ratio $\Delta V_{1/2}$ MAX phenol/$\Delta V_{1/2}$ MAX cyclohexanol with all other terms of the cyclohexanol fit left unadjusted. All data are mean±SEM with 6 or more determinations per point.

Figure 21A:
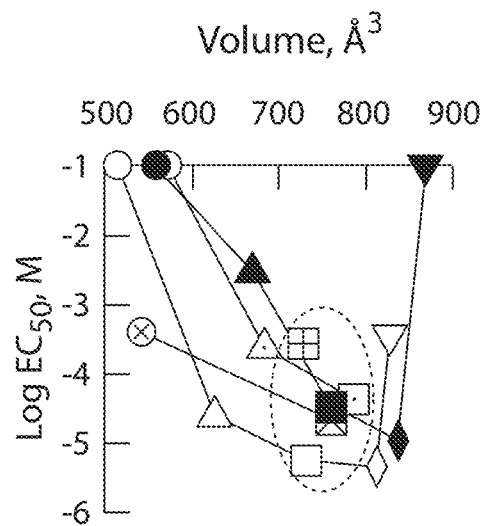
FIG. 21A is a plot showing inverse agonist potency ($EC_{50}$) of 2,6 di-alkylbenzene analogues as a function of molecular volume.
Figure 21B:
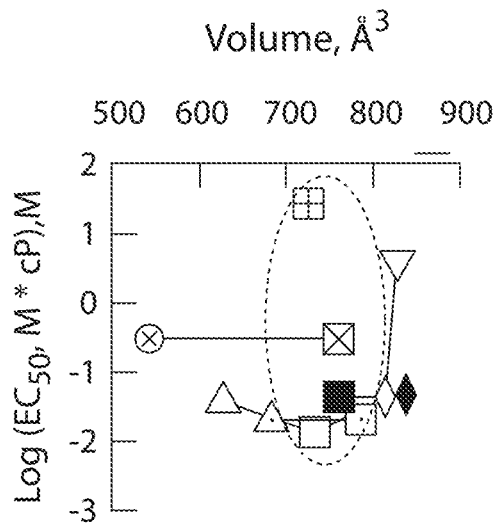
FIG. 21B is a plot showing the potency corrected for differential accumulation into the lipid bilayer as predicted by the partionining coefficient, cP.
Figure 21C:
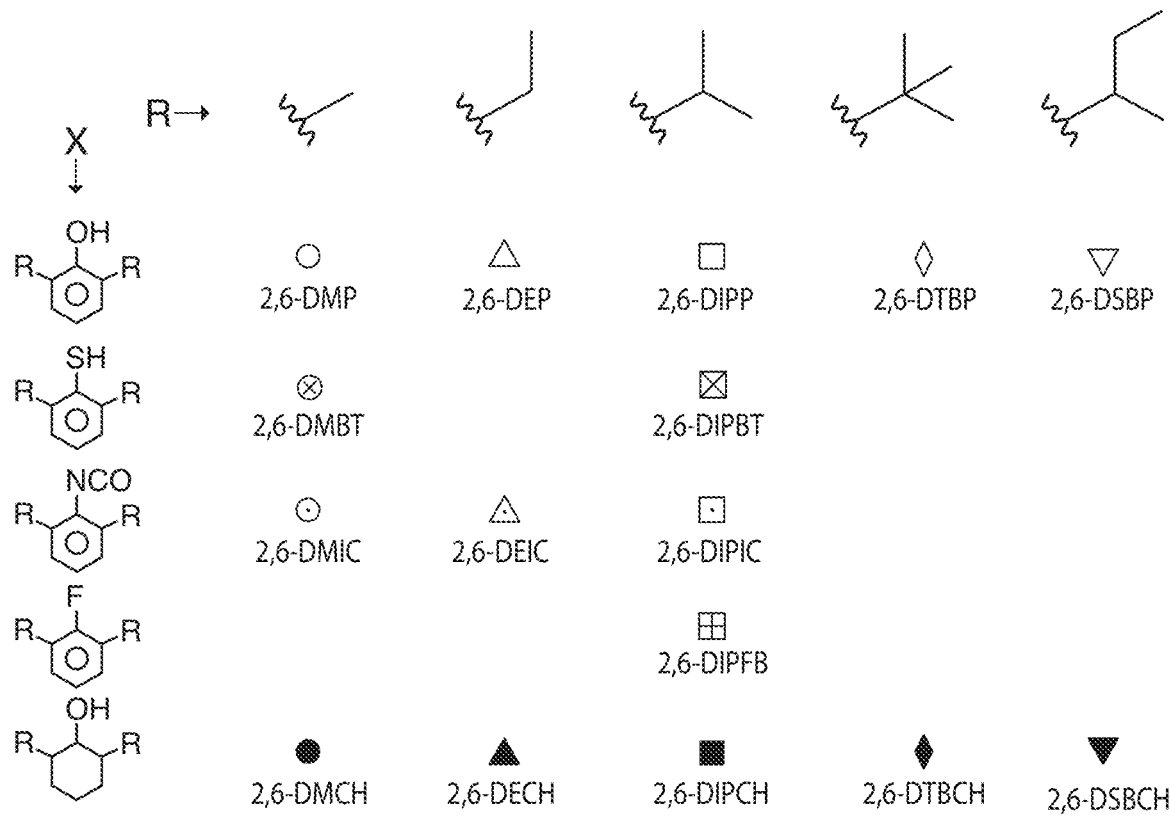
FIG. 21C shows the compound structures of the plots in FIG. 21A and FIG. 21B.

Example 8. Inverse Agonist Potency of 2,6 Di-Alkylbenzene Analogues as a Function of Molecular Volume FIG. 21A plots the observed aqueous $EC_{50}$ as a function of the calculated molecular volume. For ligands where full (2,6-DIPP, 2,6-DTBP) and partial (2,6-DEP, 2,6-DEIC, 2,6-DIPCH, 2,6-DTBCH, 2,6-DSBP) efficacy was apparent, the $EC_{50}$ was determined from fits of the Hill equation to the data as shown in FIG. 20. For ligands where the maximal efficacy was too poorly defined to permit Hill function fitting (2,6-DMBT, 2,6-DIPBT, 2,6-DIPFB, 2,6-DECH) an $EC_{50}$ was estimated from the shifted 2,6-DTBP Hill Fit (thin grey lines in FIG. 20). Where no inflection was observable in the concentration response curve in FIG. 20, the corrected $EC_{50}$ was set equal to 100 mM. In both FIG. 21A and FIG. 21B, the dashed ellipse encircles the data for the iso-propyl family of reagents. In FIG. 21B the plot of the accumulation-corrected $EC_{50}$ (aqueous $EC_{50}$ determined as described in A multiplied by the calculated accumulation ratio, cP) is plotted as a function of the calculated molecular volume. Values for 2,6-DMP (▲), 2,6-DMIC (▲), 2,6-DMCH (▲), 2,6-DECH (■) and 2,6-DSBCH (▼) are omitted for clarity.)

Figure 22:
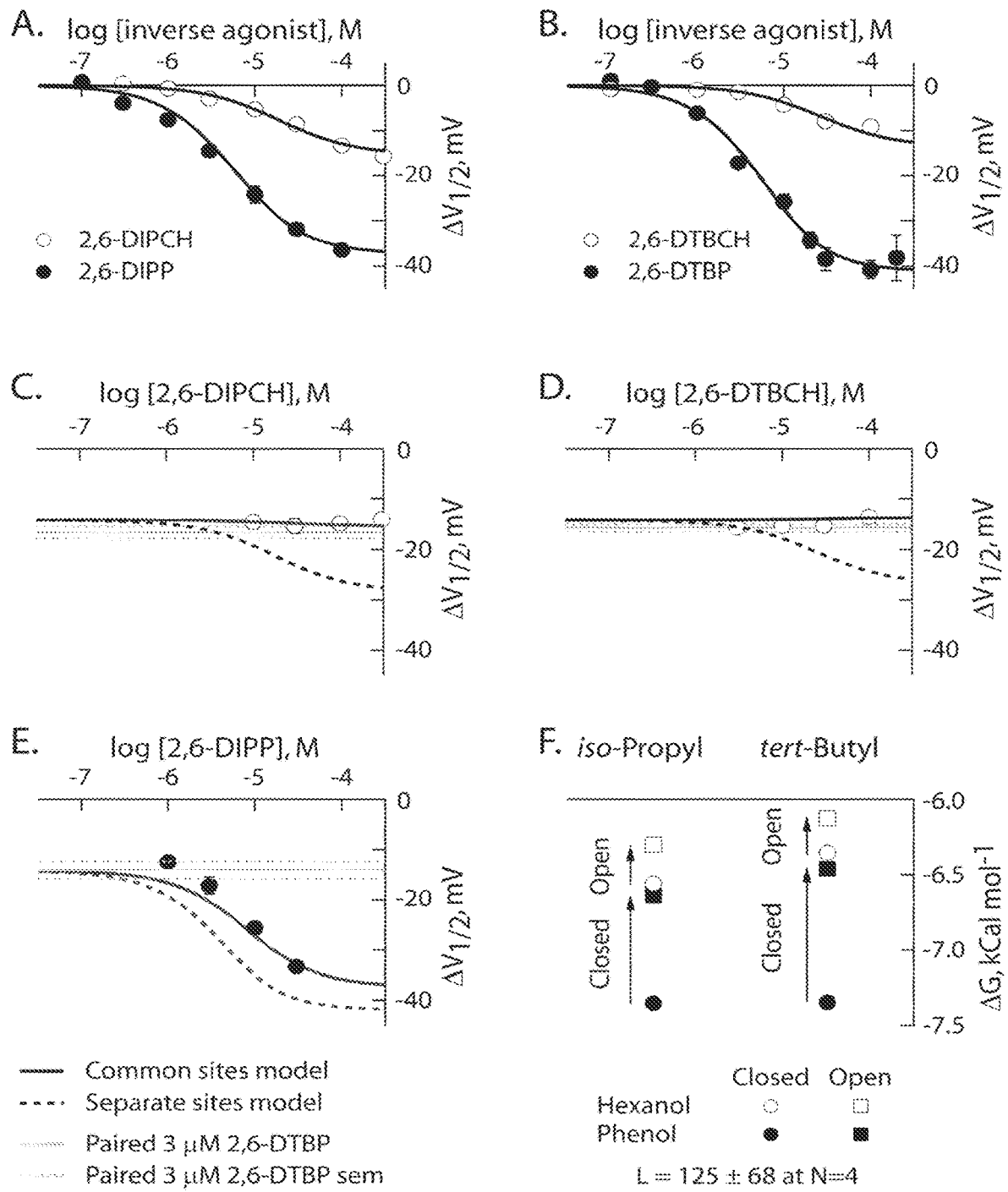
FIG. 22 shows alkylphenols and alkylcyclohexanols associate with HCN1 channels via four common, radially distributed, sites.

Example 9. Alkylphenols and Alkylcyclohexanols Associate with HCN1 Channels Via Four Common, Radially Distributed, Sites FIG. 22A and FIG. 22B shows $\Delta V_{1/2}$ as a function of concentration of iso-propyl (FIG. 22A) and tert-butyl (FIG. 22B) phenols and cyclohexanols. Data are reproduced from FIG. 20. Solid black lines are simultaneous fits of the common site model (N=4) to the data in these two panels and to the data in panels FIG. 22C-E. FIG. 22C-E show $\Delta V_{1/2}$ as a function of concentration of 2,6-DIPCH (FIG. 22C), 2,6-DTBCH (FIG. 22D) or 2,6-DIPP (FIG. 22E), in the presence of 3 µM 2,6-DTBP. The solid black lines are as defined in panels FIG. 22A and FIG. 22B. The dashed black lines are the predicted behavior of the distinct site model at N=4 using the association constants determined from the fit of the common site model. The grey lines report the mean value of $\Delta V_{1/2}$ (solid) and SEM (dashed) elicited by 3 µM 2,6-DTBP in paired controls for each additivity condition. FIG. 22F shows association constants determined from the fits of the common site model with N=4 (as per FIG. 22A-E) transformed to free energy terms according to -(RT)LnK. The reported value of the opening equilibrium constant (L) is from this same fit.

Figure 23:
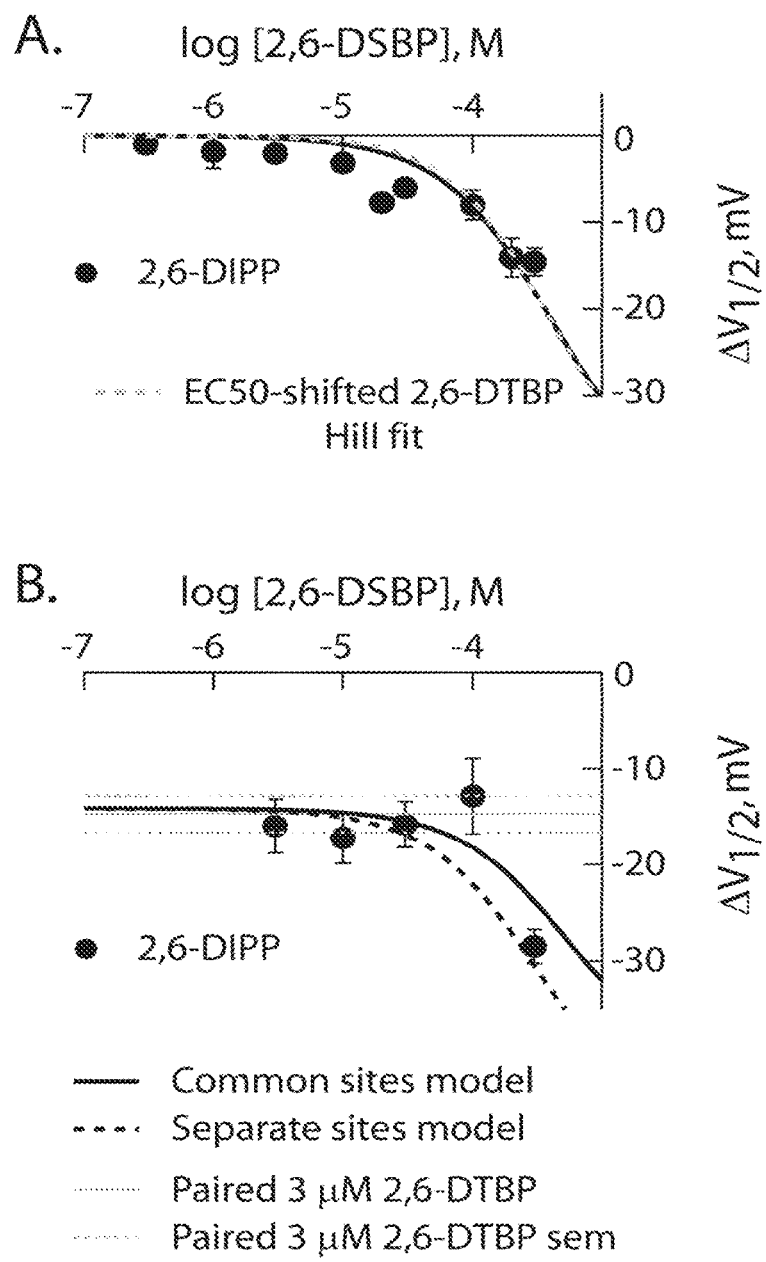
FIG. 23A is a plot showing $\Delta V\frac{1}{2}$ as a function of concentration of 2,6-di-sec-butylphenol (2,6-DSBP) in the absence of 3 µM 2,6-DTBP.
FIG. 23B is a plot showing $\Delta V\frac{1}{2}$ as a function of concentration of 2,6-DSBP in the presence of 3 µM 2,6-DTBP. The plots demonstrate that 2,6-DSBP is a low potency, high efficacy, inverse agonist.
Figure 24A:
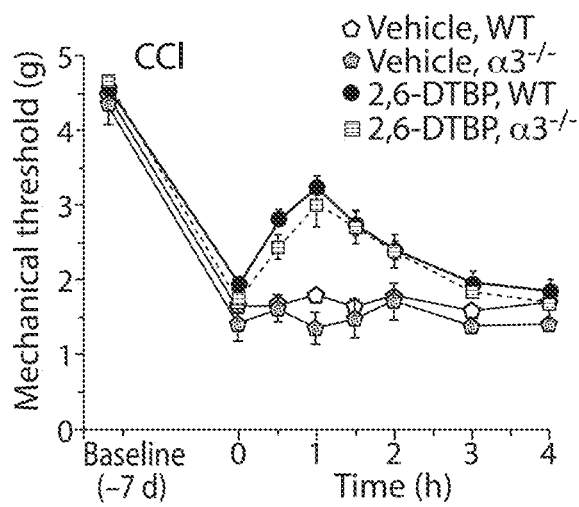
FIG. 24 shows 2,6-DTBP ameliorates mechanical and thermal hyperalgesia in a chronic constriction injury model of peripheral neuropathic pain. Bolus administration of 2,6-DTBP elicits an ~45% reversal of mechanical hypersensitivity (FIG. 24A-B) and a complete reversal of thermal hypersensitivity (FIG. 24C-D) in a manner independent of spinal glycine receptors. Data are from Acuña et al., 2016 J. Clin. Invest 126(7), 2547-60.
Figure 24B:
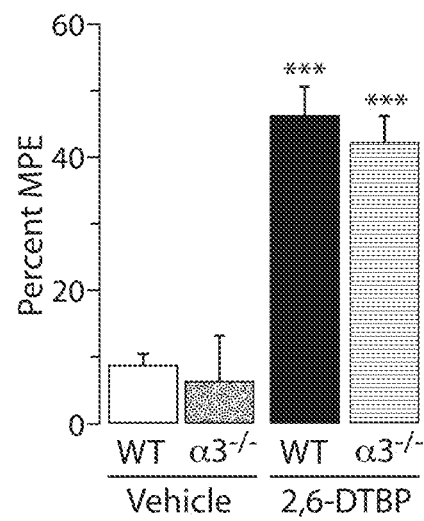
Figure 24C:
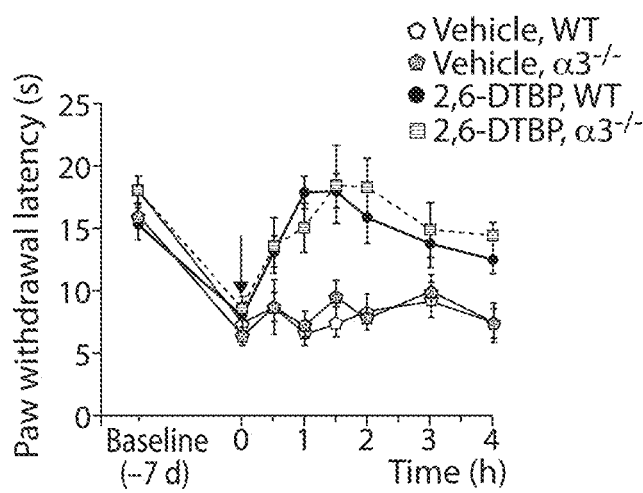
Figure 24D:
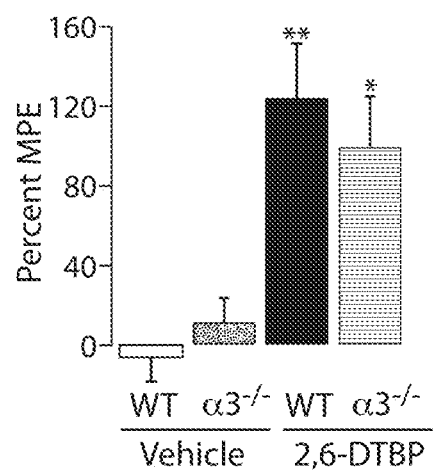
Figure 25A:
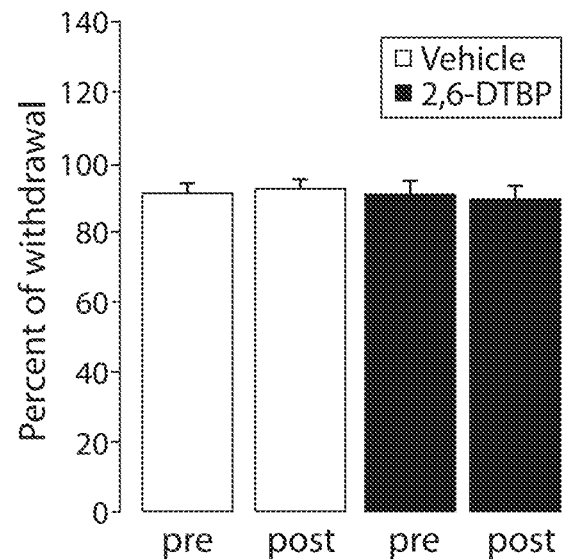
FIG. 25 shows an anti-hyperalgesic dose of 2,6-DTBP does not disrupt normal nociception nor does it perturb locomotor activity, motor coordination and muscle strength). Pin prick test of nociception (FIG. 25A), locomoter activity in an open field (FIG. 25B), motor coordination by time on an accelerating rotor (FIG. 25C) and muscle strength assessed by a horizontal wire test (FIG. 25D). Data are from Acuña et al., 2016 J. Clin. Invest 126(7), 2547-60.
Figure 25B:
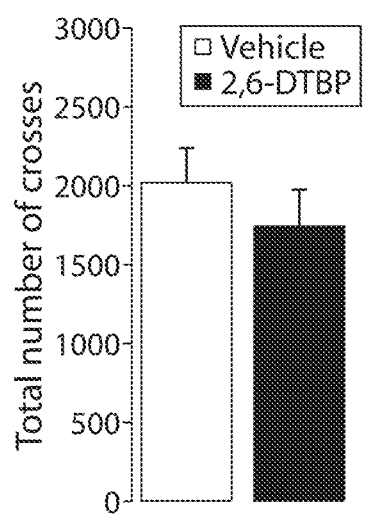
Figure 25C:
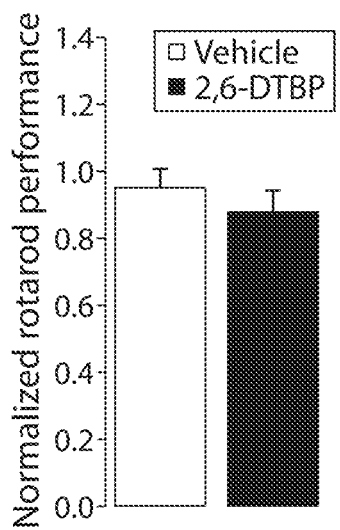
Figure 25D:
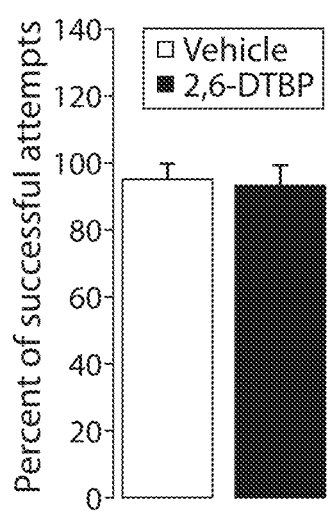
Figure 26:
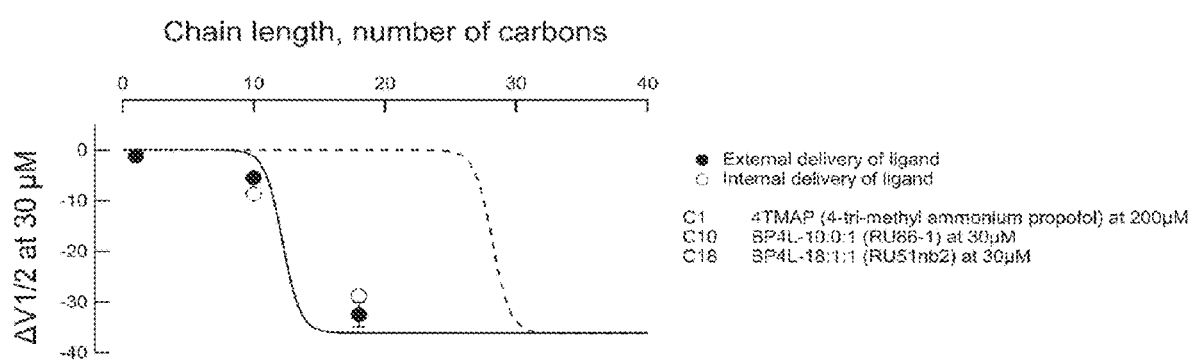
FIG. 26 shows HCN1 antagonism by anchor-tethered 2,6-DTBPs as a function of tether length: The smooth lines are hypothetical plots of efficacy as a function of tether length generated using a Boltzmann distribution wherein the slope incorporates the distribution of molecule lengths due to bond vibration and the tendency of the pharmacophore to pivot into non-orthogonal orientations shortening it with respect to its theoretical maximal reach.

Example 10. A Decreased Inverse Agonist Potency of Large 2,6 Di-Alkylbenzene Analogues Suggests a Defined Upper Limit to the Volume of the Drug Cavity FIG. 23 shows $\Delta V\frac{1}{2}$ as a function of concentration of 2,6-DSBP in the absence (FIG. 23A) and presence (FIG. 23B) of 3 µM 2,6-DTBP. The solid black lines are simultaneous fits of the common site model (N=4) to the data in these two panels with all constants other than JoI and JcI held equal to the values determined in FIG. 23. JoI and JcI as determined from these fits were 881±1,801 and 3,696±2,948, respectively. The dashed black line in FIG. 23B is the predicted behavior for the distinct site model at N=4 with parameters as described above. Discrete fits of the four models yielded χ2 values of 600 and 128 (common site) and 165 and 167 (distinct site) at N equal to 1 and 4, respectively. The symbols and grey line in FIG. 23A are the observed $\Delta V_{1/2}$ for 2,6-DSBP and $EC_{50}$-adjusted 2,6-DTBP fit line ($EC_{50}$ set to 370 µM) reproduced from the 2,6-DSBP panel of FIG. 20. In FIG. 23B, the grey lines report the mean value of $\Delta V_{1/2}$ (solid) and SEM (dashed) elicited by 3 µM 2,6-DTBP in paired controls.

Figure 27:
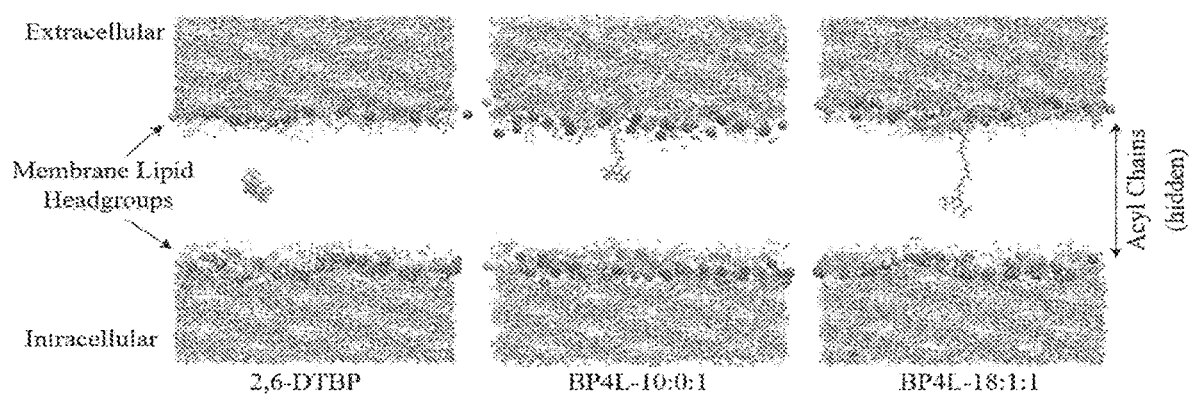
FIG. 27 shows stills from molecular dynamics simulations of (1) free 2,6-DTBP and (2) first-generation anchor-tethered derivates thereof, BP4L-10:0:1 and BP4L-18:1:1.
Figure 28:
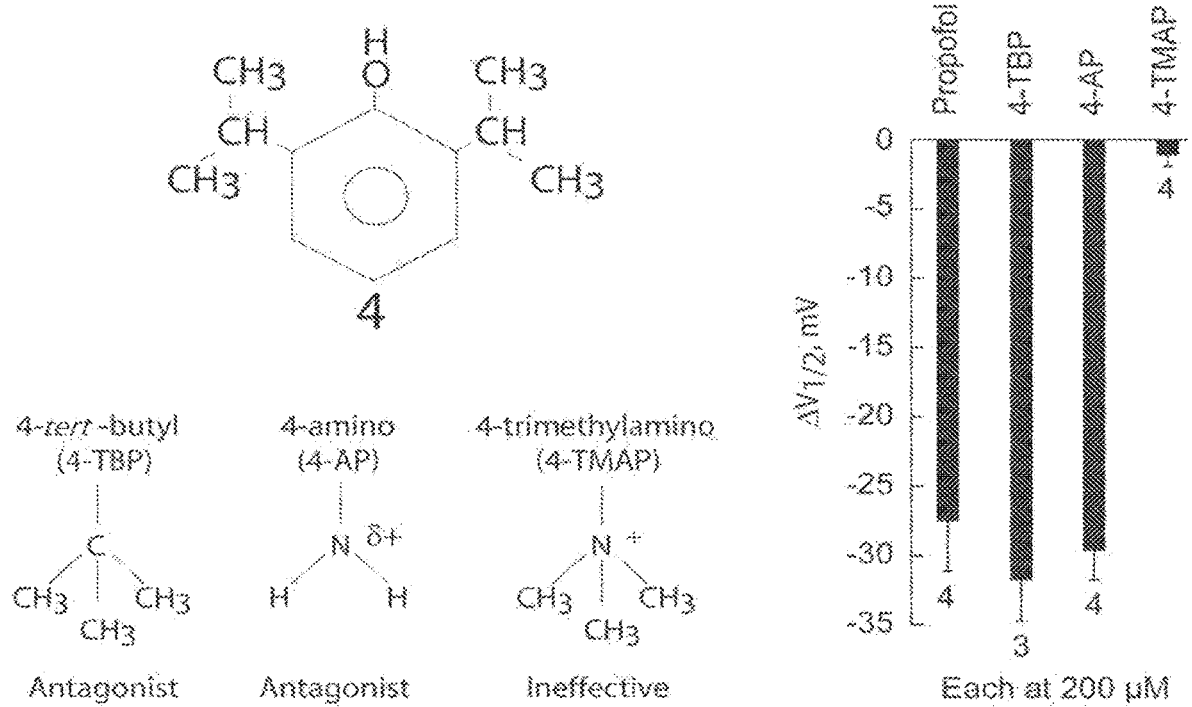
FIG. 28 shows HCN1 antagonism by 4-substituted 2,6-DIPPs. The behavior of 4-substituted di-isopropyl phenols wherein the substitution introduces a 4-amino group (4-AP), a tert-butyl group (4-TBP) or a 4-trimethyl-amino group (4-TMAP) was evaluated. 4-TBP is fully effective. In contrast, 4-TMAP is ineffective. That 4-AP is effective demonstrates that the presence of a nitrogen atom alone is not responsible for the loss of efficacy.

Example 11. Simulations of the Interactions of Exemplary Compounds with the Lipid Bilayer of the Cell Membrane 2,6-DTBP is highly mobile and explores the entire volume of the hydrophobic core of lipid bilayer and adopts completely random orientations (FIG. 27). Additionally, the diol-anchored molecules do not behave like free 2,6-DTBP. Despite being more hydrophobic overall, the diol anchored molecules do not freely distribute into, and freely-move within, the lipid phase. Visual examination of the simulation trajectories shows that the anchor performs generally according to design. Thus, in both molecules (BP4L-18:1:1 and BP4L-10:0:1), The diol shows a strong preference for a polar environment, and the diol settles into the hydrated headgroup phase and spends little time in the hydrophobic core or far out into the aqueous phase.

Both long and short molecules (BP4L-18:1:1 and BP4L-10:0:1, respectively) tend to dwell in a vertical orientation in a manner generally according to design. This behavior is presumably a reflection of two designed constraints: The preference of the diol to remain at the hydrophobic-polar interface. The packing interaction of the acyl tether embedded within the hydrophobic core. The tails of membrane lipids present a dynamic, but relatively well-ordered space that will impose an energetic cost for the tether to adopt anything other than verticality. This cost will presumably be a combination of rotation of the tether's C—C bonds and the coupled displacement of the sea of (ordered) tails of the membrane lipids. While bond rotation presents an intrinsically low thermodynamic cost, displacement of the membrane tails will represent a high entropic cost.

Because of the tether-flexibility, the time-averaged depth of the pharmacophore seems to be less than the calculated average linear length of static molecules but that was always to be expected. On the other hand, as the diol sits within the polar headgroup phase and not outside/above it as expected for a fully efficient anchor, the pharmacophores of both BP4L-10:0:1 and BP4L-18:1:1 reach deep into the membrane. Both can reach to the middle of the bilayer. With BP4L-10:0:1 this occurs infrequently; with BP4L-18:1:1 this may be a preferred arrangement. Indeed, BP4L-18:1:1 can reach beyond the mid-point of the bilayer without the diol anchor detaching from the headgroup phase.

Despite the overall vertical orientation of the tether, both BP4L-10:0:1 and BP4L-18:1:1 exhibit considerable flexibility along the long-axis of the tether, allowing the pharmacophore to explore different depths and orientations with respect to a channel protein that will be (largely) orthogonal to the bilayer. Presentation of the alkyl-hydroxyl face of the pharmacophore orthogonal to the lipid tails seems to require the molecule to pivot across a series of bonds bringing the pharmacophore up towards the surface.

In the initial 300 ns runs, neither molecule shows any overt flipping. However, BP4L-18:1:1 clearly makes several (brief) "diving" sojourns to the inner leaflet. In this arrangement, the phenol transiently associates with the headgroup phase of the inner leaflet while the diol resides within the lipid phase.

Example 12. Compound Synthesis

Synthesis of BP4C-11:0:1

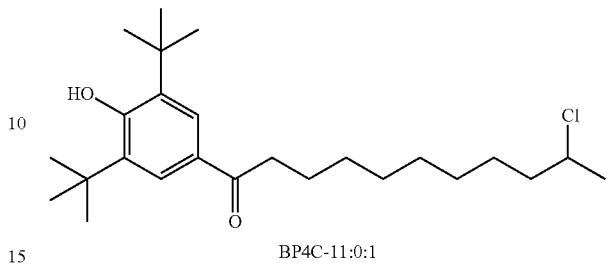

BP4C-11:0:1

Titanium tetrachloride (107 µL, 0.96 mmol) was added drop wise to a solution of the 2,6-di-tert-butyl phenol (200 mg, 0.96 mmol) and 10-undecenoyl chloride (206 µL, 0.96 mmol) in dichloromethane (3.0 mL) at 0° C. under an inert atmosphere. The reaction mixture was stirred for 30 minutes at 0° C. Saturated ammonium chloride solution (2.0 mL) and water (10 mL) were added to quench the reaction. Then, the aqueous layer was extracted with ethyl acetate (2×10 mL). The combined ethyl acetate layer was washed with brine (10 mL), dried with anhydrous sodium sulfate, filtered, and concentrated. The crude residue was purified by column chromatography on silica gel using EtOAc:hexanes (1:25) to furnish BP4C-11:0:1 (290 mg, yield 74%) as an oil; Rf=0.36 using 3% ethyl acetate in hexanes for developing solvent on silica TLC plate. $^1$H NMR (500 MHz, CDCl$_3$): δ=$^1$H NMR (500 MHz, CDCl$_3$): δ=7.85 (s, 2H), 5.69 (s, 1H), 4.04-4.00 (m, 1H), 2.90 (t, J=7.4 Hz, 2H), 1.74-1.68 (m, 4H), 1.51-1.49 (m, 3H), 1.47 (s, 18H), 1.4-1.29 (m, 10H).

Synthesis of BP4K-11:0:1

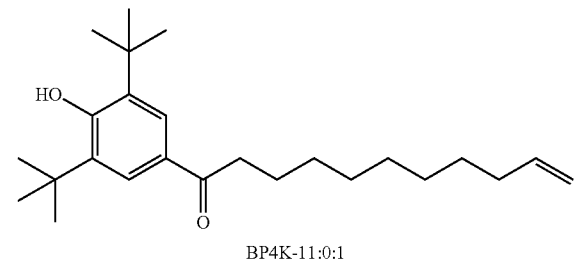 [SMILES: C=CCCCCCCCCC(=O)c1cc(C(C)(C)C)c(O)c(C(C)(C)C)c1]

BP4K-11:0:1

The 2,6-di-tert-butyl phenol (294.6 mg, 1.42 mmol) was added to a mixture of trifluoroacetic anhydride (199 µL, 1.42 mmol) and 10-undecenoic acid (263 mg, 1.42 mmol) at 0° C. under an inert atmosphere. The reaction mixture was stirred for 3 hours 30 minutes at room temperature. Then, the reaction mixture was diluted to ethyl acetate (30 mL) and the resulting organic layer was washed with brine (20 mL), dried with anhydrous sodium sulfate, filtered, and concentrated. The crude product was purified by column chromatography on silica gel using 3% EtOAc in hexanes to furnish corresponding unsaturated ketone intermediate BP4K-11:0:1 (388 mg, yield 73%) as an oil; Rf=0.36 using 3% ethyl acetate in hexanes for developing solvent on silica TLC plate. $^1$H NMR (500 MHz, CDCl$_3$): δ=7.85 (s, 2H), 5.85-7.76 (m, 1H), 5.70 (s, 1H), 5.00-4.91 (m, 2H), 2.90 (t, J=7.4 Hz, 2H), 2.06-2.01 (m, 2H), 1.17-1.69 (m, 2H), 1.47 (s, 18H), 1.37-1.30 (m, 10H).

Synthesis of BP4L-10:0:1

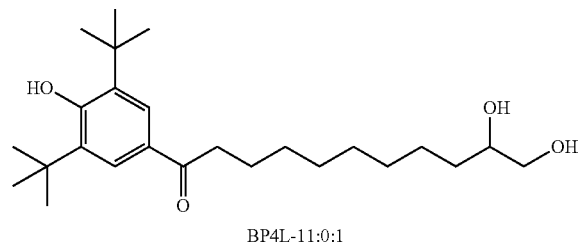 [SMILES: CC(C)(C)c1cc(C(=O)CCCCCCCCC(O)CO)cc(C(C)(C)C)c1O]

BP4L-11:0:1

4-Methyl morpholino N-oxide (51 mg, 0.37 mmol) was added to the unsaturated ketone BP4K-11:0:1 (35 mg, 0.09 mmol) dissolved in a mixture of acetone (0.5 mL) and t-butanol (100 μL) at room temperature. Then, water (300 μL) and catalytic amount of Osmium tetraoxide was added and the reaction was stirred for 40 minutes. Then, the reaction was diluted with ethyl acetate (10 mL), water (5 mL), and quenched with sodium hydrosulfite (87 mg, 0.43 mmol) dissolved in water (2.0 mL). The reaction mixture was stirred for 10 minutes. Then the aqueous mixture was extracted with ethyl acetate (2×10 mL). The combined ethyl acetate layer was washed with saturated sodium bicarbonate solution (10 mL), water (15 mL), brine (10 mL), dried with anhydrous sodium sulfate, filtered, and concentrated. The obtained crude product was purified by column chromatography on silica gel using EtOAc:hexanes (9:1) to furnish diol BP4L-10:0:1 (31 mg, yield 81%) as a yellow oil; Rf=0.38 using 30% ethyl acetate in hexanes for developing solvent on silica TLC plate. $^1$H NMR (500 MHz, CDCl$_3$): δ=7.84 (s, 2H), 5.70 (s, 1H), 3.72-3.69 (m, 1H), 3.66-3.63 (m, 1H), 3.45-3.41 (m, 1H), 2.91-2.88 (m, 2H), 2.21 (br, 2H), 1.72-1.70 (m, 2H), 1.46 (s, 18H), 1.43-1.42 (m, 3H), 1.33-1.31 (m, 9H). $^{13}$C NMR (125 MHz, CDCl$_3$): δ=200.2, 158.2, 135.7, 128.9, 125.8, 72.3, 66.9, 38.19, 34.3, 33.2, 29.5, 29.4, 29.3, 25.5, 24.8

General Strategy for the Synthesis of 4-(Oxo)-Substituted 2,6-Dialkylphenols

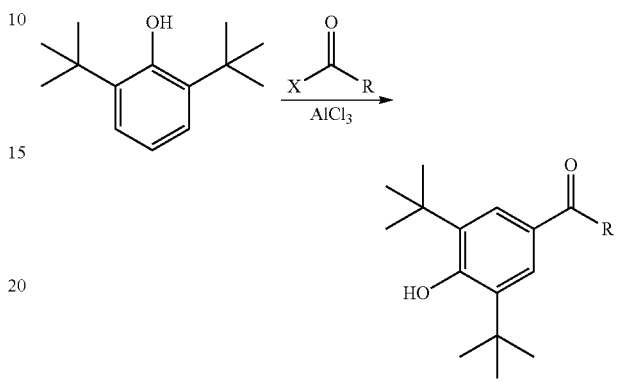

Exemplary Synthesis of a 4-(Oxo)-Substituted 2,6-Dialkylphenol

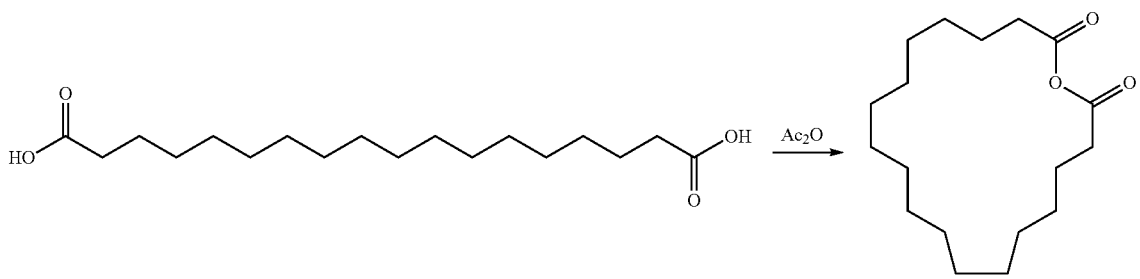 [SMILES: "Ac2O" ; O=C(O)CCCCCCCCCCCCCCCCC(=O)O ; O=C1CCCCCCCCCCCCCCCCC(=O)O1]

oxacyclononadecane-2,19-dione: To a stirred solution of octadecanedioic acid (300 mg, 875 μmol) in dichloromethane (2 mL) was added acetic anhydride (860 μL, 8.76 mmol). The reaction mixture was stirred at ambient temperature for 3 h and then concentrated in vacuo provide the title compound as a clear, colorless oil that foamed under vacuum (220 mg, 677 μmol, 77%). This material was then used without further purifications. $^1$H NMR (500 MHz, DMSO-d6) δ 2.22 (m, 4H), 1.55 (m, J=7.1 Hz, 4H), 1.25 (br, 28H).

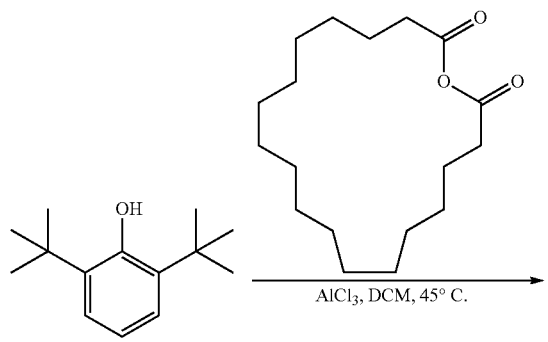

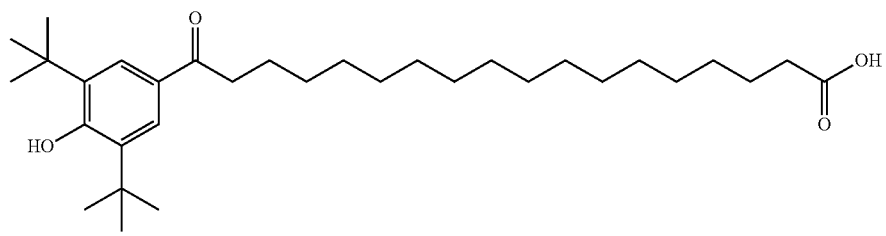

1

18-(3,5-di-tert-butyl-4-hydroxyphenyl)-18-oxooctadecanoic acid, 1: To an oven dried flask was added 2,6-di-tert-butylphenol (1.0 g, 4.85 mmol), oxacyclononadecane-2,19-dione (1.44 g, 4.85 mmol), and dichloromethane (DCM, 100 mL). The resulting mixture was magnetically stirred until all reactants were solubilized, and then aluminum chloride (646 mg, 4.85 mmol) was added portion-wise. The reaction was heated to 45° C. and stirred overnight. The reaction was quenched by the addition of water (100 mL) and extracted with DCM (3×100 mL). The combined organic layers were dried ($Na_2SO_4$) and concentrated. Purification was done using automated flash chromatography (50% MeOH in DCM) to provide compound 1 as a yellow oil (1.77 g, 3.34 mmol, 68%). $^1$H NMR (500 MHz, $CDCl_3$) δ 7.84 (s, 2H), 5.72 (s, 1H) 3.49 (s, 2H), 2.55 (s, 3H), 2.22 (s, 31H), 1.47 (s, 20H), 1.39-1.14 (br, 21H), 0.93-0.81 (brm, 13H).

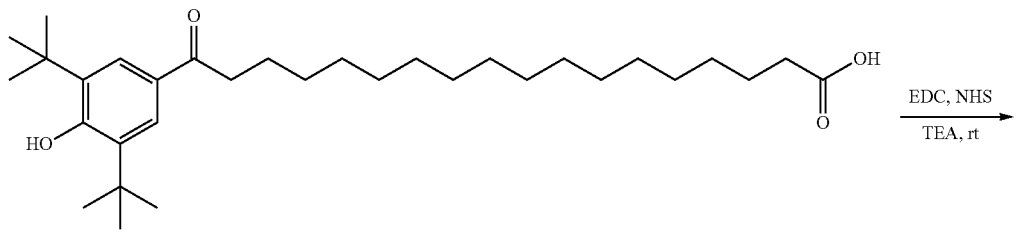

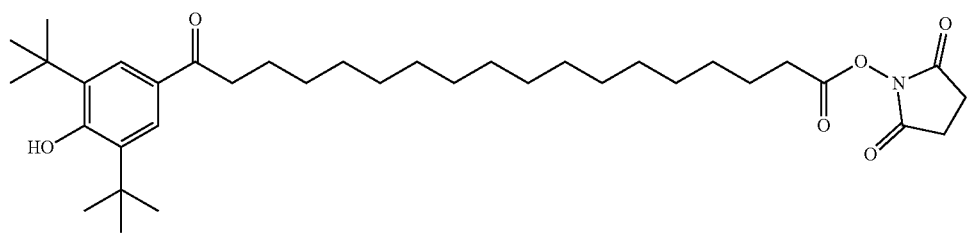

2

2,5-dioxopyrrolidin-1-yl 18-(3,5-di-tert-butyl-4-hydroxyphenyl)-18-oxooctadecanoate, 2: To an oven dried flask was added compound 1 (52 mg, 98 μmol), EDC (37 mg, 196 μumop, NHS (23 mg, 196 μumop, and DMF (1 ml). The mixture was magnetically stirred and triethylamine (27 μL, 196 μmol) was added. The reaction mixture was stirred overnight at ambient temperature, then the solvents were removed by rotary evaporation and the crude mixture purified using mass directed LCMS. Fractions containing compound 2 were combined and lyophilized to provide slightly yellow gelatinous material. $^1$H NMR (500 MHz, CHCl$_3$) δ 7.86 (s, 3H), 5.74 (s, 1H), 2.58 (s, 4H), 2.18 (d, J=16.2 Hz, 2H), 1.94-1.55 (m, 3H), 1.49 (br, 25H), 1.43-0.77 (brm, 13H).

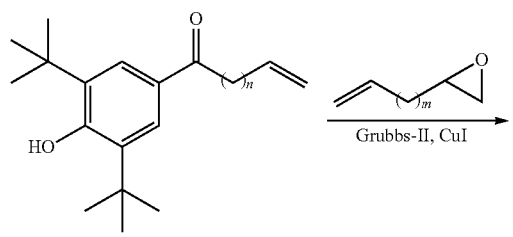

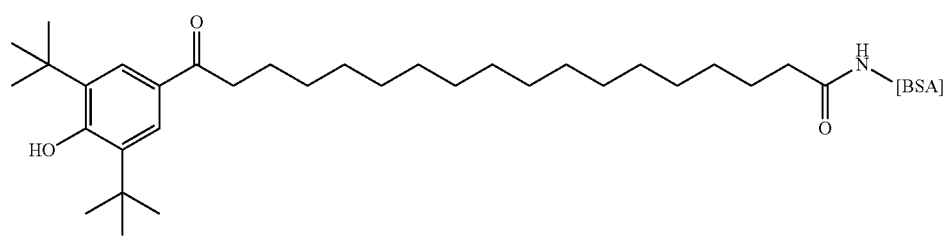

3

BSA conjugate: BSA (66.5 kDa) was dissolved at a concentration of 2.5 mg/mL in 0.05 M phosphate buffered saline (pH 7.4) in a glass vial. To this was added 500 μL compound 2 as a 55 mg/mL solution in DMF/acetonitrile (1:1 v/v). The mixture was incubated for 12 h at 37° C., at which point LCMS analysis of the reaction did not show the presence of either compound 1 (m/z of [M−H]$^-$=529.5) or compound 2 (m/z of [M+H]$^+$=628.5). Analysis occurred by diluting 10 μL of reaction mixture with 0.5 ml chloroform to precipitate the protein, followed by centrifugation and sampling of the supernatant. The crude reaction mixture was lyophilized and used without further purification.

Alternative Strategy for the Synthesis of 4-(Oxo)-Substituted 2,6-Dialkylphenols

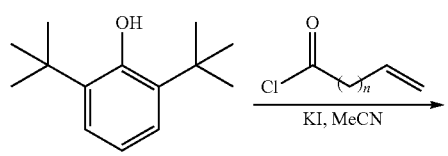

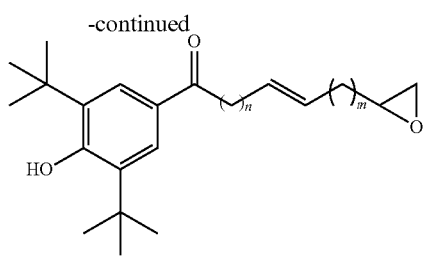

Exemplary Synthesis of a 4-(Oxo)-Substituted 2,6-Dialkylphenol Bearing a Trans Alkenyl Moiety

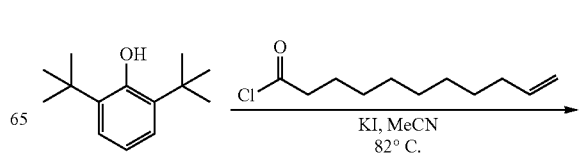

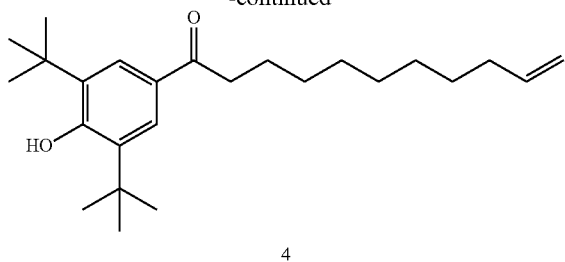

4

1-(3,5-di-tert-butyl-4-hydroxyphenyl)undec-10-en-1-one, 4: To an oven dried pressure tube containing potassium iodide (1.64 g, 9.87 mmol) and 2,6-di-tert-butylphenol (1.02 g, 4.93 mmol) was added anhydrous MeCN (10 mL) and then undec-10-enoyl chloride (2 g, 9.87 mmol). The tube was then sealed, and the reaction mixture was heated to 82° C., stirred for 24 h, and then cooled to ambient temperature. The solution was quenched with water (10 mL) and extracted with DCM (3×50 mL). The combined organic layers were washed with saturated sodium thiosulfate solution, then dried ($Na_2SO_4$) and concentrated in vacuo. Purification by column chromatography (1% EtOAc in hexanes) provided compound 4 as a yellow oil (3.2 g, 10.2 mmol, 87%). $^1$H NMR (500 MHz, $CDCl_3$) δ 7.87 (s, 2H), 7.33 (d, J=7.9 Hz, 2H), 7.15 (q, J=8.3 Hz, 1H), 5.83 (m, 1H), 5.08-4.87 (m, 3H), 2.92 (m, 2H), 2.70-2.57 (m, 2H), 2.13-1.97 (m, 3H), 1.97-1.90 (m, 2H), 1.76 (m, 511), 1.69-1.54 (m, 7H), 1.49 (s, 20H), 1.42-1.28 (br, 39H). ESIMS of $C_{25}H_{40}O_2$; theoretical m/z of [M−H]$^-$=371.3, measured m/z of [M−H]$^-$=371.5

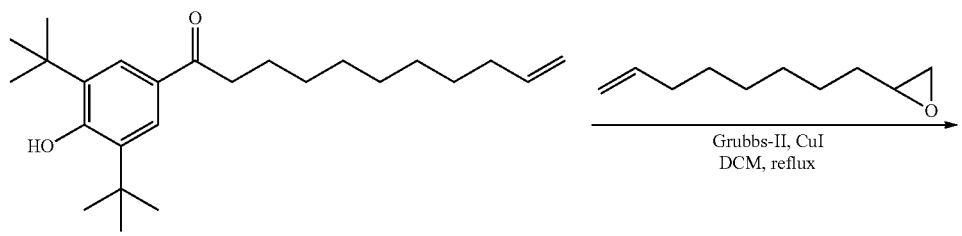

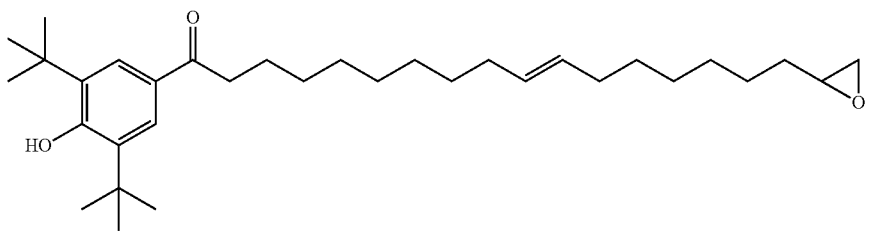

5

(E)-1-(3,5-di-tert-butyl-4-hydroxyphenyl)-17-(oxiran-2-yl)heptadec-10-en-1-one, 5: Grubbs' second generation catalyst (114 mg, 1.34 mmol) was added to a stirred suspension of CuI (26 mg, 134 μmol) in a solution of compound 4 (500 mg, 1.34 mmol) and 2-(oct-7-en-1-yl)oxirane (207 mg, 1.34 mmol) in dry DCM (6 mL) under argon atmosphere. The resulting mixture was stirred at ambient temperature for 15 min, then heated to reflux and stirred for 4 h. At that point, the reaction mixture was cooled to ambient temperature, and three drops of DMSO was added. The resulting solution stirred overnight and was then concentrated in vacuo. The resulting residue was purified by automated flash chromatography (EtOAc/pet ether, 15:85) to provide compound 5 as a light brown liquid (475 mg, 0.95 mmol, 71%). $^1$H NMR (500 MHz, $CDCl_3$) δ 7.86 (s, 2H), 5.71 (s, 1H), 5.50-5.29 (m, 2H), 2.92 (t, J=7.3 Hz, 3H), 2.77 (m, 1H), 2.48 (m, 1H), 2.11-1.91 (m, 5H), 1.81-1.65 (m, 3H), 1.60-1.21 (br, 43H).

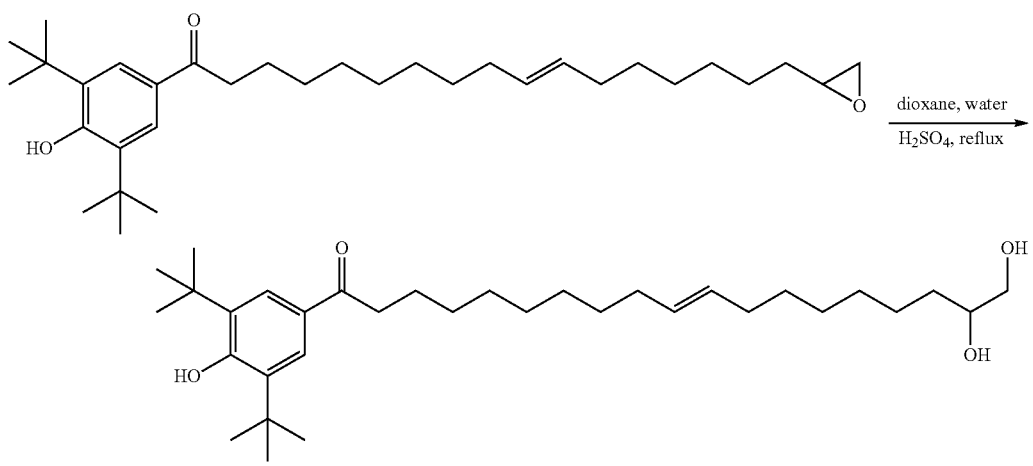

6

(E)-1-(3,5-di-tert-butyl-4-hydroxyphenyl)-18,19-dihydroxynonadec-10-en-1-one, 6 (BP4L-18:1:1): Compound 5 (600 mg, 1.20 mmol) was dissolved in a mixture of dioxane/water/$H_2SO_4$ (2:1:1 v/v. 7 mL) and heated at reflux for 18 hrs. The reaction mixture was then cooled to ambient temperature, extracted with water and dichloromethane, then concentrated in vacuo. The resulting residue was purified by automated flash chromatography (20% EtOAc in DCM) to provide compound 6 as a dark brown liquid (450 mg, 0.87 mmol, 72%) m/z of [M−H]−=514.4, measured m/z of [M−H]−=514.5, $^1$H NMR (500 MHz, CDCl$_3$) δ 7.86 (s, 2H), 5.72 (s, 1H), 5.50-5.30 (m, 2H), 3.78-3.63 (m, 3H), 3.46 (dd, J=11.0, 7.7 Hz, 1H), 2.92 (t, J=7.4 Hz, 2H), 1.98 (d, J=7.4 Hz, 5H), 1.52-1.19 (br, 46H); $^{13}$C NMR (126 MHz, CDCl$_3$) δ 200.3, 158.3, 135.7, 128.9, 125.8, 114.2, 72.3, 66.8, 53.4, 38.2, 34.4, 33.7, 33.2, 33.2, 32.6, 32.5, 30.2, 29.6, 29.5, 29.5, 29.4, 29.1, 28.8, 25.5, 25.4, 24.8, 24.8. ESIMS of $C_{33}H_{56}O_4$: theoretical m/z of [M−H]−=514.4, actual 514.5.

extracted with DCM (3×50 mL). The combined organic layers were washed with saturated sodium thiosulfate solution, then dried ($Na_2SO_4$) and concentrated in vacuo. Purification by column chromatography (1% EtOAc in hexanes) provided compound 7 as a yellow oil (1.4 g, 2.69 mmol, 52%). $^1$H NMR (500 MHz, CDCl$_3$) δ 7.20 (d, J=7.8 Hz, 2H), 6.85 (t, J=7.8 Hz, 1H), 5.23 (s, 1H), 3.46-3.31 (m, 4H), 1.91-1.78 (m, 4H), 1.55-1.21 (br, 36H).

LCMS/MS was performed on an Agilent 1290 Infinity II UPLC system and Agilent 6495 Triple Quadrupole mass spectrometer. Separation was achieved at 45° C. with a BEH C18, 1.7 μm, 2.1×50 mm column (Waters) and a 7 min gradient comprised of 10% B for 0.5 min, then 10% to 95% B over 3 minutes, followed by 95% B for the remainder of the separation; mobile phase A consisted of 0.1% formic acid in water; mobile phase B consisted of 0.1% formic acid in acetonitrile. There was a 3-minute equilibration at 10% B

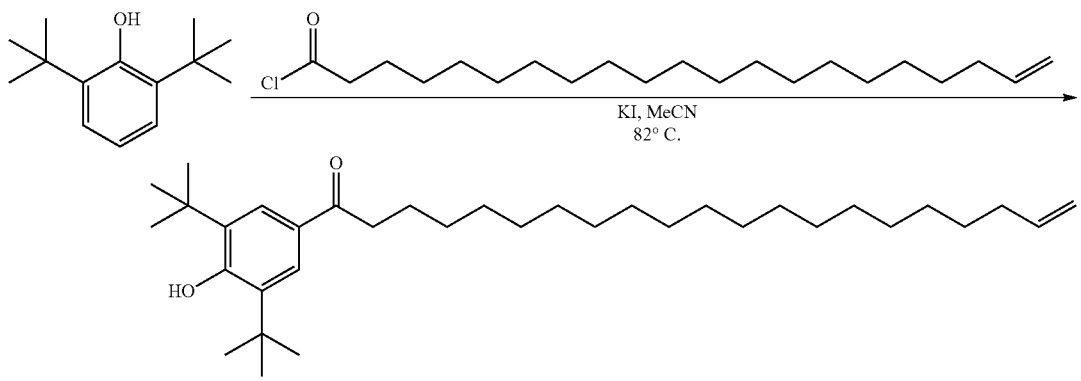

7

1-(3,5-di-tert-butyl-4-hydroxyphenyl)henicos-20-en-1-one, 7: To an oven dried pressure tube containing potassium iodide (871 mg, 5.25 mmol) and 2,6-di-tert-butylphenol (1.2 g, 5.25 mmol) was added anhydrous MeCN (10 mL) and then henicos-20-enoyl chloride (1.8 g, 5.25 mmol). The tube was then sealed, and the reaction mixture was heated to 82° C., stirred for 24 h, and then cooled to ambient temperature. The solution was quenched with water (10 mL) and following each injection. Flow rate was 0.5 mL/min; 2 μL of sample was introduced onto the column by an Agilent 1290 Infinity II Multisampler. Retention time for BP4L-18.1.1 was 5.93 min. Quantitation was performed using multiple reaction monitoring in positive electrospray ionization mode using the transition 517.4→233.1 and a collision energy of 42. Source specific parameters were: gas temperature, 120° C.; gas flow, 11 L/min; nebulizer, 22 psi; sheath gas temperature, 400° C.; sheath gas flow, 12 L/min; capillary voltage, 2500 V; nozzle voltage 0 V; high pressure RF, 150 V; low pressure RF, 110 V.

Sample Preparation

Figure 30:
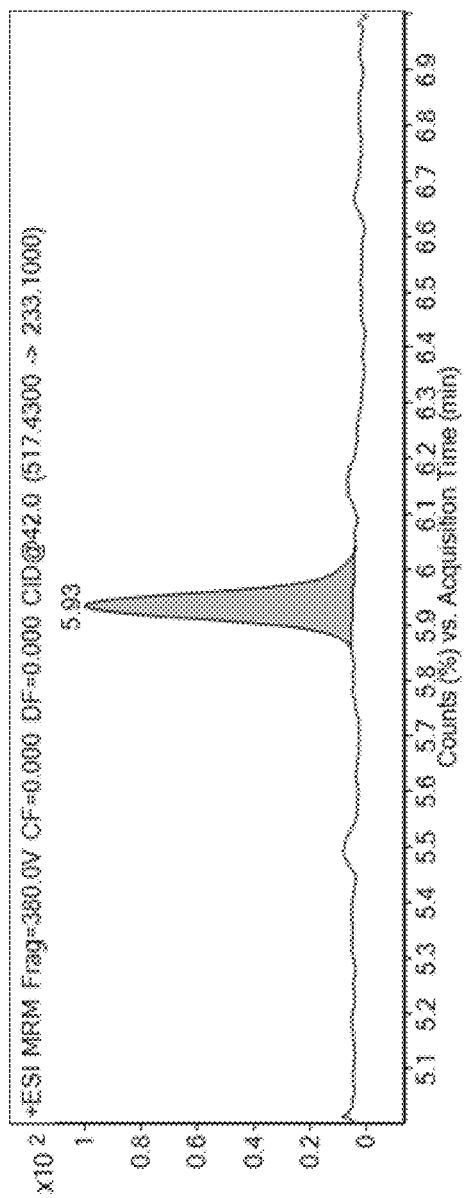
FIG. 30 shows the chromatogram of the supernatant used for LCMS analysis.

200 μL of LCMS grade acetonitrile was added to 200 pit of blood in a 1 mL Eppendorf tube and vortex mixed for 10 seconds, then centrifuged at 2400×g for 15 min. 200 μL was removed from the supernatant, placed into a fresh 1 mL Eppendorf tube, and centrifuged at 5300×g for 15 min. Finally, 100 μL of supernatant was removed and passed through a 0.2 μm modified nylon centrifugal filter to remove any protein remnants. The resulting supernatant was used for LCMS analysis without further modification is shown in FIG. 30.

Additional compounds can be synthesized according to the following schemes:

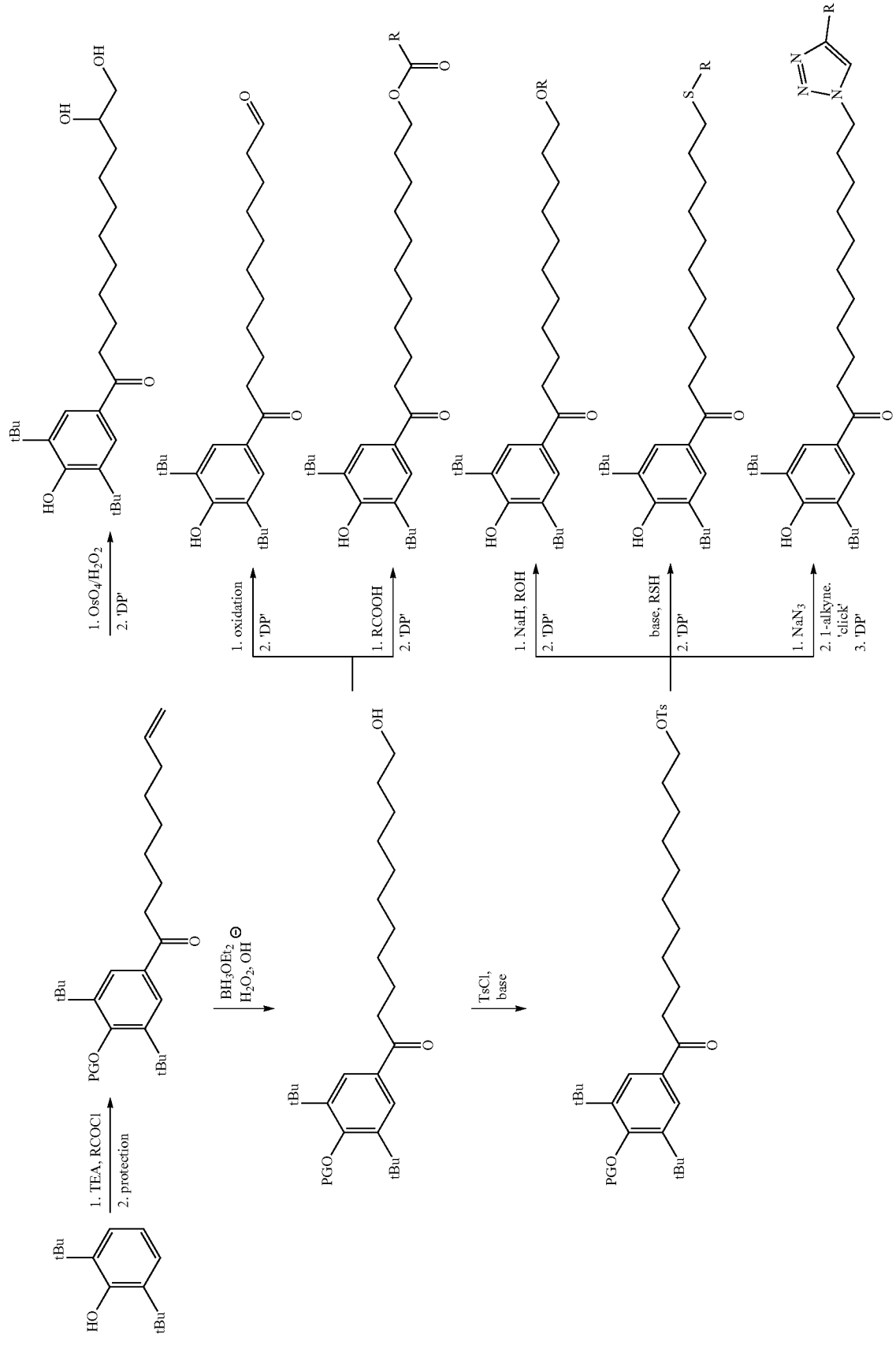

Example 14. Pharmacokinetics

Figure 29:
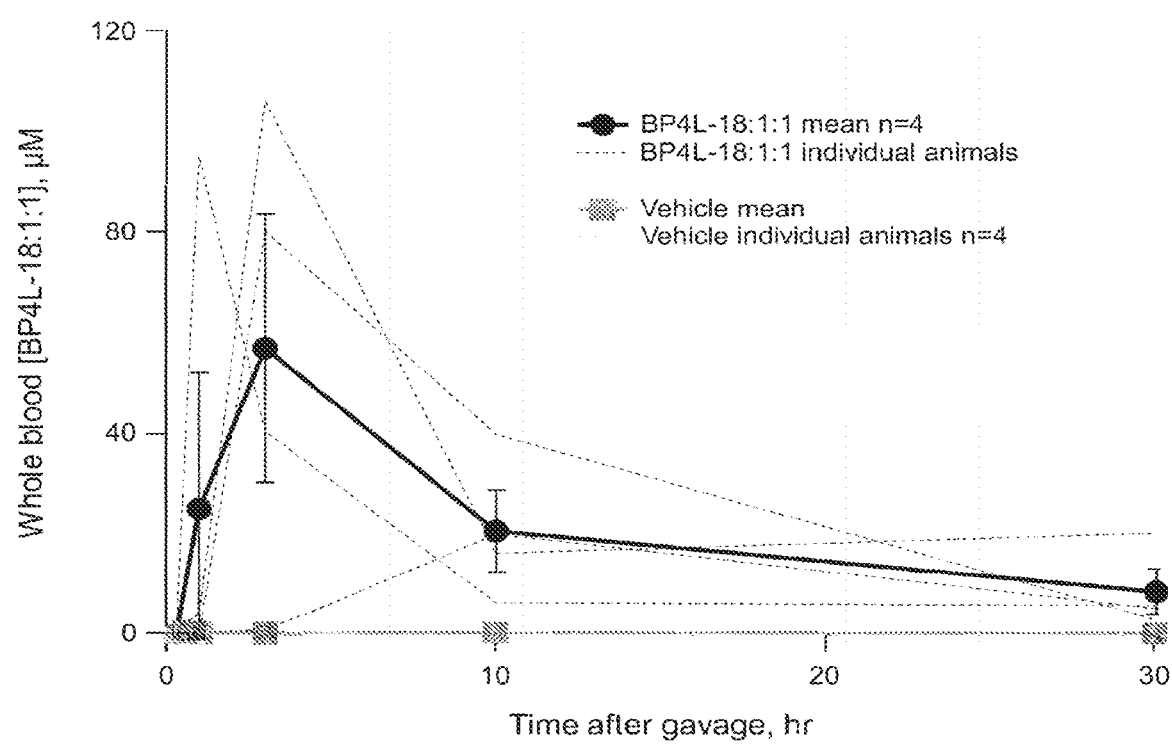
FIG. 29 is a graph showing the concentration of BP4L-18:1:1 in whole blood after administration to rats. Eight adult rats were gavaged with either 0.5 mL of peanut oil (n=4) or 0.5 mL of peanut oil containing 0.58 mmole/kg BP4L-18:1:1 (n=4). Blood samples were obtained at the indicated times. Following extraction using equi-volumes of acetonitrile, precipitation and filtration, blood concentrations of BP4L-18:1:1 were determined using LC-MS/MS. Dotted black lines indicate the concentrations of BP4L-18:1:1 for individual animals that received drug, the solid black line indicates the mean±SEM for the plus-drug cohort. Dotted and solid grey lines are, respectively, the concentrations of BP4L-18:1:1 detected in individual peanut oil-alone animals and the mean±SEM thereof. Grey lines superimpose and are indistinguishable from the time axis.

Pharmacokinetic properties of exemplary compound BP4L-18:1:1 (compound 6) were evaluated in rats (FIG. 29). In particular, concentration of BP4L-18:1:1 in whole blood samples were determined over the course of 30 hours after oral administration. The results show that the compound was absorbed demonstrating bioavailability.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects described herein, is/are referred to as comprising particular elements and/or features, certain embodiments described herein or aspects described herein consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments described herein, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A compound selected from the group consisting of:

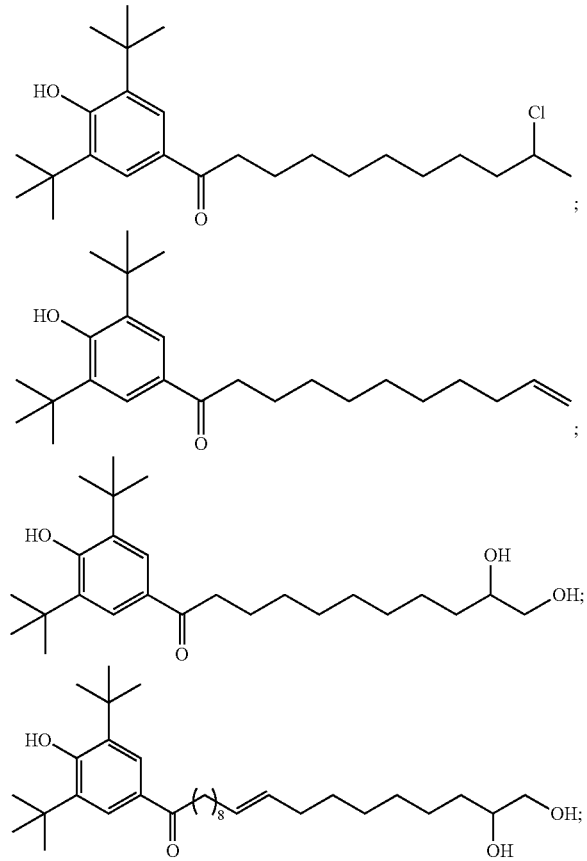
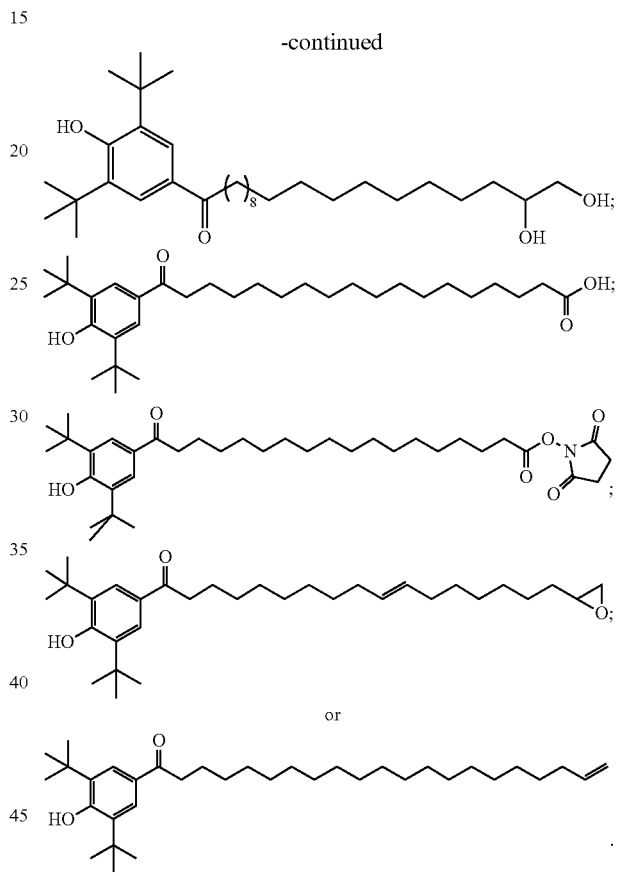

2. A pharmaceutical composition comprising a compound of claim 1 and a pharmaceutically acceptable carrier.

* * * * *

UNITED STATES PATENT AND TRADEMARK OFFICE
CERTIFICATE OF CORRECTION

| | |
|---|---|
| PATENT NO. | : 11,684,590 B2 |
| APPLICATION NO. | : 17/254787 |
| DATED | : June 27, 2023 |
| INVENTOR(S) | : Gareth R. Tibbs et al. |

It is certified that error appears in the above-identified patent and that said Letters Patent is hereby corrected as shown below:

In the Claims

Claim 1, Column 88, Line 41:
"or"
Is replaced with:
-- and --.

Signed and Sealed this
Nineteenth Day of March, 2024

Katherine Kelly Vidal
*Director of the United States Patent and Trademark Office*